US011859242B2

(12) United States Patent
Ly et al.

(10) Patent No.: US 11,859,242 B2
(45) Date of Patent: Jan. 2, 2024

(54) TEMPLATE-DIRECTED NUCLEIC ACID TARGETING COMPOUNDS

(71) Applicant: Carnegie Mellon University, Pittsburgh, PA (US)

(72) Inventors: Danith H. Ly, Pittsburgh, PA (US); Wei-Che Hsieh, New Taipei (TW); Raman Bahal, Glastonbury, CT (US)

(73) Assignee: Carnegie Mellon University, Pittsburgh, PA (US)

( * ) Notice: Subject to any disclaimer, the term of this patent is extended or adjusted under 35 U.S.C. 154(b) by 701 days.

(21) Appl. No.: 16/955,593

(22) PCT Filed: Dec. 21, 2018

(86) PCT No.: PCT/US2018/067096
§ 371 (c)(1),
(2) Date: Jun. 18, 2020

(87) PCT Pub. No.: WO2019/126646
PCT Pub. Date: Jun. 27, 2019

(65) Prior Publication Data
US 2020/0340044 A1    Oct. 29, 2020

Related U.S. Application Data

(60) Provisional application No. 62/708,789, filed on Dec. 21, 2017.

(51) Int. Cl.
| *C12Q 1/6816* | (2018.01) |
| *C07H 21/02* | (2006.01) |
| *C07H 1/04* | (2006.01) |
| *G01N 21/76* | (2006.01) |
| *C07H 21/04* | (2006.01) |

(52) U.S. Cl.
CPC ........... *C12Q 1/6816* (2013.01); *C07H 21/02* (2013.01); *C07H 21/04* (2013.01); *G01N 21/76* (2013.01)

(58) Field of Classification Search
CPC ............ C12Q 1/6818; C12Q 2565/101; C07H 21/00; G01N 21/26
See application file for complete search history.

(56) References Cited

U.S. PATENT DOCUMENTS

| 6,395,474 | B1 | 5/2002 | Buchardt et al. |
| 6,747,014 | B2 | 6/2004 | Teng et al. |
| 8,053,212 | B1 | 11/2011 | Benner |
| 8,389,703 | B1 | 3/2013 | Benner et al. |
| 8,653,254 | B2 | 2/2014 | Umemoto et al. |
| 2011/0028337 | A1 | 2/2011 | Bradley et al. |
| 2014/0128570 | A1 | 5/2014 | Ly et al. |
| 2015/0197793 | A1 | 7/2015 | Armitage et al. |
| 2016/0083434 | A1 | 3/2016 | Ly et al. |
| 2017/0058325 | A1* | 3/2017 | Ly ........................ C12Q 1/6858 |

FOREIGN PATENT DOCUMENTS

| EP | 0810291 A1 | 12/1997 |
| WO | 2012138955 A2 | 10/2012 |
| WO | 2012138955 A3 | 10/2012 |
| WO | 2013074601 A1 | 5/2013 |
| WO | 2014169206 A2 | 10/2014 |
| WO | 2018058091 A1 | 3/2018 |

OTHER PUBLICATIONS

Stemmer et al., PNAS 91: 897 (Year: 1988).*
Cremari et al., Nature 387 : 435 (Year: 1994).*
Rohilla et al., "RNA biology of disease-associated microsatellite repeat expansions", Acta Neuropathologica Communications, 2017, pp. 1-22, vol. 5, No. 63.
Taneja, K. L., "Localization of Trinucleotide Repeat Sequences in Myotonic Dystrophy Cells Using a Single Fluorochrome-Labeled PNA Probe", BioTechniques, 1998, pp. 472-476, vol. 24.
Immordino et al., "Stealth liposomes: review of the basic science, rationale, and clinical applications, existing and potential", International Journal of Nanomedicine, 2006, pp. 297-315, vol. 1:3.
Lee et al., "Controlling the Specificity of Modularly Assembled Small Molecules for RNA via Ligand Module Spacing: Targeting the RNAs that Cause Myotonic Muscular Dystrophy", Journal of the American Chemical Society, 2009, pp. 1-19, vol. 131:47.
International Search Report and Written Opinion re PCT/US18/67096.
Bahal et al. "Targeting abnormal triplet repeat containing hairpin RNA by using mini-PEG PNA." Abstracts of Papers of the American Chemical Society, 2011, pp. 1-3, vol. 242.
Isieh et al. "Design of a "Mini" Nucleic Acid Probe for Cooperative Binding of an RNA-Repeated Transcript Associated with Myotonic Dystrophy Type 1", Biochemistry, 2018, pp. 907-911, vol. 57.
Sahu et al. "Synthesis and Characterization of Conformationally Preorganized, (R)-Diethylene Glycol-Containing γ-Peptide Nucleic Acids with Superior Hybridization Properties and Water Solubility", The Journal of Organic Chemistry, 2011, pp. 5614-5627, vol. 76.
Sacui et al. "Gamma Peptide Nucleic Acids: As Orthogonal Nucleic Acid Recognition Codes for Organizing Molecular Self-Assembly", Journal of the American Chemical Society, 2015, pp. 8603-8610, vol. 137.
Bahal, R., "Development of Conformationally Preorganized miniPEG-γPNA for Antigene and Antisense Applications", Doctoral Dissertation, Carnegie Mellon University, 2012, pp. 1-158.
Grossmann et al., "Nucleic Acid Templated Reactions: Consequences of Probe Reactivity and Readout Strategy for Amplified Signaling and Sequence Selectivity", Chem. Eur. J., 2009, pp. 6723-6730, vol. 15.
Napierala et al., "CUG Repeats in Myotonin Kinase RNA Form Metastable "Slippery" Hairpins", The Journal of Biological Chemistry, 1997, pp. 31079-31085, vol. 272, No. 49.

(Continued)

*Primary Examiner* — Ethan C Whisenant
(74) *Attorney, Agent, or Firm* — The Webb Law Firm

(57) ABSTRACT

Described herein are genetic recognition reagents comprising terminal aromatic moieties that bind specifically to a template nucleic acid and concatenate. Also provided are methods of using the genetic recognition reagents, e.g., to treat or diagnose a repeat expansion disorder, such as DM1.

20 Claims, 10 Drawing Sheets

Specification includes a Sequence Listing.

(56) References Cited

OTHER PUBLICATIONS

Thadke et al., "Shape selective bifacial recognition of double helical DNA", Communications Chemistry, 2018, pp. 1-10, vol. 1, No. 79.

Thadke et al., "Design of Bivalent Nucleic Acid Ligands for Recognition of RNA-Repeated Expansion Associated with Huntington's Disease", Biochemistry, 2018, pp. 2094-2108, vol. 57, No. 14.

Zhou et al., "Novel Binding and Efficient Cellular Uptake of Guanidine-Based Peptide Nucleic Acids (GPNA)", J. Am. Chem. Soc., 2003, pp. 6878-6879, vol. 125, No. 23.

\* cited by examiner

TEMPLATE-DIRECTED NUCLEIC ACID TARGETING COMPOUNDS

CROSS REFERENCE TO RELATED APPLICATIONS

This application is the United States national phase of International Application No. PCT/US2018/067096 filed Dec. 21, 2018, and claims priority to U.S. Provisional Application No. 62/708,789 filed Dec. 21, 2017, the disclosure of which are hereby incorporated by reference in their entirety.

STATEMENT REGARDING FEDERAL FUNDING

This invention was made with government support under Grant No. CHE1039870, awarded by the National Science Foundation and Grant No. R21NS098102 awarded by the National Institutes of Health. The government has certain rights in the invention.

The Sequence Listing associated with this application is filed in electronic format via EFS-Web and is hereby incorporated by reference into the specification in its entirety. The name of the text file containing the Sequence Listing is 6526_2003476_ST25.txt. The size of the text file is 673 bytes, and the text file was created on Jun. 16, 2020.

BACKGROUND

1. Field of the Invention

Described herein are compositions and methods of binding nucleic acids using nucleic acid and nucleic acid oligomer compositions. A method of treating repeat expansion disorders, such as myotonic dystrophy type 1 (DM1) and type 2 (DM2), also is provided.

2. Description of the Related Art

For most organisms, the genetic information is encoded in double-stranded DNA in the form of Watson-Crick base-pairing—in which adenine (A) pairs with thymine (T) and cytosine (C) with guanine (G). Depending on which set of this genetic information is decoded through transcription and translation, the developmental program and physiological status will be determined. Development of molecules that can be tailor-designed to bind sequence-specifically to any part of this genetic biopolymer, thereby enabling the control of the flow of genetic information and assessment and manipulation of the genome's structures and functions, is important for biological and biomedical research. This effort is also important for medicinal and therapeutic applications for the treatment and detection of genetic diseases.

Compared to proteins, RNA molecules are easier to target because they are made up of just four building blocks (A, C, G, U), whose interactions are defined by the well-established rules of Watson-Crick base-pairing. Compared to standard, double-stranded DNA (or RNA), the secondary structures of RNA are generally thermodynamically less stable and, thus, energetically less demanding for binding because, in addition to being canonical (perfectly-matched) base-pairs, many of them are noncanonical (mismatched) and contain single-stranded loops, bulges, and junctions. The presence of these local interacting domains is essential for 'tertiary' interactions and assembly of the secondary structures into compact three-dimensional shapes. As such, slight variations in the interaction patterns or bonding strengths within these regions will have a profound effect on the overall three-dimensional folding patterns of RNA. Thus, molecules that can be used to modulate RNA interactions and thereby interfere with the RNA folding behaviors are important as molecular tools for assessing RNA functions, as well as therapeutic and diagnostic reagents.

Genetic disorders generally occur as the result of an aberrant protein function due to mutation in the DNA coding sequence, or dysregulation at the transcriptional or translational level, resulting in the loss or gain of protein function. However, over the last three decades a preponderance of evidence has emerged showing that a large number of neuromuscular disorders, more than 20 in counting, including myotonic dystrophy type I (DMI) and type 2 (DM2), occur as the result of an unstable repeat expansion. An expansion in the coding region of a gene can lead to an altered protein function, whereas that occurring in the non-coding region can cause a disease without interfering with a protein sequence through toxic-gain of RNA function and, in certain cases, inadvertent production of deleterious polypeptides through repeat-associated non-ATG (RAN) translation.

A prototype of the latter class of genetic disorders is DMI, a debilitating muscular atrophy that affects one in every 8000 adults worldwide for which there is no effective treatment. DMJ is caused by a CTG-repeat expansion in the 3'-untranslated region (3'-UTR) of the dystrophia myotonica protein kinase (DMPK) gene, from a normal range of 5-35 repeats to a pathogenic range of 80 to >2500. The etiology of DMI is largely attributed to RNA toxicity. Upon transcription, the expanded rCUG-repeats ($rCUG^{exp}$) adopt an imperfect hairpin structure which sequesters the muscleblind-like protein I (MBNLI), a key RNA splicing regulator. Their association results in a $rCUG^{exp}$-MBNLI complex that is trapped in the nucleus, precluding its export to the cytoplasm for the production of DMPK protein, as well as in preventing MBNLI from carrying out its normal physiological function. Accumulated evidence has suggested that therapeutic intervention could be developed for DMI, and possibly for other related neuromuscular conditions as well, by targeting the mutant transcript. The challenge, however, is in how to design molecules that would target the expanded transcripts without interfering with the wildtype (wt), and that would be able to displace the non-cognate proteins such as MBNLI from $rCUG^{exp}$.

Pursuit of this goal has led to the development of several classes of molecules for targeting $rCUG^{exp}$, including pentamidines, triaminotriazines, and peptidomimetics. Recently, Disney and coworkers reported the development of modular peptoids, as well as the identification of several small molecules with high affinity and potency. The antisense approach, utilizing morpholino and 2'-O-methoxyethyl gapmer, has also been explored and has been shown to be effective in disrupting the $rCUG^{exp}$-MBNLI complex and in degrading the toxic RNA, and in reversing the DMI phenotypes in an animal model. More recently, antigene strategy directed at modification of the affected alleles, employing TALEN and CRISPR/Cas9, has been investigated as a possible remedy for DMI and related medical conditions. Despite the promising outlook, considerable challenge associated with recognition specificity and/or selectivity, and cellular delivery, to a certain extent, remains for many of these classes of designer molecules—particularly, antisense agents. The low to moderate affinity, along with the lack of substantial binding cooperativity, of most synthetic oligonucleotide molecules developed to date have prevented the application of shorter probes for greater ease of cellular delivery and for better discrimination of the expanded (diseased) RNA-repeated transcripts from the wt.

Nucleic acid interactions, such as RNA-RNA and RNA-protein interactions play key roles in gene regulation, including replication, translation, folding and packaging. The ability to selectively bind to these perturbed regions within the secondary structures of RNA is important in manipulating their physiological functions. As such, improved reagents and methods capable of selectively binding nucleic acids are desired.

SUMMARY OF THE INVENTION

In one aspect, a genetic recognition reagent is provided. The genetic recognition reagent comprises: a nucleic acid or nucleic acid analog backbone, having a first end and a second end, and having from three to eight ribose, deoxyribose, or nucleic acid analog backbone residues; nucleobases, that may be the same or different, linked in a sequence complementary to a target nucleic acid to a plurality of the ribose, deoxyribose, or nucleic acid analog backbone residues; a first aryl moiety linked by a linker to the first end of the nucleic acid or nucleic acid analog backbone; and a second aryl moiety that is optionally the same as the first aryl moiety, linked by a linker to the second end of the of the nucleic acid or nucleic acid analog backbone, wherein the aryl moieties stack with aryl moieties of an adjacent recognition reagent when recognition reagents are hybridized to adjacent sequences of a target nucleic acid. A composition comprising the genetic recognition reagent and a pharmaceutically-acceptable carrier also is provided.

In another aspect, a method of binding a nucleic acid in a cell is provided, comprising contacting a target sequence of the mRNA with a genetic recognition reagent comprising a nucleic acid or nucleic acid analog backbone, having a first end and a second end, and having from three to eight ribose, deoxyribose, or nucleic acid analog backbone residues; nucleobases, that may be the same or different, linked in a sequence complementary to a target nucleic acid to a plurality of the ribose, deoxyribose, or nucleic acid analog backbone residues; a first aryl moiety linked by a linker to the first end of the nucleic acid or nucleic acid analog backbone; and a second aryl moiety that is optionally the same as the first aryl moiety, linked by a linker to the second end of the of the nucleic acid or nucleic acid analog backbone, wherein the aryl moieties stack with aryl moieties of an adjacent recognition reagent when recognition reagents are hybridized to adjacent sequences of a target nucleic acid, and having a nucleobase sequence complementary to the target sequence.

In another aspect, a method of knocking down expression of an mRNA in a cell is provided, comprising contacting a target sequence of the mRNA with a genetic recognition reagent comprising a nucleic acid or nucleic acid analog backbone, having a first end and a second end, and having from three to eight ribose, deoxyribose, or nucleic acid analog backbone residues; nucleobases, that may be the same or different, linked in a sequence complementary to a target nucleic acid to a plurality of the ribose, deoxyribose, or nucleic acid analog backbone residues; a first aryl moiety linked by a linker to the first end of the nucleic acid or nucleic acid analog backbone; and a second aryl moiety that is optionally the same as the first aryl moiety, linked by a linker to the second end of the of the nucleic acid or nucleic acid analog backbone, wherein the aryl moieties stack with aryl moieties of an adjacent recognition reagent when recognition reagents are hybridized to adjacent sequences of a target nucleic acid, and having a nucleobase sequence complementary to the target sequence.

In another aspect, a method of identifying a target sequence of a nucleic acid in a sample is provided. The method comprises: contacting a sample comprising nucleic acid with a genetic recognition reagent comprising a nucleic acid or nucleic acid analog backbone, having a first end and a second end, and having from three to eight ribose, deoxyribose, or nucleic acid analog backbone residues; nucleobases, that may be the same or different, linked in a sequence complementary to a target nucleic acid to a plurality of the ribose, deoxyribose, or nucleic acid analog backbone residues; a first aryl moiety linked by a linker to the first end of the nucleic acid or nucleic acid analog backbone; and a second aryl moiety that is optionally the same as the first aryl moiety, linked by a linker to the second end of the of the nucleic acid or nucleic acid analog backbone, wherein the aryl moieties stack with aryl moieties of an adjacent recognition reagent when recognition reagents are hybridized to adjacent sequences of a target nucleic acid, in which the aryl moieties produce a first fluorescent emission when exposed to an excitation frequency of light when not concatenated on a target sequence, and a second fluorescent emission different from the first fluorescent emission when exposed to an excitation frequency of light when concatenated on a target sequence, and determining the presence of the target sequence in the sample by exciting the fluorescent aromatic moieties and measuring the amount of the second fluorescent signal produced in the sample by the fluorescent aromatic moieties.

¼, T6=⅙, T8 ⅛) following the incubation at 37° C. for 1 hr and excitation at 345 nm. Inset: Fluorescent signals at 480 nm as a function of time following the addition of P4 (1 µM) to T8 (⅛ µM), and P4 (1 µM) to [T1 (1 µM)+T8 (⅛ µM)] at 37° C.

Figure 10:
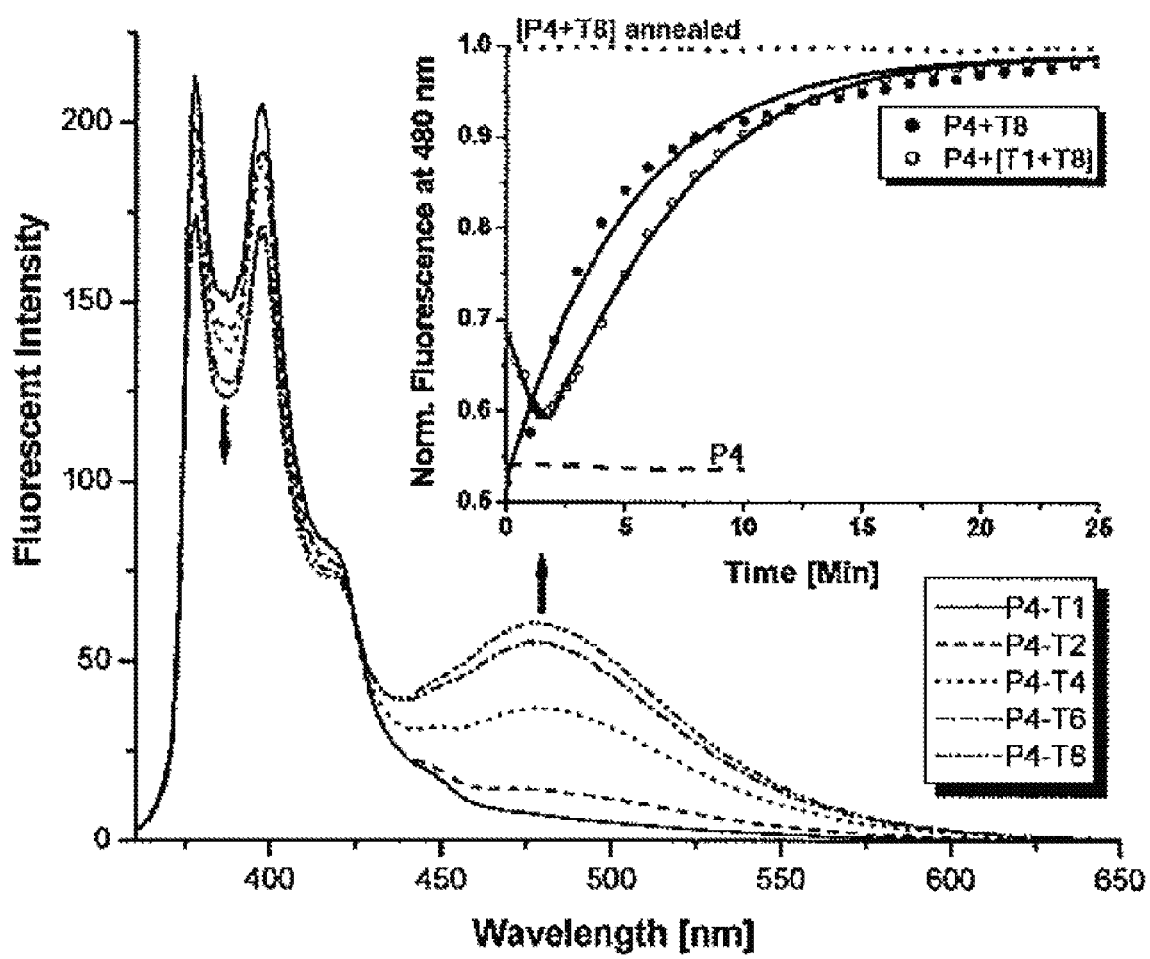
FIG. 10. Fluorescent spectra of P4-RNA duplexes at equimolar concentrations (P4=1 µM; T1=1 µM, T2=½, T4
Figure 11:
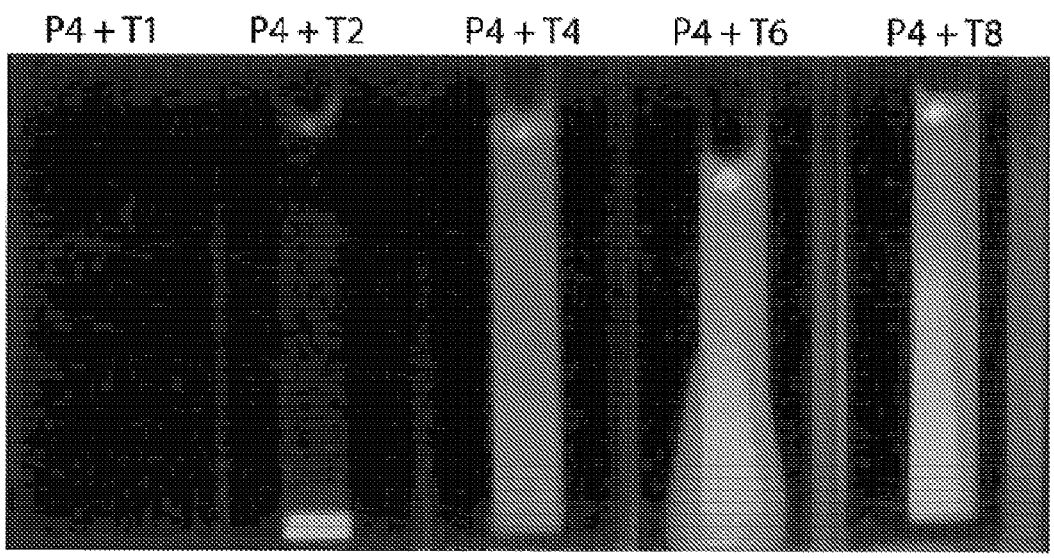

FIG. 11. Photograph of the samples used in the fluorescent measurements as shown in FIG. 10 upon illumination with a hand-held UV-lamp. The concentrations of the individual components were as followed: P4=1 µM; T1=1 µM, T2=½ µM, T4=¼ µM, T6=⅙ µM, and T8=⅛ µM.

Figure 12:
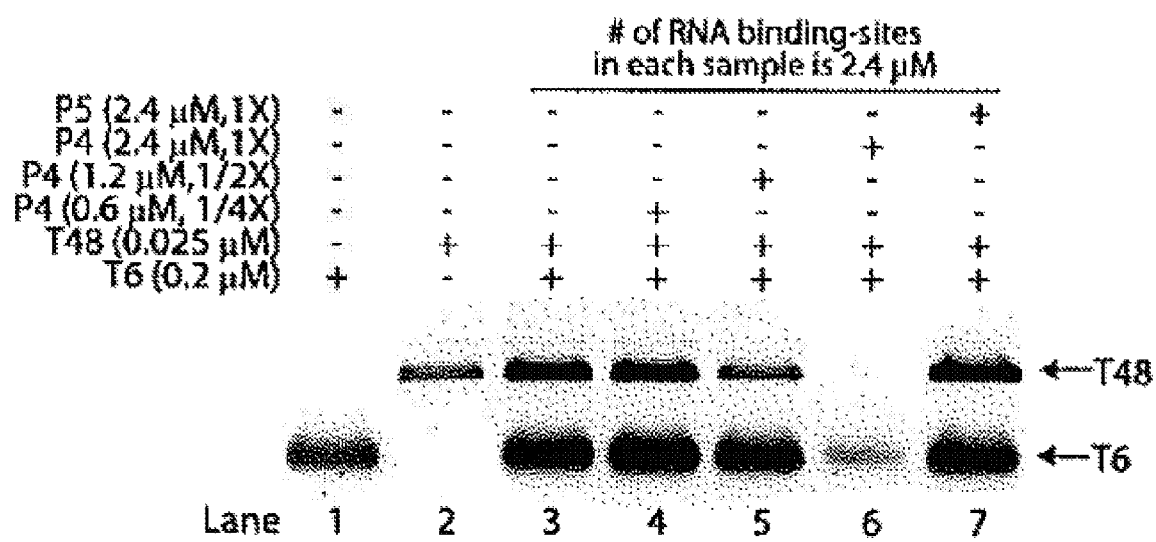

FIG. 12. Selective binding of r(CUGCUG)$_n$-RNA transcripts by P4. The samples were prepared by mixing pre-annealed RNAs with probes at 37° C. for 4 hrs. The ratios of P4 to the total RNA binding-sites were 0 (lane 3), ¼ (lane 4), ½ (lane 5), 1/1 (lane 6); and for the mismatched P5 at 1/1 (lane 7).

Figure 13:
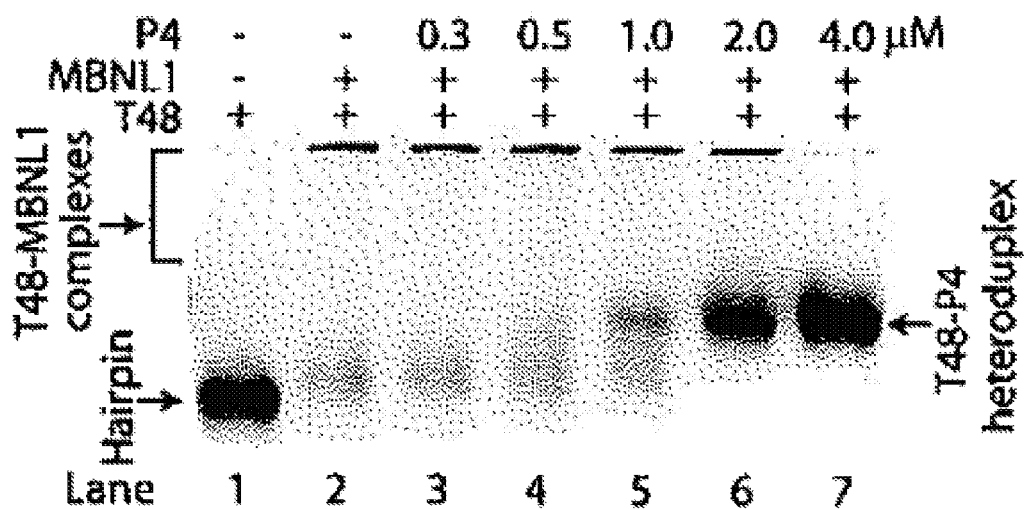

FIG. 13. Displacement of MBNL$_1$ from T48 by P4. P-T48 was allowed to form complexes with GST-MBNL$_1$-Fl prior to the addition of P4. The samples were prepared in a physiologically relevant buffer at the final T48 and GST-MBNL$_1$-Fl concentration of 25 nM and 400 nM, respectively.

DETAILED DESCRIPTION

The use of numerical values in the various ranges specified in this application, unless expressly indicated otherwise, are stated as approximations as though the minimum and maximum values within the stated ranges are both preceded by the word "about". In this manner, slight variations above and below the stated ranges can be used to achieve substantially the same results as values within the ranges. Also, unless indicated otherwise, the disclosure of ranges is intended as a continuous range including every value between the minimum and maximum values. As used herein "a" and "an" refer to one or more.

As used herein, the term "comprising" is open-ended and may be synonymous with "including", "containing", or "characterized by". The term "consisting essentially of" limits the scope of a claim to the specified materials or steps and those that do not materially affect the basic and novel characteristic(s) of the claimed invention. The term "consisting of" excludes any element, step, or ingredient not specified in the claim. As used herein, embodiments "comprising" one or more stated elements or steps also include, but are not limited to embodiments "consisting essentially of" and "consisting of" these stated elements or steps.

Figure 1:
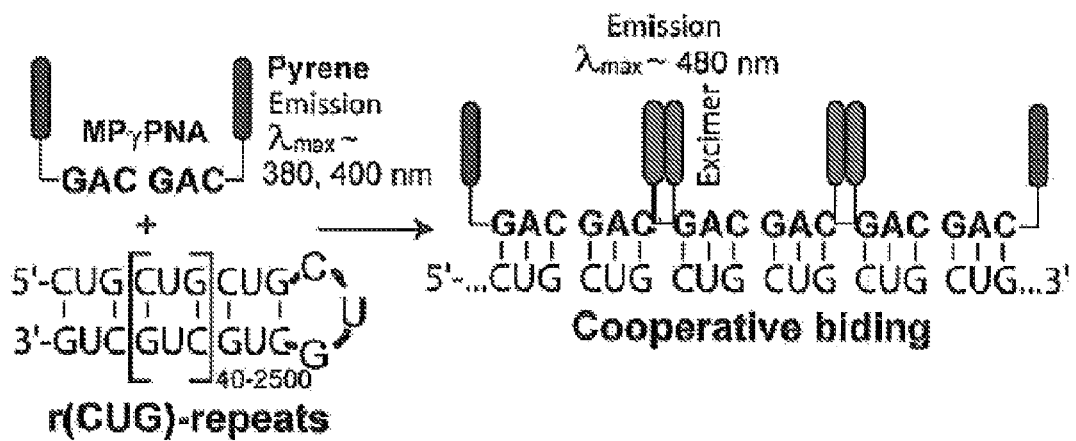
FIG. 1 is a schematic diagram illustrating the cooperative binding of a non-limiting example of the genetic recognition reagents described herein. The sequence of the genetic recognition reagent is depicted in a 3' to 5' direction to depict binding to the repeat-containing RNA (SEQ ID NO: 1).

Provided herein are compositions and methods for binding target sequences in nucleic acids, for example for binding repeat expansions associated with diseases involving repeat expansions of nucleic acid sequences. FIG. 1 is a schematic diagram illustrating the cooperative binding of a non-limiting example of the recognition reagents (genetic recognition reagents) described herein, targeting CUG repeats in RNA hairpin structures as seen in DM1. Cooperative binding of modules to adjacent modules is facilitated in this example by the terminal aromatic groups, such as the exemplary pyrene groups described in the Example, below, which emit at 380 nm and 480 nm when not stacked, and at 480 nm when stacked. The plurality of recognition reagents bind by Watson-Crick or Watson-Crick-like cooperative base pairing to a template nucleic acid. In a cell a template nucleic acid is an RNA or DNA molecule, though in vitro, a template nucleic acid can be any RNA or DNA, as well as a modified nucleic acid or a nucleic acid analog. Recognition reagents in sufficient proximity, for example binding to adjacent sequences on a template nucleic acid, will concatenate, via π-π stacking, thus concatenating to essentially form a longer oligomer or polymer. Further details are provided below.

As used herein, a "patient" is an animal, such as a mammal, including a primate (such as a human, a non-human primate, e.g., a monkey, and a chimpanzee), a non-primate (such as a cow, a pig, a camel, a llama, a horse, a goat, a rabbit, a sheep, a hamster, a guinea pig, a cat, a dog, a rat, a mouse, a horse, and a whale), or a bird (e.g., a duck or a goose).

As used herein, the terms "treating", or "treatment" refer to a beneficial or desired result, such as improving one of more liver functions, or symptoms of a disease. The terms "treating" or "treatment" also include, but are not limited to, alleviation or amelioration of one or more symptoms of a repeat expansion disease, such as DM1, DM2, or Huntington's Disease. "Treatment" can also mean prolonging survival as compared to expected survival in the absence of treatment.

By "lower" in the context of a disease marker or symptom is meant a clinically-relevant and/or a statistically significant decrease in such level. The decrease can be, for example, at least 10%, at least 20%, at least 30%, at least 40%, or more, down to a level accepted as within the range of normal for an individual without such disorder, or to below the level of detection of the assay. In certain aspects, the decrease is down to a level accepted as within the range of normal for an individual without such disorder which can also be referred to as a normalization of a level. In certain aspects, the reduction is the normalization of the level of a sign or symptom of a disease, a reduction in the difference between the subject level of a sign of the disease and the normal level of the sign for the disease (e.g., to the upper level of normal when the value for the subject must be decreased to reach a normal value, and to the lower level of normal when the value for the subject must be increased to reach a normal level). In certain aspects, the methods include a clinically relevant inhibition of expression of a mRNA of a repeat expansion disease, such as DM1, DM2, or Huntington's Disease, e.g., as demonstrated by a clinically relevant outcome after treatment of a subject with a recognition reagent as described herein.

"Therapeutically effective amount," as used herein, is intended to include the amount of a recognition reagent as described herein that, when administered to a subject having a disease, is sufficient to effect treatment of the disease (e.g., by diminishing, ameliorating or maintaining the existing disease or one or more symptoms of disease). The "therapeutically effective amount" may vary depending on the recognition reagent (agent), how the agent is administered, the disease and its severity and the history, age, weight, family history, genetic makeup, the types of preceding or concomitant treatments, if any, and other individual characteristics of the subject to be treated.

A "therapeutically-effective amount" also includes an amount of an agent that produces some desired local or systemic effect at a reasonable benefit/risk ratio applicable to any treatment. Recognition reagent agents employed in the methods described herein may be administered in a sufficient amount to produce a reasonable benefit/risk ratio applicable to such treatment.

The phrase "pharmaceutically-acceptable carrier" as used herein means a pharmaceutically-acceptable material, composition or vehicle, such as a liquid or solid filler, diluent, excipient, manufacturing aid (e.g., lubricant, talc magnesium, calcium or zinc stearate, or steric acid), or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the subject being treated. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) lubricating agents, such as magnesium state, sodium lauryl sulfate and talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; (22) bulking agents, such as polypeptides and amino acids (23) serum component, such as serum albumin, HDL and LDL; and (22) other non-toxic compatible substances employed in pharmaceutical formulations.

As used herein, the terms "cell" and "cells" refer to any types of cells from any animal, such as, without limitation, rat, mice, monkey, and human. For example and without limitation, cells can be progenitor cells, such as stem cells, or differentiated cells, such as endothelial cells, smooth muscle cells. In certain embodiments, cells for medical procedures can be obtained from the patient for autologous procedures or from other donors for allogeneic procedures.

By "expression" or "gene expression," it is meant the overall flow of information from a gene (without limitation, a functional genetic unit for producing a gene product, such as RNA or a protein in a cell, or other expression system encoded on a nucleic acid and comprising: a transcriptional promoter and other cis-acting elements, such as response elements and/or enhancers; an expressed sequence that typically encodes a protein (open-reading frame or ORF) or functional/structural RNA, and a polyadenylation sequence), to produce a gene product (typically a protein, optionally post-translationally modified or a functional/ structural RNA). By "expression of genes under transcriptional control of," or alternately "subject to control by," a designated sequence, it is meant gene expression from a gene containing the designated sequence operably linked (functionally attached, typically in cis) to the gene. The designated sequence may be all or part of the transcriptional elements (without limitation, promoters, enhancers and response elements), and may wholly or partially regulate and/or affect transcription of a gene. A "gene for expression of" a stated gene product is a gene capable of expressing that stated gene product when placed in a suitable environment—that is, for example, when transformed, transfected, transduced, etc. into a cell, and subjected to suitable conditions for expression. In the case of a constitutive promoter "suitable conditions" means that the gene typically need only be introduced into a host cell. In the case of an inducible promoter, "suitable conditions" means when an amount of the respective inducer is administered to the expression system (e.g., cell) effective to cause expression of the gene.

As used herein, the term "knockdown" means that expression of one or more genes in an organism is reduced, typically significantly, with respect to a functional gene, such as to a therapeutically-effective degree. Gene knockdown also includes complete gene silencing. As used herein, "gene silencing" means that expression of a gene is essentially completely prevented. Knockdown and gene silencing may occur either at the transcriptional stage or the translational stage. Use of the described recognition reagents to target an RNA in a cell, such as an mRNA, can modify gene expression, by knocking down or silencing a gene or genes at the translational stage.

As used herein, the term "nucleic acid" refers to deoxyribonucleic acids (DNA) and ribonucleic acids (RNA). Nucleic acid analogs include, for example and without limitation: 2'-O-methyl-substituted RNA, locked nucleic acids, unlocked nucleic acids, triazole-linked DNA, peptide nucleic acids, morpholino oligomers, dideoxynucleotide oligomers, glycol nucleic acids, threose nucleic acids and combinations thereof including, optionally ribonucleotide or deoxyribonucleotide residue(s). Herein, "nucleic acid" and "oligonucleotide" which is a short, single-stranded structure made of up nucleotides, in reference to nucleic acids and nucleic acid analogs, are used interchangeably. An oligonucleotide may be referred to by the length (i.e. number of nucleotides) of the strand, through the nomenclature "-mer". For example, an oligonucleotide of 22 nucleotides would be referred to as a 22-mer.

A "nucleic acid analog" is a composition comprising a sequence of nucleobases arranged on a substrate, such as a polymeric backbone, and can bind DNA and/or RNA by hybridization by Watson-Crick, or Watson-Crick-like hydrogen bond base pairing. Non-limiting examples of common nucleic acid analogs include peptide nucleic acids, such as γPNA, morpholino nucleic acids, phosphorothioates, locked nucleic acid (2'-O-4'-C-methylene bridge, including oxy, thio or amino versions thereof), unlocked nucleic acid (the C2'-C3' bond is cleaved), 2'-O-methyl-substituted RNA, threose nucleic acid, glycol nucleic acid, etc.

A conformationally preorganized nucleic acid analog is a nucleic acid analog that has a backbone (a preorganized backbone) that forms only either a right-handed helix or a left-handed helix, depending on the structure of the nucleic acid backbone. As shown herein, one example of a conformationally preorganized nucleic acid analog is γPNA, which has a chiral center at the γ carbon, and, depending on, and due to, the chirality of the groups at the γ carbon, forms only a right-handed helix or a left-handed helix. Likewise, locked nucleic acid, comprising a ribose with a bridge between the 2' oxygen and the 4' carbon, that "locks" the ribose into a 3'-endo (North) conformation.

In the context of the present disclosure, a "nucleotide" refers to a monomer comprising at least one nucleobase and a backbone element (backbone moiety), which in a nucleic acid, such as RNA or DNA is ribose or deoxyribose. "Nucleotides" also typically comprise reactive groups that permit polymerization under specific conditions. In native DNA and RNA, those reactive groups are the 5' phosphate and 3' hydroxyl groups. For chemical synthesis of nucleic acids and analogs thereof, the bases and backbone monomers may contain modified groups, such as blocked amines, as are known in the art. A "nucleotide residue" refers to a single nucleotide that is incorporated into an oligonucleotide or polynucleotide. Likewise, a "nucleobases residue" refers to a nucleobases incorporated into a nucleotide or a nucleic acid or analog thereof. A "genetic recognition reagent" refers generically to a nucleic acid or a nucleic acid analog that comprises a sequence of nucleobases that is able to hybridize to a complementary nucleic acid or nucleic acid analog sequence on a nucleic acid by cooperative base pairing, e.g., Watson-Crick base pairing or Watson-Crick-like base pairing.

In further detail, nucleotides, for either RNA, DNA, or nucleic acid analogs, have the structure A-B wherein A is a backbone monomer moiety and B is a nucleobase as described herein. The backbone monomer can be any suitable nucleic acid backbone monomer, such as a ribose triphosphate or deoxyribose triphosphate, or a monomer of a nucleic acid analog, such as peptide nucleic acid (PNA), such as a gamma PNA (γPNA). In one example the backbone monomer is a ribose mono-, di-, or tri-phosphate or a deoxyribose mono-, di-, or tri-phosphate, such as a 5' monophosphate, diphosphate, or triphosphate of ribose or deoxyribose. The backbone monomer includes both the structural "residue" component, such as the ribose in RNA, and any active groups that are modified in linking monomers together, such as the 5' triphosphate and 3' hydroxyl groups of a ribonucleotide, which are modified when polymerized into RNA to leave a phosphodiester linkage. Likewise for PNA, the C-terminal carboxyl and N-terminal amine active groups of the N-(2-aminoethyl)glycine backbone monomer are condensed during polymerization to leave a peptide (amide) bond. In another aspect, the active groups are phosphoramidite groups useful for phosphoramidite oligomer synthesis, as is broadly-known in the arts. The nucleotide also optionally comprises one or more protecting groups as are known in the art, such as 4,4'-dimethoxytrityl (DMT), and as described herein. A number of additional methods of preparing synthetic genetic recognition reagents are known, and depend on the backbone structure and particular chemistry of the base addition process. Determination of which active groups to utilize in joining nucleotide monomers and which groups to protect in the bases, and the required steps in preparation of oligomers is well within the abilities of those of ordinary skill in the chemical arts and in the field of nucleic acid and nucleic acid analog oligomer synthesis.

Figure 2:
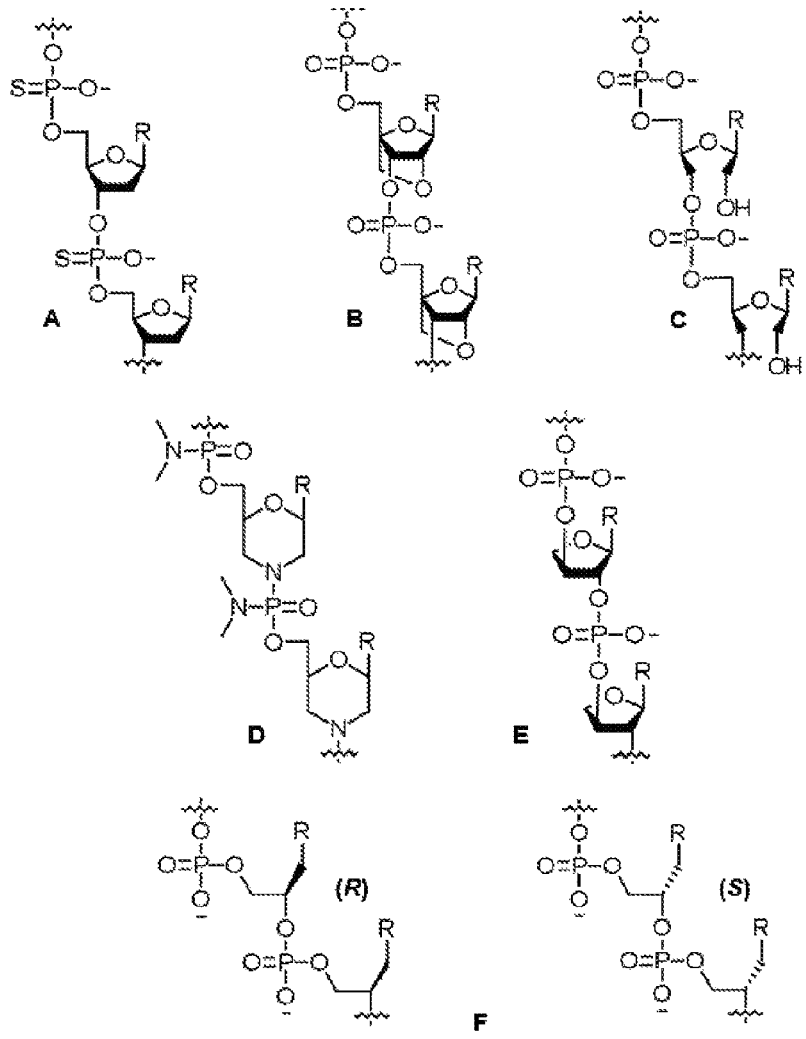
FIG. 2 (A-F) provides exemplary structures of nucleic acid analogs.
Figure 3:
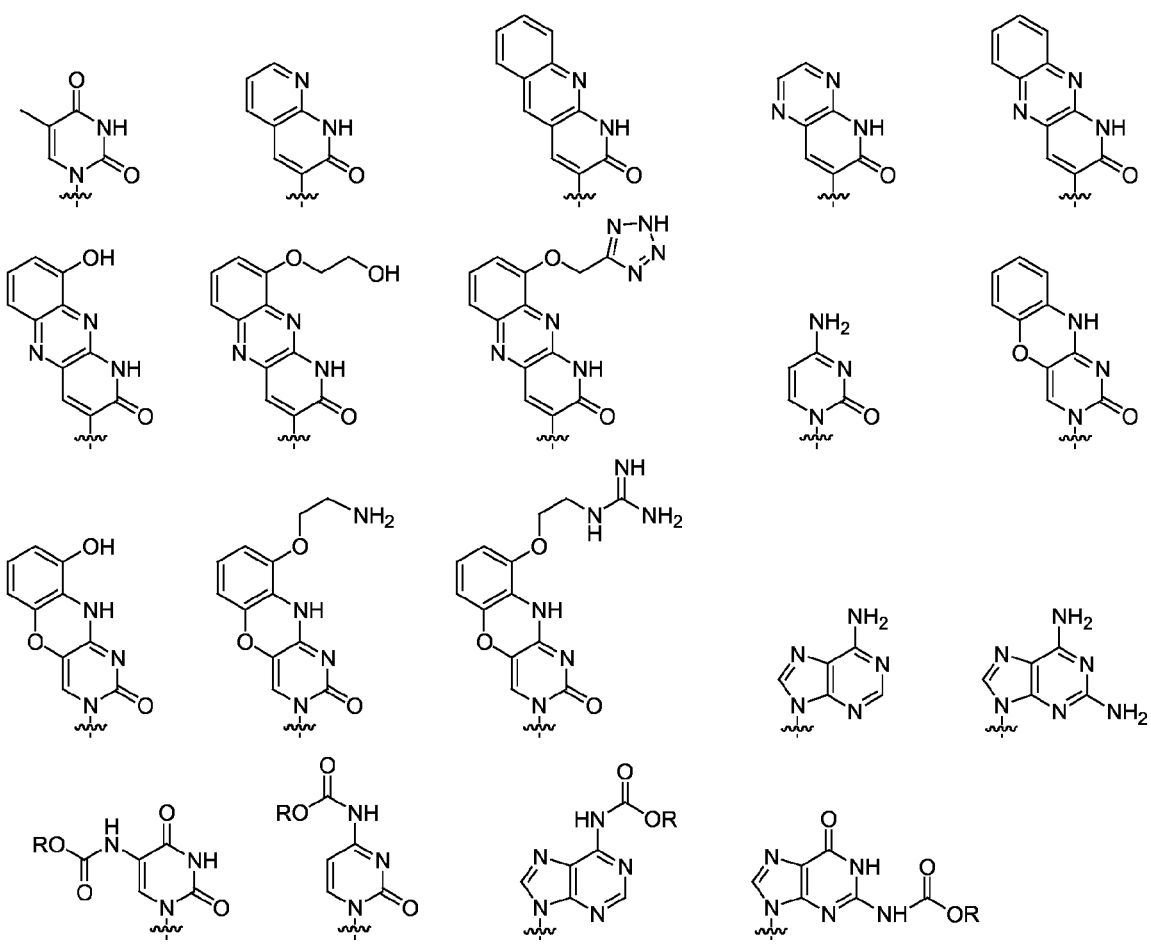
FIG. 3 provides structures of exemplary nucleobases.
Figure 4A:
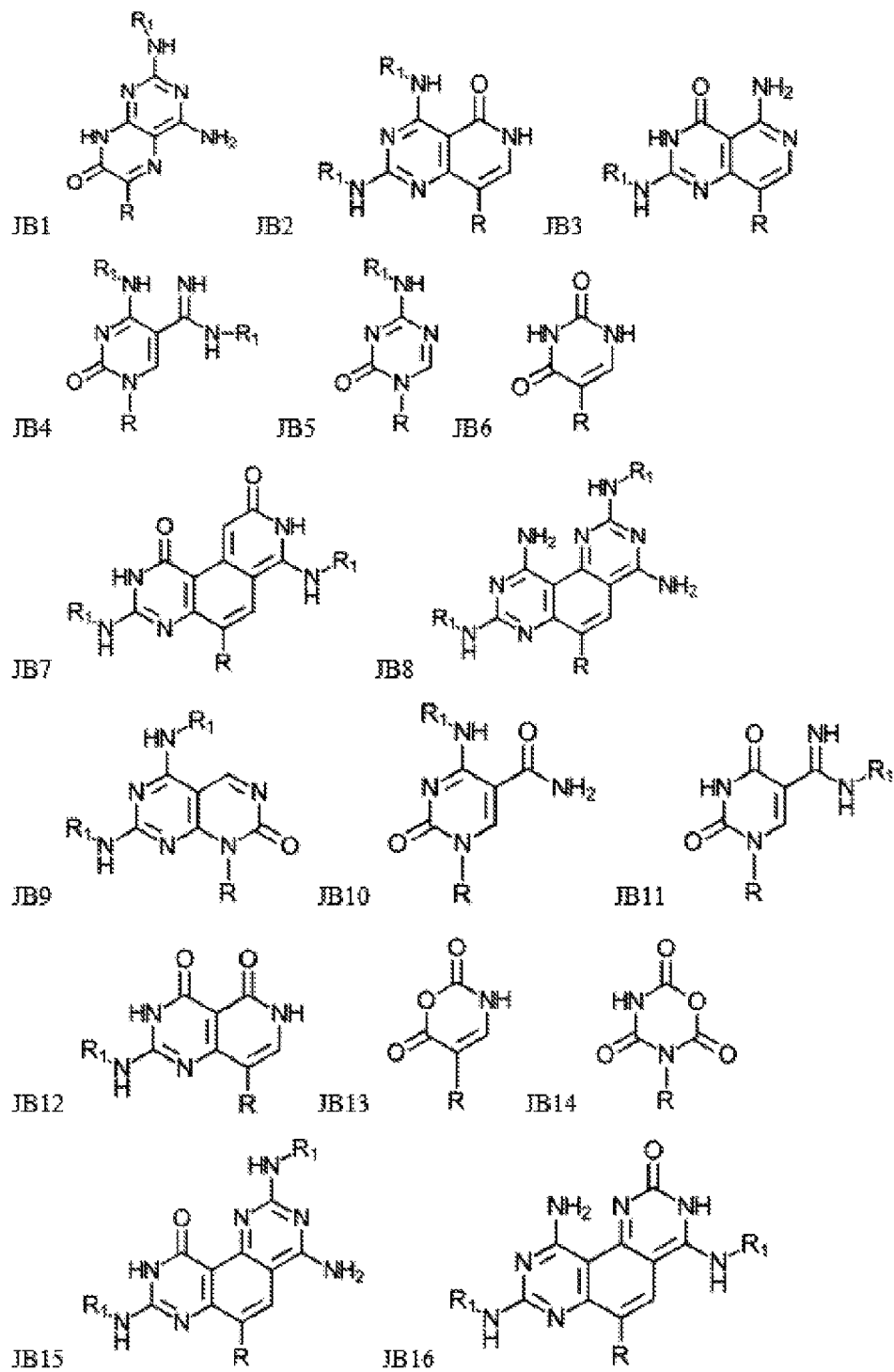
FIGS. 4A-4C provide structures of exemplary divalent nucleobases.
Figure 4B:
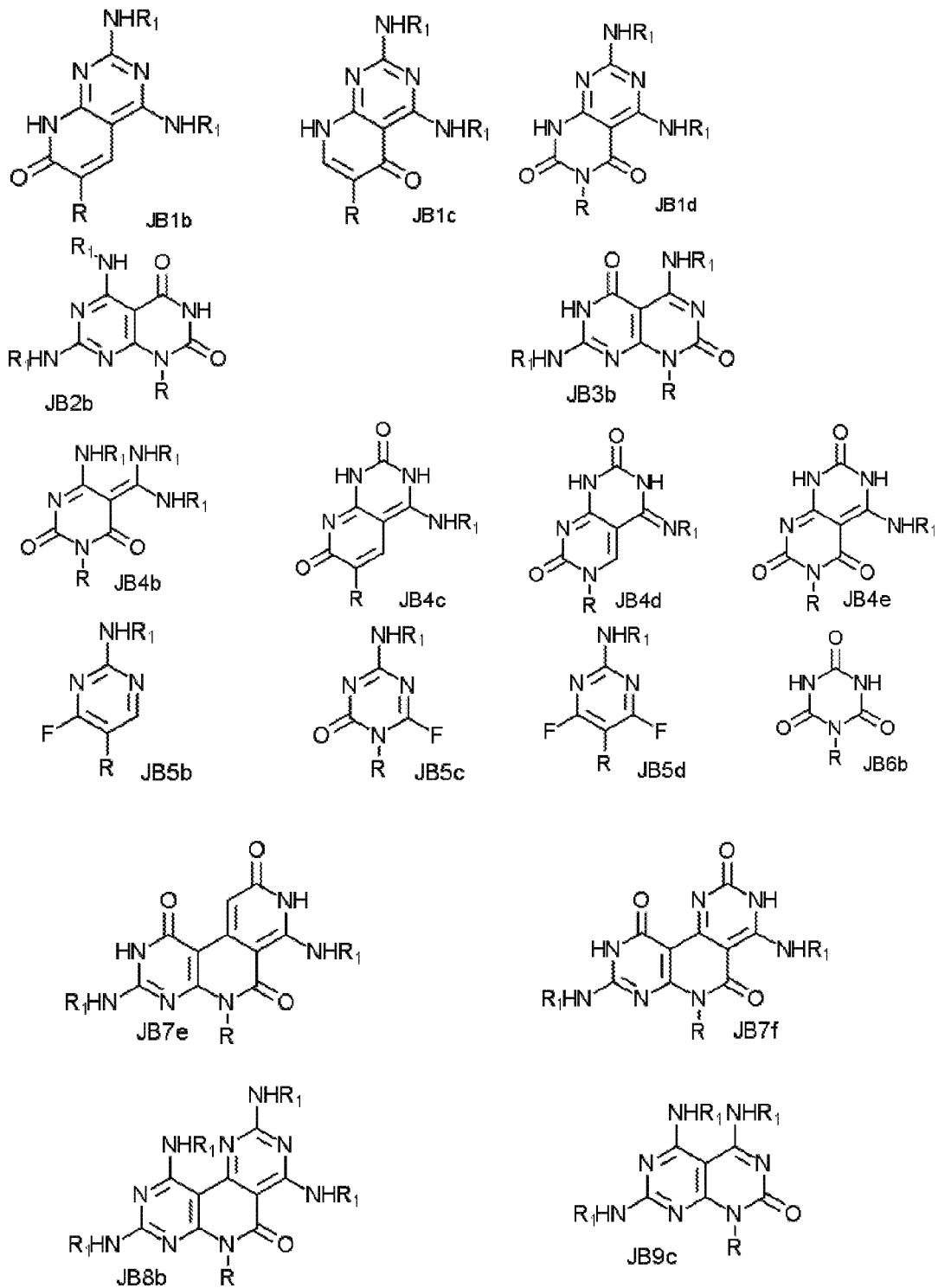
Figure 4C:
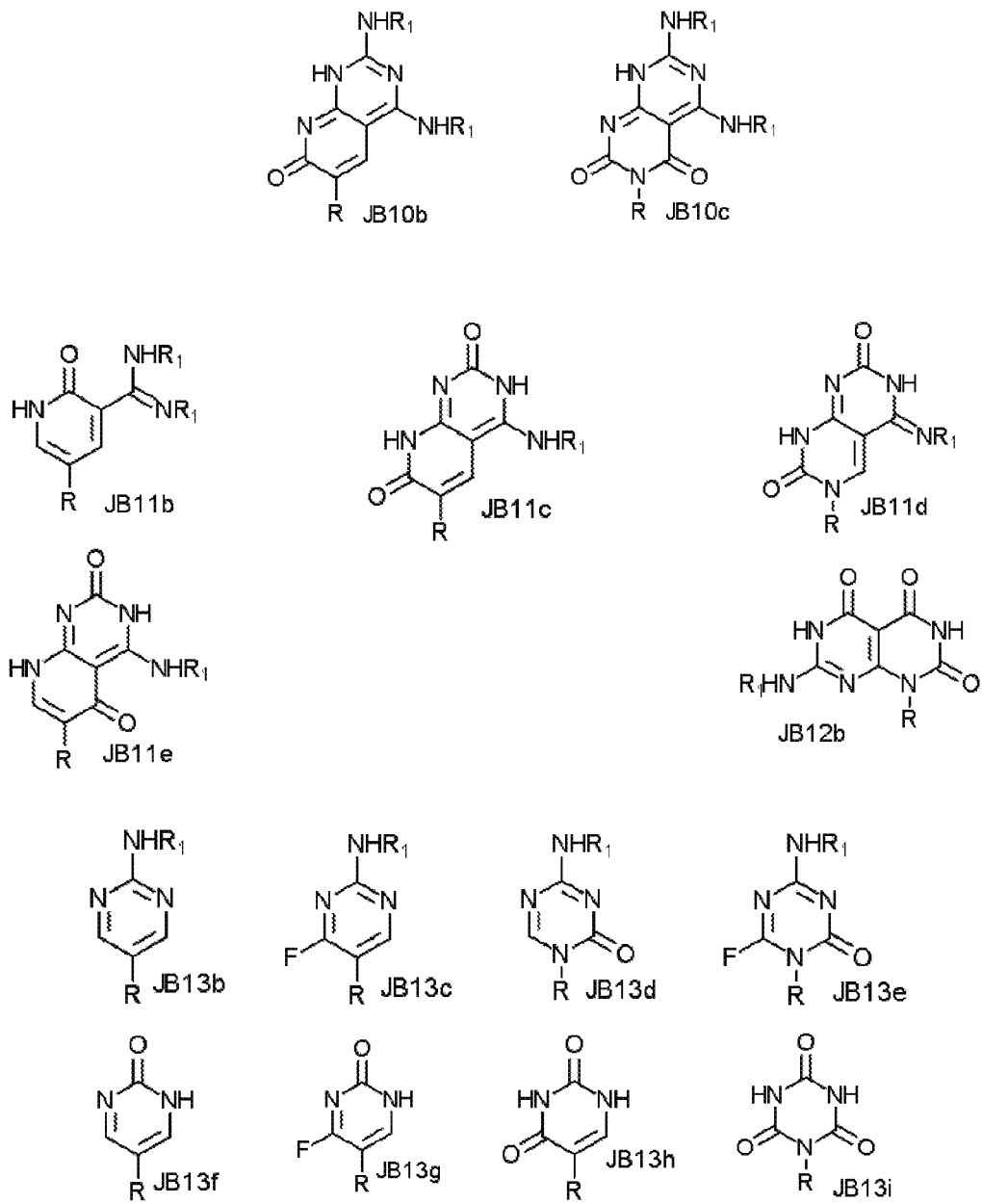

Non-limiting examples of common nucleic acid analogs include peptide nucleic acids, such as γPNA, phosphorothioate (e.g., FIG. 2(A)), locked nucleic acid (2'-O-4'-C-methylene bridge, including oxy, thio or amino versions thereof, e.g., FIG. 2(B)), unlocked nucleic acid (the C2'-C3' bond is cleaved, e.g., FIG. 2(C)), 2'-O-methyl-substituted RNA, morpholino nucleic acid (e.g., FIG. 2(D)), threose nucleic acid (e.g., FIG. 2(E)), glycol nucleic acid (e.g., FIG. 2(F), showing R and S Forms), etc. FIG. 2(A-F) shows monomer structures for various examples of nucleic acid analogs. FIG. 2(A-F) each show two monomer residues incorporated into a longer chain as indicated by the wavy lines. Incorporated monomers are referred to herein as "residues" and the part of the nucleic acid or nucleic acid analog excluding the nucleobases is referred to as the "backbone" of the nucleic acid or nucleic acid analog. As an example, for RNA, an exemplary nucleobase is adenine, a corresponding monomer is adenosine triphosphate, and the incorporated residue is an adenosine monophosphate residue. For RNA, the "backbone" consists of ribose subunits linked by phosphates, and thus the backbone monomer is ribose triphosphate prior to incorporation and a ribose monophosphate residue after incorporation. Like γPNA, Locked Nucleic Acid (FIG. 2(B)) is conformationally pre-organized.

A "moiety" is a part of a molecule, and includes as a class "residues", which are the portion of a compound or monomer that remains in a larger molecule, such as a polymer chain, after incorporation of that compound or monomer into the larger molecule, such as a nucleotide as-incorporated into a nucleic acid or an amino acid as-incorporated into a polypeptide or protein.

The term "polymer composition" is a composition comprising one or more polymers. As a class, "polymers" includes, without limitation, homopolymers, heteropolymers, co-polymers, block polymers, block co-polymers and can be both natural and synthetic. Homopolymers contain one type of building block, or monomer, whereas co-polymers contain more than one type of monomer. An "oligomer" is a polymer that comprises a small number of monomers, such as, for example, from 3 to 100 monomer residues. As such, the term "polymer" includes oligomers. The terms "nucleic acid" and "nucleic acid analog" includes nucleic acid and nucleic acid polymers and oligomers.

A polymer "comprises" or is "derived from" a stated monomer if that monomer is incorporated into the polymer. Thus, the incorporated monomer that the polymer comprises is not the same as the monomer prior to incorporation into a polymer, in that at the very least, certain linking groups are incorporated into the polymer backbone or certain groups are removed in the polymerization process. A polymer is said to comprise a specific type of linkage if that linkage is present in the polymer. An incorporated monomer is a "residue". A typical monomer for a nucleic acid or nucleic acid analog is referred to as a nucleotide.

By "non-reactive", in the context of a chemical constituent, such as a molecule, compound, composition, group, moiety, ion, etc. it is meant that the constituent does not react with other chemical constituents in its intended use to any substantial extent. The non-reactive constituent is selected to not interfere, or to interfere insignificantly, with the intended use of the constituent, moiety, or group as a recognition reagent. In the context of the linker moieties described herein, they are non-reactive in that they do not interfere with the binding of the recognition reagents to a target template, and do not interfere with concatenation of the recognition reagents on the target template.

As used herein, "alkyl" refers to straight, branched chain, or cyclic hydrocarbon groups including, for example, from 1 to about 20 carbon atoms, for example and without limitation $C_{1-3}$, $C_{1-6}$, $C_{1-10}$ groups, for example and without limitation, straight, branched chain alkyl groups such as methyl, ethyl, propyl, butyl, pentyl, hexyl, heptyl, octyl, nonyl, decyl, undecyl, dodecyl, and the like. "Substituted alkyl" refers to alkyl substituted at 1 or more, e.g., 1, 2, 3, 4, 5, or even 6 positions, which substituents are attached at any available atom to produce a stable compound, with substitution as described herein. "Optionally substituted alkyl" refers to alkyl or substituted alkyl. "Halogen," "halide," and "halo" refers to —F, —Cl, —Br, and/or —I. "Alkylene" and "substituted alkylene" refer to divalent alkyl and divalent substituted alkyl, respectively, including, without limitation, methylene, ethylene, trimethylene, tetramethylene, pentamethylene, hexamethylene, heptamethylene, octamethylene, nona methylene, or decamethylene. "Optionally substituted alkylene" refers to alkylene or substituted alkylene.

"Alkene or alkenyl" refers to straight, branched chain, or cyclic hydrocarbyl groups including, e.g., from 2 to about 20 carbon atoms, such as, without limitation $C_{1-3}$, $C_{1-6}$, $C_{1-10}$ groups having one or more, e.g., 1, 2, 3, 4, or 5, carbon-to-carbon double bonds. "Substituted alkene" refers to alkene substituted at 1 or more, e.g., 1, 2, 3, 4, or 5 positions, which substituents are attached at any available atom to produce a stable compound, with substitution as described herein. "Optionally substituted alkene" refers to alkene or substituted alkene. Likewise, "alkenylene" refers to divalent alkene. Examples of alkenylene include without limitation, ethenylene (—CH=CH—) and all stereoisomeric and conformational isomeric forms thereof. "Substituted alkenylene" refers to divalent substituted alkene. "Optionally substituted alkenylene" refers to alkenylene or substituted alkenylene.

"Alkyne" or "alkynyl" refers to a straight or branched chain unsaturated hydrocarbon having the indicated number of carbon atoms and at least one triple bond. Examples of a ($C_2$-$C_8$)alkynyl group include, but are not limited to, acetylene, propyne, 1-butyne, 2-butyne, 1-pentyne, 2-pentyne, 1-hexyne, 2-hexyne, 3-hexyne, 1-heptyne, 2-heptyne, 3-heptyne, 1-octyne, 2-octyne, 3-octyne and 4-octyne. An alkynyl group can be unsubstituted or optionally substituted with one or more substituents as described herein below. The term "alkynylene" refers to divalent alkyne. Examples of alkynylene include without limitation, ethynylene, propynylene. "Substituted alkynylene" refers to divalent substituted alkyne.

The term "alkoxy" refers to an —O-alkyl group having the indicated number of carbon atoms. For example, a ($C_1$-$C_6$)alkoxy group includes —O-methyl (methoxy), —O-ethyl (ethoxy), —O-propyl (propoxy), —O-isopropyl (isopropoxy), —O-butyl (butoxy), —O-sec-butyl (sec-butoxy), —O-tert-butyl (tert-butoxy), —O-pentyl (pentoxy), —O-isopentyl (isopentoxy), —O-neopentyl (neopentoxy), —O-hexyl (hexyloxy), —O-isohexyl (isohexyloxy), and —O-neohexyl (neohexyloxy). "Hydroxyalkyl" refers to a ($C_1$-$C_{10}$)alkyl group wherein one or more of the alkyl group's hydrogen atoms is replaced with an —OH group. Examples of hydroxyalkyl groups include, but are not limited to, —$CH_2OH$, —$CH_2CH_2OH$, —$CH_2CH_2CH_2OH$, —$CH_2CH_2CH_2CH_2OH$, —$CH_2CH_2CH_2CH_2CH_2OH$, —$CH_2CH_2CH_2CH_2CH_2CH_2OH$, and branched versions thereof. The term "ether" or "oxygen ether" refers to an alkyl group wherein one or more of the alkyl group's carbon atoms is replaced with an —O— group. The term ether includes —$CH_2$—(O$CH_2$—$CH_2$)$_q$O$P_1$ compounds where $P_1$ is a protecting group, —H, or a ($C_1$-$C_{10}$)alkyl. Exemplary ethers include polyethylene glycol, diethylether, methylhexyl ether and the like.

"PEG" refers to polyethylene glycol. "PEGylated" refers to a compound comprising a moiety, comprising two or more consecutive ethylene glycol moieties. Non-limiting examples of PEG moieties for PEGylation of a compound include, one or more blocks of a chain of from 1 to 50 ethylene glycol moieties, such as —(O—$CH_2$—$CH_2$)$_n$—·, —($CH_2$—$CH_2$—O)$_n$—, or —(O—$CH_2$—$CH_2$)$_n$—OH·, where n ranges from 2 to 50.

"Heteroatom" refers to N, O, P and S. Compounds that contain N or S atoms can be optionally oxidized to the corresponding N-oxide, sulfoxide or sulfone compounds. "Hetero-substituted" refers to an organic compound in any embodiment described herein in which one or more carbon atoms are substituted with N, O, or S.

"Aryl," alone or in combination refers to an aromatic ring system such as phenyl or naphthyl. "Aryl" also includes aromatic ring systems that are optionally fused with a cycloalkyl ring. A "substituted aryl" is an aryl that is independently substituted with one or more substituents attached at any available atom to produce a stable compound, wherein the substituents are as described herein. "Optionally substituted aryl" refers to aryl or substituted aryl. "Arylene" denotes divalent aryl, and "substituted arylene" refers to divalent substituted aryl. "Optionally substituted arylene" refers to arylene or substituted arylene.

As used herein, the term "polycyclic aryl group" and related terms, such as "polycyclic aromatic group" means a group composed of at least two fused aromatic rings. "Heteroaryl" or "hetero-substituted aryl" refers to an aryl group substituted with one or more heteroatoms, such as N, O, P, and/or S.

"Cycloalkyl" refer to monocyclic, bicyclic, tricyclic, or polycyclic, 3- to 14-membered ring systems, which are either saturated, unsaturated or aromatic. The cycloalkyl group may be attached via any atom. Cycloalkyl also contemplates fused rings wherein the cycloalkyl is fused to an aryl or heteroaryl ring. Representative examples of cycloalkyl include, but are not limited to cyclopropyl, cyclobutyl, cyclopentyl, and cyclohexyl. A cycloalkyl group can be unsubstituted or optionally substituted with one or more substituents as described herein below. "Cycloalkylene" refers to divalent cycloalkyl. The term "optionally substituted cycloalkylene" refers to cycloalkylene that is substituted with 1, 2 or 3 substituents, attached at any available atom to produce a stable compound, wherein the substituents are as described herein.

"Carboxyl" or "carboxylic" refers to group having the indicated number of carbon atoms, where indicated, and terminating in a —C(O)OH group, thus having the structure —R—(O)OH, where R is a divalent organic group that includes linear, branched, or cyclic hydrocarbons. Non-limiting examples of these include: $C_{1-8}$ carboxylic groups, such as ethanoic, propanoic, 2-methylpropanoic, butanoic, 2,2-dimethylpropanoic, pentanoic, etc. "Amine" or "amino" refers to group having the indicated number of carbon atoms, where indicated, and terminating in a —$NH_2$ group, thus having the structure —R—$H_2$, where R is a unsubstituted or unsubstituted divalent organic group that, e.g. includes linear, branched, or cyclic hydrocarbons, and optionally comprises one or more heteroatoms.

Terms combining the foregoing refer to any suitable combination of the foregoing, such as arylalkenyl, arylalkynyl, heteroarylalkyl, heteroarylalkenyl, heteroarylalkynyl, heterocyclylalkyl, heterocyclylalkenyl, heterocyclylalkynyl, aryl, heteroaryl, heterocyclyl, cycloalkyl, cycloalkenyl, alkylarylalkyl, alkylarylalkenyl, alkylarylalkynyl, alkenylarylalkyl, alkenylarylalkenyl, alkenylarylalkynyl, alkynylarylalkyl, alkynylarylalkenyl, alkynylarylalkynyl, alkylheteroarylalkyl, alkylheteroarylalkenyl, alkylheteroarylalkynyl, alkenylheteroarylalkyl, alkenylheteroarylalkenyl, alkenylheteroarylalkynyl, alkynylheteroarylalkyl, alkynylheteroarylalkenyl, alkynylheteroarylalkynyl, alkylheterocyclylalkyl, alkylheterocyclylalkenyl, alkylhererocyclylalkynyl, alkenylheterocyclylalkyl, alkenylheterocyclylalkenyl, alkenylheterocyclylalkynyl, alkynylheterocyclylalkyl, alkynylheterocyclylalkenyl, alkynylheterocyclylalkynyl, alkylaryl, alkenylaryl, alkynylaryl, alkylheteroaryl, alkenylheteroaryl, alkynylhereroaryl. As an example, "arylalkylene" refers to a divalent alkylene wherein one or more hydrogen atoms in an alkylene group is replaced by an aryl group, such as a ($C_3$-$C_8$)aryl group. Examples of ($C_3$-$C_8$)aryl-($C_1$-$C_6$)alkylene groups include without limitation 1-phenylbutylene, phenyl-2-butylene, 1-phenyl-2-methylpropylene, phenylmethylene, phenylpropylene, and naphthylethylene. The term "($C_3$-$C_8$)cycloalkyl-($C_1$-$C_6$)alkylene" refers to a divalent alkylene wherein one or more hydrogen atoms in the $C_1$-$C_6$ alkylene group is replaced by a ($C_3$-$C_8$)cycloalkyl group. Examples of ($C_3$-$C_8$)cycloalkyl-($C_1$-$C_6$)alkylene groups include without limitation 1-cycloproylbutylene, cyclo-proyl-2-butylene, cyclopentyl-1-phenyl-2-methyl propylene, cyclobutylmethylene and cyclohexylpropylene.

Figure 5:
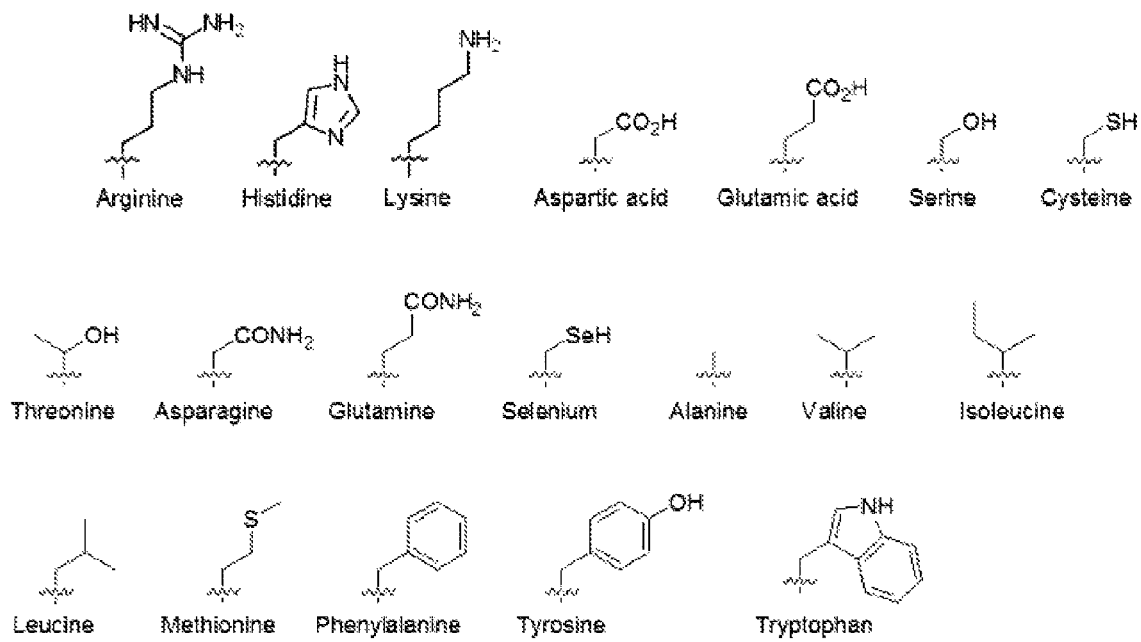
FIG. 5 provides examples of amino acid side chains.

An "amino acid" has the structure H$_2$N—C(R)—C(O)OH, where R is a side chain, such as an amino acid side chain. An "amino acid residue" represents the remainder of an amino acid when incorporated into a chain of amino acids, such as when incorporated into a recognition reagent as discloses herein, e.g., having the structures —NH—C(R)—C(O)—, H$_2$N—C(R)—C(O)— (when at the N-terminus of a polypeptide), or —NH—C(R)—C(O)OH (when at the C-terminus of a polypeptide). An "amino acid side chain" is a side chain for an amino acid, including proteinogenic or non-proteinogenic amino acids. Amino acids have the structure:

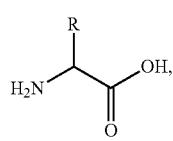

where R is the amino acid side chain. Non-limiting examples of amino acid side chains are shown in FIG. 5. Glycine (H$_2$N—CH$_2$—C(O)OH) has no side chain.

A "peptide nucleic acid" refers to a nucleic acid analog, or DNA or RNA mimic, in which the sugar phosphodiester backbone of the DNA or RNA is replaced by a N-(2-aminoethyl)glycine unit. A gamma PNA (γPNA) is an oligomer or polymer of gamma-modified N-(2-aminoethyl) glycine monomers of the following structure:

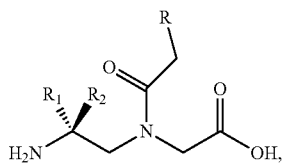

where at least one of R$_1$ or R$_2$ attached to the gamma carbon is not a hydrogen, such that the gamma carbon is a chiral center. When R$_1$ and R$_2$ are hydrogen (N-(2-aminoethyl)-glycine backbone), or the same, there is no such chirality about the gamma carbon. An incorporated PNA or γPNA monomer,

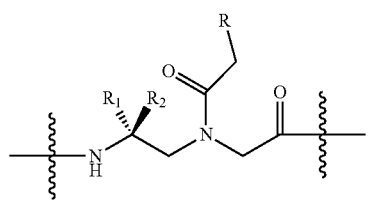

is referred to herein as a PNA or γPNA "residue", in reference to the remaining structure after integration into an oligomer, with each residue having the same or different R group as its base (nucleobase), such as adenine, guanine, cytosine, thymine and uracil bases, or other bases, such as the monovalent and divalent bases described herein, such that the order of bases on the PNA is its "sequence", as with DNA or RNA. A sequence of nucleobases in a nucleic acid or a nucleic acid analog oligomer or polymer, such as a PNA or γPNA oligomer or polymers, binds to a complementary sequence of adenine, guanine, cytosine, thymine and/or uracil residues in a nucleic acid or nucleic acid analog strand by nucleobase pairing, in a Watson-Crick or Watson-Crick-like manner, essentially as with double-stranded DNA or RNA.

A "guanidine" or "guanidinium" group may be added to the recognition reagent to increase solubility and/or bioavailability. Because PNA is produced in a similar manner to synthetic peptides, a simple way to add guanidine groups is to add one or more terminal arginine (Arg) residues to the N-terminal and/or C-terminal ends of the PNA, e.g., γPNA, recognition reagent. Likewise, an arginine side group,

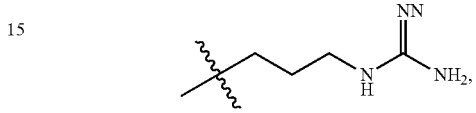

or a guanidine-containing moiety, such as

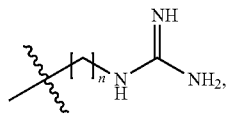

where n, for example and without limitation, ranges from 1-5, or a salt thereof, can be attached to a recognition reagent backbone as described herein. A guanidine-containing group is a group comprising a guanidine moiety, and may have less than 100 atoms, less than 50 atoms, e.g., less than 30 atoms. In one aspect, the guanidine-containing group has the structure:

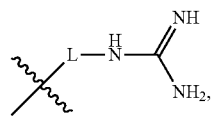

where L is a linker according to any aspect described herein, e.g., a non-reactive aliphatic hydrocarbyl linker, such as a methylene, ethylene, trimethylene, tetramethylene, or pentamethylene linker. In aspects the guanidine-containing group has the structure:

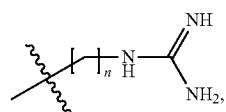

where n is 1-5, e.g., the guanidine group may be arginine.

A "nucleobase" includes primary nucleobases: adenine, guanine, thymine, cytosine, and uracil, as well as modified purine and pyrimidine bases, such as, without limitation, hypoxanthine, xanthene, 7-methylguanine, 5, 6, dihydrouracil, 5-methylcytosine, and 5-hydroxymethylcytosine. FIGS. 3 and 4A-4C also depict non-limiting examples of nucleobases, including monovalent nucleobases (e.g., adenine, cytosine, guanine, thymine or uracil, which bind to one strand of nucleic acid or nucleic acid analogs), and divalent nucleobases (e.g., JB1-JB16 described herein) which bind complementary nucleobases on two strands of DNA simultaneously, and "clamp" nucleobases, such as a "G-clamp," which binds complementary nucleobases with enhanced strength. Additional purine, purine-like, pyrimidine and pyrimidine-like nucleobases are known in the art, for example as disclosed in U.S. Pat. Nos. 8,053,212, 8,389,703, and 8,653,254. For divalent nucleobases JB1-JB16, shown in FIG. 4A, Table A shows the specificity of the different nucleobases. Of note, JB1-JB4 series bind complementary bases (C-G, G-C, A-T and T-A), while JB5-JB16 bind mismatches, and thus can be used to bind two strands of matched and/or mismatched bases. Divalent nucleobases are described in further detail in United States Patent Application Publication No. 20160083434 A1 and International Patent Publication No. WO 2018/058091, both of which are incorporated herein by reference.

TABLE A

Divalent Nucleobases

| Nucleobase | Bases represented |
|---|---|
| JB1 | T/D* |
| JB2 | D/T |
| JB3 | G/C |
| JB4 | C/G |
| JB5 | C/C |
| JB6 | U/U |
| JB7 | G/G |
| JB8 | D/D |
| JB9/JB9b | A/C |
| JB10 | C/A |
| JB11 | U/G |
| JB12 | G/U |
| JB13 | C/U |
| JB14 | U/C |
| JB15 | G/D |
| JB16 | D/G |

*diaminopurine, an adenine analog.

Exemplary γPNA structures that are not end-modified with aryl groups in the manner described herein, but which may be, as described herein, are disclosed in International Patent Publication No. WO 2012/138955, incorporated herein by reference.

Complementary refers to the ability of polynucleotides (nucleic acids) to hybridize to one another, forming interstrand base pairs. Base pairs are formed by hydrogen bonding between nucleotide units in antiparallel polynucleotide strands. Complementary polynucleotide strands can base pair (hybridize) in the Watson-Crick manner (e.g., A to T, A to U, C to G), or in any other manner that allows for the formation of duplexes. When using RNA as opposed to DNA, uracil rather than thymine is the base that is complementary to adenosine. Two sequences comprising complementary sequences can hybridize if they form duplexes under specified conditions, such as in water, saline (e.g., normal saline, or 0.9% w/v saline) or phosphate-buffered saline), or under other stringency conditions, such as, for example and without limitation, 0.1×SSC (saline sodium citrate) to 10×SSC, where 1×SSC is 0.15M NaCl and 0.015M sodium citrate in water. Hybridization of complementary sequences is dictated, e.g., by salt concentration and temperature, with the melting temperature (Tm) lowering with increased mismatches and increased stringency. Perfectly matched sequences are said to be "fully complementary", though one sequence (e.g., a target sequence in an mRNA) may be longer than the other, as in the case of the small recognition reagents described herein in relation to the much longer target sequences on which they concatenate, such as mRNAs containing repeat expansions.

Toxic RNAs containing expanded trinucleotide repeats are the cause of many neuromuscular disorders, one being myotonic dystrophy type I (DMI). DMI is triggered by CTG-repeat expansion in the 3'-UTR of the DMP K gene, resulting in toxic-gain of RNA function through sequestration of MBNL1 protein, among others. Described herein are short probes that are capable of binding nucleic acid sequences, such as repeated nucleic acid sequences, in a sequence-specific and selective manner. For example, as described in the Examples, a short PNA probe, two triplet-repeats in length, containing terminal pyrene moieties is demonstrated to be capable of binding rCUG-repeats in a sequence-specific and selective manner. This probe can discriminate the pathogenic $rCUG^{exp}$ from the wild-type transcript and is able to disrupt the $rCUG^{exp}$-MBNL1 complex. As such, in aspects, described herein are short nucleic acid probes, referred to as genetic recognition reagents, for targeting RNA-repeat expansions associated with DMI and other related neuromuscular disorders.

The methods and compositions described herein overcome three major hurdles presently facing conventional antisense and antigene approaches. A first hurdle concerns the scale and cost of oligonucleotide synthesis. Since oligonucleotides are traditionally synthesized in a step-wise fashion on solid-support, it is difficult to scale up the production. This translates to high-cost and unmet demand for oligonucleotide therapeutics. The methods and compositions described herein overcome this challenge because the recognition reagents are relatively small in size, 3 to 8 nucleotides in length—bordering the molecular weights of small molecules and biomimetics. The compounds described herein can be produced in large scales using convergent, solution-phase synthesis methods, which would translate to lower production costs and greater accessibility to these materials for treatment.

A second hurdle concerns cellular delivery—specifically how to get these nucleic acid probes across the lipid-bilayer of cell membrane and into the cytoplasm and nucleus of the target cells. Most oligonucleotides are not permeable to the cell-membrane due to of their relatively large molecular weight. Their delivery into cells would require the aid of transfecting reagents, or mechanical or electrical transduction. While these approaches have been successfully used to transport oligonucleotides and other macromolecules into cells, they are limited to small scale-up, in vitro (tissue culture) experimental setups. In vivo, systemic delivery (a requirement for treatment of genetic and most infectious diseases) remains an issue, especially for diseases of the central nervous system. The present invention overcomes this limitation because of the reduced size of the recognition reagents and flexibility in the chemical modifications. The fact that they are relatively small in size, they are taken-up more readily by cells and more permeable to the nuclear membrane. Further, with regard to PNAs, such as γPNAs, because of their synthetic flexibility, in that any chemical group can be incorporated in the backbone of PNAs, these recognition reagents can be easily modified with specific chemical functionalities to promote cellular uptake and systemic delivery.

The third hurdle concerns nonspecific binding and cytotoxic effects. When introduced into a cell, a naked piece of oligonucleotide 10-30nt in length, synthetic or otherwise, would bind not only to its designated target but also a slew of other DNA or RNA regions with related sequences. Such nonspecific binding would trap the probe, preventing it from freely diffusing and searching for and binding to its target. A reduction in the effective concentration of the probe, due to nonspecific binding, would lead to a reduction in the efficacy. Moreover, such nonspecific binding could also lead to cytotoxic effects, as the result of mis-regulation of gene expression and/or perturbation of the function of other key proteins. Nonspecific binding, in fact, has been attributed as the main cause of side-effects of oligonucleotide therapeutics (as well as small molecule drugs), and presently there is no solution in sight. The present invention overcomes this limitation by taking advantage of the weak interaction between the short recognition reagent (typically 3 to 8nt in length) and the target. This weak, 'kissing' interaction permits the module to freely diffuse in the intracellular environment in search for its target. Its designated target, in this case, differs from the 'random,' 'single-binding site' hit in that it contains repeated sequence element, which enables the module to assemble next to one another in a cooperative manner through adjacent base stacking and commence 'native chemical ligation' reaction to form a series of extended oligomers of varying lengths.

Presently there are several known genetic diseases associated with unstable repeat expansions of nucleotide sequences, as illustrated in Table B. The challenge is that the target, in this case DNA or RNA, is monotonous in its three-dimensional architecture in comparison to proteins. This makes it difficult for small molecules to discriminate a particular site from a sea of other DNA or RNA sequences.

An advantage of the present invention over the "small molecule drug" approach is in the treatment of cancer and in combating bacterial, viral, and parasitic infections, where the targets are rapidly evolving due to the rapid rate of mutations. There are a number of conserved and repeated elements within the genomes and transcriptomes of the tumorigenic clones and of the bacterial, viral, and parasitic pathogens that could potentially be targeted with this method and approach. The chance for these tumor cells or pathogens to evade these recognition reagents described herein and become resistant is unlikely, as compared to the 'small molecule-protein recognition' approach because the mutation would have to occur at every repeat element within the DNA/RNA template.

The recognition reagents described herein are designed to be chemically inert until they enter the cytoplasm and/or nucleus of a cell, under which condition the recognition reagent hybridizes to a complementary sequence in a nucleic acid, and, if adjacent to a sequence another recognition reagent hybridized to, the adjacent aromatic groups thereof will stack, thereby concatenating the recognition reagents. The recognition reagents recognize and bind their DNA or RNA target through cooperative Watson-Crick (or Watson-Crick-like, hydrogen bonding) base-pairing interactions, upon which the adjacent modules non-covalently concatenate via π-π stacking ("pi stacking") of their terminal aryl groups to form extended, concatenated oligomers in a head-to-tail fashion, e.g., as shown in FIG. 1. The rate of intramolecular vs. intermolecular pi stacking in the recognition reagents can be controlled by modulating the rigidity of recognition reagent's backbone, with rigid, e.g., conformationally preorganized backbones, such as γPNA or LNA backbones limiting intramolecular pi stacking of the terminal aromatic groups, and thus potential inactivation of the recognition reagent. That said, even if some intramolecular pi stacking occurs, the recognition reagent can "open up" when hybridizing to its target sequence. In the presence of the target sequence, hybridization to the target sequence and concatenation predominates.

The recognition reagents described herein combine the features of small molecules, for example, low molecular weight, ease of large-scale production, low production cost, cell permeability, and desired pharmacokinetics, with the sequence-specific recognition of oligonucleotides via Watson-Crick base-pairings. The concatenation of the oligomer recognition reagents has been demonstrated and described in accordance with several examples, which are intended to be illustrative in all aspects rather than restrictive. Thus, the present invention is capable of many variations in detailed implementation.

Examples of applications for the recognition reagents described herein is in the treatment of genetic diseases with repeat expansion of small sequences, such as those listed in Table B.

TABLE B

Genetic diseases associated with unstable repeats

| Disease | Repeat Unit | Gene Name | Normal Repeat Length | Pathogenic Repeat Length |
|---|---|---|---|---|
| FRDA | (GAA)n | FRDA (frataxin) | 6-32 | 200-1,700 |
| FRAXA | (CGG)n | FMR1 (FMRP) | 6-60 | >200 |
| FRAXE | (CCG)n | FMR2 (FMR2) | 4-39 | 200-900 |
| SCA1 | (CAG)n | SCA1 (ataxin 1) | 6-39 | 40-82 |
| SCA2 | (CAG)n | SCA2 (ataxin 2) | 15-24 | 32-200 |
| SCA3 | (MJD)(CAG)n | SCA3 (ataxin 3) | 13-36 | 61-84 |
| SCA6 | (CAG)n | CACNA1A | 4-20 | 20-29 |
| SCA7 | (CAG)n | SCA7 (ataxin 7) | 4-35 | 37-306 |
| SCA17 | (CAG)n | SCA17 (TBP) | 25-42 | 47-63 |
| DRPLA | (CAG)n | DRPLA (atrophin 1) | 7-34 | 49-88 |
| SBMA | (CAG)n | AR (androgen receptor) | 9-36 | 38-62 |
| HD | (CAG)n | HD (huntingtin) | 11-34 | 40-121 |
| MDI | (CTG)n | DMPK (DMPK) | 5-37 | 50-1,000 |
| MD2 | (CCTG)n | ZNF9 (ZNF9) | 10-26 | 75-11,000 |
| FXTAS | (CGG)n | FMR1 (FMRP) | 6-60 | 60-200 |
| SCA8 | (CTG)n | SCA8 | 16-34 | >74 |
| SCA10 | (ATTCT)n | Unknown | 10-20 | 500-4,500 |
| SCA12 | (CAG)n | PPP2R2B | 7-45 | 55-78 |
| HDL2 | (CTG)n | JPH3 | 7-28 | 66-78 |
| ALS | (GGGGCC)n | C9ORF72 | 20-50 | >100 |

Based on Table B, recognition reagents that would target gene products described above include the sequences in a 5' to 3' direction: GAA, CGG, CCG, CAG, CTG, CCTG, ATTCT, and GGGGCC or a sequence complementary thereto, e.g., TTC, CCG, CGG, CTG, CAG, CAGG, AGAAT or GGCCCC, for targeting RNA, or hybridize to target sequences comprising repeats of: GAA, CGG, CCG, CAG, CTG, CCTG, ATTCT, and GGGGCC, or a sequence complementary thereto.

Other potential applications of this invention are in the treatment of cancer (telomere), bacterial infection (resistant strains, targeting the repeated and conserved elements unique to the pathogenic strains), hepatitis C (affecting 3% of the world population for which there are no effective treatment by targeting the repeated elements within the viral RNA genome), malaria (targeting microsatellites that have been shown to be essential in the replication and life cycle of the plasmodium), and AIDS (this is a rapidly moving target for which the new mutant sequence can be chased after by dialing-in the corresponding nucleobase sequence in the recognition reagents).

Therefore, provided herein are recognition reagents—modified nucleic acids—that assemble on a nucleic acid template and cooperatively bind to each-other on the template and concatenate. The recognition reagents are oligomers of nucleic acids or nucleic acid analogs, e.g., from three to ten bases, e.g., 3, 4, 5, 6, 7, 8, 9, or 10 bases, or 3 to 8 bases in length, comprising terminal aromatic (aryl) groups, e.g., fused ring polycyclic aromatic groups of from 2-5 rings, or containing from 8-20 carbons or ring atoms, at their ends (e.g., the 5' end and the 3' end, relative to a nucleic acid or nucleic acid analog). Non-limiting examples of fused ring polycyclic aromatic groups include: pentalene, indene, naphthalene, azulene, heptalene, biphenylene, as-indacene, s-indacene, acenaphthylene, fluorene, phenalene, phenanthrene, anthracene, fluoranthene, acephenanthrylene, aceanthrylene, triphenylene, pyrene, chrysene, naphthacene/tetracene, pleiadene, picene, and perylene, all of which are broadly-known in the chemical arts. The aromatic group is attached at any suitable attachment point in its structure to the recognition reagent backbone in any suitable manner, e.g., with a linker, using any appropriate linking chemistry. For example, as shown in the example below, an amino acid, or an amino acid comprising two amine groups, such as diamino butyric acid (Dab), ornithine (Orn), or lysine (Lys), can be linked to a carboxyl-functionalized aromatic compound, such as, for pyrene as an example, a pyrene-1-carboxylic acid, pyrene-2-carboxylic acid, pyrene-4-carboxylic acid, pyrene-1-acetic acid, pyrene-2-acetic acid, or pyrene-4-acetic acid, forming an amide bond in the linker.

The aromatic group may be heterocyclic or non-heterocyclic in that the aromatic group comprises no heteroatoms, or comprises one or more hetero atom, e.g., S, O, or N in any of its rings. Further, the aromatic group may be substituted with one or more non-reactive groups that do not substantially interfere with function of the recognition reagent in hybridizing to a target sequence and concatenation.

In addition, the aromatic group may have a function apart from its use to concatenate the recognition reagents. In aspects, the aromatic group is an antioxidant, such as a vitamin or an antioxidant, such as riboflavin (vitamin B2), mangostin, or mangiferin, or other natural aromatic antioxidants, present in fruits and vegetables, such as commonly-used dietary supplements to combat oxidative stress, inflammation, cancer, ageing, or other ailments.

The genetic recognition reagents are, in aspects, rigid or conformationally preorganized, as with γPNA and locked nucleic acid backbones. All nucleotide sequences are provided in a 5' to 3' direction, left to right, unless indicated otherwise. In the context of PNA oligomers, which can hybridize in a parallel or anti-parallel orientation, unless indicated otherwise, the sequences thereof are depicted in a 5' to 3' orientation with respect to their nucleobase sequences in relation to their specific Watson-Crick or Watson-Crick-like binding to a complementary nucleic acid strand.

A moiety in a compound, such as an aryl moiety or a nucleobase is covalently attached to the recognition reagent backbone, and thus is said to be "linked" to the backbone. Depending on the chemistry used to prepare the compound, the linkage may be direct, or through a "linker" which is a moiety that covalently attaches two other moieties or groups. In one aspect, the terminal aromatic (aryl) groups are attached to the recognition reagent via a linker. The linker is a non-reactive moiety that links the aromatic group to the backbone of the recognition reagent, and, in aspects includes from 1-10 carbon atoms ($C_1$-$C_{10}$), optionally substituted with a hetero-atom, such as a N, S, or O, or a non-reactive linkage, such as an amide linkage (peptide bond) formed by reacting an amine with a carboxyl group. Examples of $C_1$-$C_{10}$ alkylenes are linear or branched, alkylene (bivalent) moieties optionally comprising a cyclic moiety, such as a methylene, ethylene, trimethylene, tetramethylene, pentamethylene, hexamethylene, hepamethylene, octamethylene, nonamethylene, or decamethylene moiety (that is, —$CH_2$—[$CH_2$]$_n$—, where n=1 to 9), optionally comprising an amide linkage. The linkers are non-bulky in that they do not sterically hinder or otherwise interfere to any substantial extent with the binding of the recognition reagents to a target template, and do not interfere with concatenation of the recognition reagents on the target template. The linker is the remaining moiety resulting from the linking of the aromatic group and the backbone of the recognition reagent, e.g.,

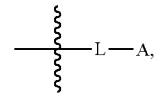

or, in one non-limiting example,

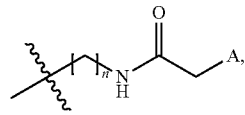

resulting from the linkage of an acetic acid-substituted aryl compound (A), such as pyrene-1-acetic acid, to a Dab (n=1), Orn (n=2), or Lys (n=3) residue.

In further aspects, the linker or linking group is an organic moiety that connects two parts of a compound, e.g., covalently attaches two parts of a compound, such as, for example and without limitation in context of the present invention, connection of the aromatic groups to the backbone of the recognition reagent, connection of a nucleobase to the nucleic acid or nucleic acid analog backbone, and/or connection of a guanidium group to the recognition reagent. Linkers typically comprise a direct bond or an atom such as oxygen or sulfur, a unit such as, C(O), C(O)NH, SO, $SO_2$, $SO_2$NH, or a chain of atoms, such as, but not limited to, substituted or unsubstituted alkyl, substituted or unsubstituted alkenyl, substituted or unsubstituted alkynyl, arylalkyl, arylalkenyl, arylalkynyl, heteroarylalkyl, heteroarylalkenyl, heteroarylalkynyl, heterocyclylalkyl, heterocyclylalkenyl, heterocyclylalkynyl, aryl, heteroaryl, heterocyclyl, cycloalkyl, cycloalkenyl, alkylarylalkyl, alkylarylalkenyl, alkylarylalkynyl, alkenylarylalkyl, alkenylarylalkenyl, alkenylarylalkynyl, alkynylarylalkyl, alkynylarylalkenyl, alkynylarylalkynyl, alkylheteroarylalkyl, alkylheteroarylalkenyl, alkylheteroarylalkynyl, alkenylheteroarylalkyl, alkenyl heteroarylalkenyl, alkenylheteroarylalkynyl, alkynylheteroarylalkyl, alkynylheteroarylalkenyl, alkynylheteroarylalkynyl, alkylheterocyclylalkyl, alkylheterocyclylalkenyl, alkylhererocyclylalkynyl, alkenylheterocyclylalkyl, alkenylheterocyclylalkenyl, alkenylheterocyclylalkynyl, alkynylheterocyclylalkyl, alkynylheterocyclylalkenyl, alkynylheterocyclylalkynyl, alkylaryl, alkenylaryl, alkynylaryl, alkylheteroaryl, alkenylheteroaryl, alkynylhereroaryl, in which one or more carbons, e.g., methylenes or methylidynes (—CH═) is optionally interrupted or terminated by a hetero atom, such as O, S, or N, substituted or unsubstituted aryl, substituted or unsubstituted heteroaryl, substituted or unsubstituted heterocyclic. In one aspect, the linker comprises between about 5 to 25 atoms, e.g., 5-20, 5-10, e.g., 5, 6, 7, 8, 9, 10, 11, 12, 13, 14, 15, 16, 17, 18, 19, or 20 atoms, or a total of from 1 to 10, e.g., 1, 2, 3, 4, 5, 6, 7, 8, 9, or 10 C and heteroatoms, e.g., O, P, N, or S atoms.

For linkage to a PNA, such as a γPNA, an expedient and available linker is one that reacts an amine with a carboxyl group to form an amide linkage, e.g., using well-known peptide synthesis chemistries to add amino acids to the recognition reagent, where the amino acids may be pre-modified with a chemical moiety, such as an aryl moiety, or a guanidine group, as shown in the Example, below, with the addition of an aryl-modified amino acid to link the pyrene aryl moiety to the recognition reagent, and use of arginine to provide the guanidine groups. Linking to non-peptide nucleic acid analogs can be achieved using any suitable linking chemistry as are broadly-known, such as by using carbodiimide chemistry, e.g., EDC (EDAC, 1-Ethyl-3-[3-dimethylaminopropyl] carbodiimide hydrochloride) to link amine-modified Ar groups to the recognition reagent, e.g., via terminal phosphates.

In linking the aromatic group to the backbone of the recognition reagent, the linker is of an appropriate size or length to place the aromatic group in position for π-π stacking during concatenation of the recognition reagents on a target nucleic acid sequence as described herein.

According to one aspect of the invention, a recognition reagent is provided, comprising: a nucleic acid or nucleic acid analog backbone, having a first end and a second end, prepared from three or more, e.g., from 3 to 10, or 3, 4, 5, 6, 7, 8, 9, or 10, or from 3-8, nucleic acid or nucleic acid analog backbone residues, that is optionally conformationally preorganized; a sequence of nucleobases that may be the same or different, attached or linked in a sequence to a plurality of the nucleic acid or nucleic acid analog backbone residues; a first aryl moiety linked to the first end of the nucleic acid or nucleic acid backbone; and a second aryl moiety that is optionally the same as the first aryl moiety, attached to the second end of the of the nucleic acid or nucleic acid backbone. The aryl moieties are, independently, two- to five-ring fused polycyclic aromatic moieties, e.g., substituted or unsubstituted aryl or heteroaryl moieties having from two to five fused rings, for example and without limitation, unsubstituted or substituted pentalene, indene, naphthalene, azulene, heptalene, biphenylene, as-indacene, s-indacene, acenaphthylene, fluorene, phenalene, phenanthrene, anthracene, fluoranthene, acephenanthrylene, aceanthrylene, triphenylene, pyrene, chrysene, naphthacene/tetracene, pleiadene, picene, or perylene, optionally substituted with one or more hetero atoms such as O, N, and/or S, for example, xanthene, riboflavin (vitamin B2), mangostin, or mangiferin, and may be the same or different, and in aspects are the same, provided each stacks with an Ar group of an adjacent recognition reagent when recognition reagents are hybridized to adjacent sequences of a target nucleic acid.

According to one aspect of the present invention, a recognition reagent (recognition module) is provided having the structure:

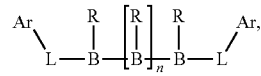

where R are independently, nucleobases, and each instance of R can be the same, or a different nucleobase;
n is an integer ranging from 1 to 6, such as 1, 2, 3, 4, 5, or 6;
each B is independently a ribose 5' phosphate residue, deoxyribose-5-phosphate residue, or a nucleic acid analog backbone residue, and in one aspect, is a backbone residue of a conformationally preorganized nucleic acid analog, such as γPNA or LNA;
L are, independently, linkers, e.g., a non-reactive linker or a non-reactive, non-bulky linker, and each instance of L can be the same or different; and
each instance of Ar is, independently, a two- to five-ring fused polycyclic aromatic moiety, e.g., substituted or unsubstituted aryl or heteroaryl moieties having from two to five fused rings, for example and without limitation, unsubstituted or substituted pentalene, indene, naphthalene, azulene, heptalene, biphenylene, as-indacene, s-indacene, acenaphthylene, fluorene, phenalene, phenanthrene, anthracene, fluoranthene, acephenanthrylene, aceanthrylene, triphenylene, pyrene, chrysene, naphthacene/tetracene, pleiadene, picene, or perylene, optionally substituted with one or more hetero atoms such as O, N, and/or S, for example, xanthene, riboflavin (vitamin B2), mangostin, or mangiferin, and may be the same or different, and in aspects are the same. In some aspects, each Ar stacks with an Ar group of an adjacent recognition reagent when recognition reagents are hybridized to adjacent sequences of a target nucleic acid.

In one aspect, the recognition reagent comprises a PNA backbone, and thus has the structure:

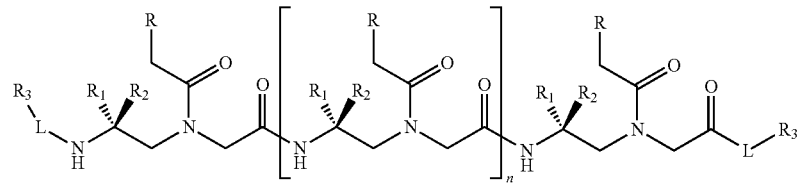

where R are independently, nucleobases, and each instance of R can be the same, or a different nucleobase;

n is an integer ranging from 1 to 6, such as 1, 2, 3, 4, 5, or 6;

each instance of L are, independently, linkers, and may comprise one or more amino acid residues, or substituted or unsubstituted alkyl, substituted or unsubstituted alkenyl, substituted or unsubstituted alkynyl, arylalkyl, arylalkenyl, arylalkynyl, heteroarylalkyl, heteroarylalkenyl, heteroarylalkynyl, heterocyclylalkyl, heterocyclylalkenyl, heterocyclylalkynyl, aryl, heteroaryl, heterocyclyl, cycloalkyl, cycloalkenyl, alkylarylalkyl, alkylarylalkenyl, alkylarylalkynyl, alkenylarylalkyl, alkenylarylalkenyl, alkenylarylalkynyl, alkynylarylalkyl, alkynylarylalkenyl, alkynylarylalkynyl, alkylheteroarylalkyl, alkylheteroarylalkenyl, alkylheteroarylalkynyl, alkenylheteroarylalkyl, alkenylheteroarylalkenyl, alkenylheteroarylalkynyl, alkynylheteroarylalkyl, alkynylheteroarylalkenyl, alkynylheteroarylalkynyl, alkylheterocyclylalkyl, alkylheterocyclylalkenyl, alkylhererocyclylalkynyl, alkenylheterocyclylalkyl, alkenylheterocyclylalkenyl, alkenylheterocyclylalkynyl, alkynylheterocyclylalkyl, alkynylheterocyclylalkenyl, alkynylheterocyclylalkynyl, alkylaryl, alkenylaryl, alkynylaryl, alkylheteroaryl, alkenylheteroaryl, alkynylhereroaryl, in which one or more carbons, e.g., methylenes or methylidynes (—CH═) is optionally interrupted or terminated by a hetero atom, such as O, S, or N, substituted or unsubstituted aryl, substituted or unsubstituted heteroaryl, substituted or unsubstituted heterocyclic, and optionally comprises a guanidine-containing group such as

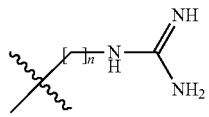

where n=1, 2, 3, 4, or 5, and/or an amino acid side chain;

$R_3$ are, independently, two- to five-ring fused polycyclic aromatic moieties, e.g., substituted or unsubstituted aryl or heteroaryl moieties having from two to five fused rings, for example and without limitation, unsubstituted or substituted pentalene, indene, naphthalene, azulene, heptalene, biphenylene, as-indacene, s-indacene, acenaphthylene, fluorene, phenalene, phenanthrene, anthracene, fluoranthene, acephenanthrylene, aceanthrylene, triphenylene, pyrene, chrysene, naphthacene/tetracene, pleiadene, picene, or perylene, optionally substituted with one or more hetero atoms such as O, N, and/or S, for example, xanthene, riboflavin (vitamin B2), mangostin, or mangiferin, and may be the same or different, and in aspects are the same. In some aspects, each stacks with an aromatic moiety of an adjacent recognition reagent when recognition reagents are hybridized to adjacent sequences of a target nucleic acid;

$R_1$ and $R_2$ are each, independently: H; a guanidine-containing group such as

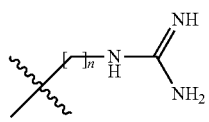

where n=1, 2, 3, 4, or 5; an amino acid side chain, such as:

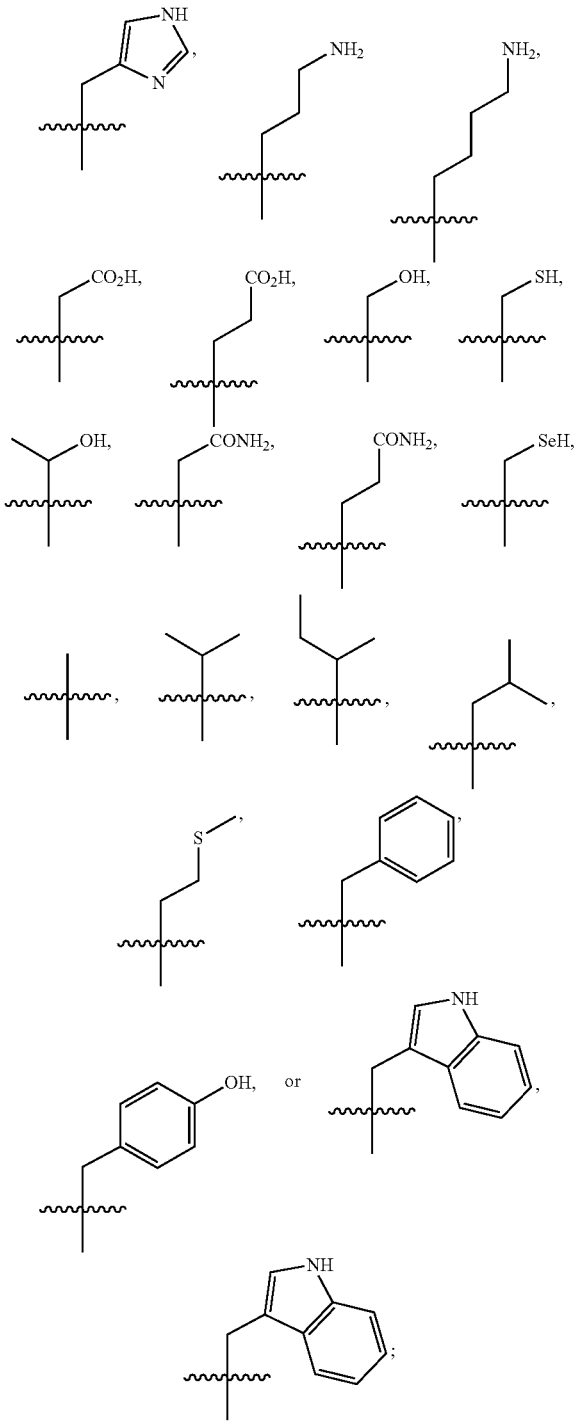

linear or branched $(C_1-C_8)$alkyl, $(C_2-C_8)$alkenyl, $(C_2-C_8)$alkynyl, $(C_1-C_8)$hydroxyalkyl, $(C_3-C_8)$aryl, $(C_3-C_8)$cycloalkyl, $(C_3-C_8)$aryl$(C_1-C_6)$alkylene, $(C_3-C_8)$cycloalkyl$(C_1-C_6)$alkylene, optionally substituted with an ethylene glycol unit comprising from 1 to 50 ethylene glycol moieties; —$CH_2$—$(OCH_2$—$CH_2)_q$—$SP_1$; —$CH_2$—$(OCH_2$—$CH_2)_q$—$NHP_1$; —$CH_2$—$(SCH_2$—$CH_2)_q$—$SP_1$; —$CH_2$—$(OCH_2$—$CH_2)_r$—OH; —$CH_2$—$(OCH_2$—$CH_2)_r$—$NH_2$; —$CH_2$—$(OCH_2$—$CH_2)_r$—$NHC(NH)NH_2$; or —$CH_2$—$(OCH_2$—$CH_2)_r$—S—

S[CH$_2$CH$_2$]$_s$NHC(NH)NH$_2$, where P$_1$ is H, (C$_1$-C$_8$)alkyl, (C$_2$-C$_8$)alkenyl, (C$_2$-C$_8$)alkynyl, (C$_3$-C$_8$)aryl, (C$_3$-C$_8$)cycloalkyl, (C$_3$-C$_8$)aryl(C$_1$-C$_6$)alkylene or (C$_3$-C$_8$)cycloalkyl(C$_1$-C$_6$)alkylene; q is an integer from 0 to 50; r is an integer from 1 to 50, and s is an integer from 1 to 50; and in one aspect R$_1$ and R$_2$ are different, R$_1$ is H and R$_2$ is not H, or R$_2$ is H and R$_1$ is not H. For binding to natural nucleic acids, such as RNA or DNA, R$_1$ is H and R$_2$ is not H, thereby forming "right-handed" L-γPNA. "Left-handed" D-γPNA, in which R$_2$ is H and R$_1$ is not H, does not bind natural nucleic acids. In one aspect, the linker comprises between about 5 to 25 atoms, e.g., 5-20, 5-10, e.g., 5, 6, 7, 8, 9, 10, 11, 12, 13, 14, 15, 16, 17, 18, 19, or 20 atoms, or a total of from 1 to 10, e.g., 1, 2, 3, 4, 5, 6, 7, 8, 9, or 10 C and heteroatoms, e.g., O, P, N, or S atoms. In one aspect, R$_1$ or R$_2$ is (C$_1$-C$_6$)alkyl substituted with —(OCH$_2$—CH$_2$)$_q$—OP$_1$; —(OCH$_2$—CH$_2$)$_q$—NHP$_1$; —(SCH$_2$—CH$_2$)$_q$—SP$_1$; —(OCH$_2$—CH$_2$)$_r$—OH; —(OCH$_2$—CH$_2$)$_r$—NH$_2$; —(OCH$_2$—CH$_2$)$_r$—NHC(NH)NH$_2$; or —(OCH$_2$—CH$_2$)$_r$—S—S[CH$_2$CH$_2$]$_s$NHC(NH)NH$_2$, where P$_1$ is H, (C$_1$-C$_8$) alkyl, (C$_2$-C$_8$)alkenyl, (C$_2$-C$_8$)alkynyl, (C$_3$-C$_8$)aryl, (C$_3$-C$_8$) cycloalkyl, (C$_3$-C$_8$)aryl(C$_1$-C$_6$)alkylene or (C$_3$-C$_8$)cycloalkyl(C$_1$-C$_6$)alkylene; q is an integer from 0 to 50; r is an integer from 1 to 50, and s is an integer from 1 to 50.

In a further aspect, the recognition reagent has the structure:

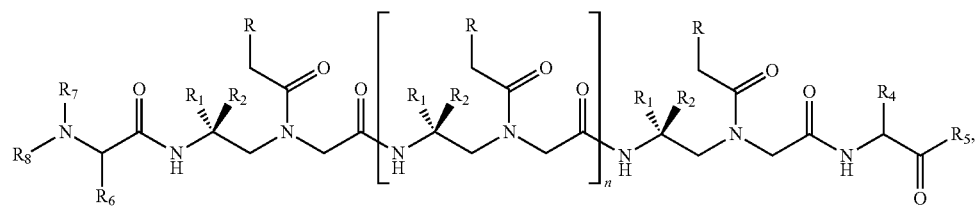

where,
each instance of R is, independently, a nucleobase, and each instance of R can be the same, or a different nucleobase;
n is an integer ranging from 1 to 6, such as 1, 2, 3, 4, 5, or 6;
R$_1$ and R$_2$ are each, independently: H; a guanidine-containing group such as

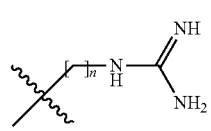

where n=1, 2, 3, 4, or 5; an amino acid side chain, such as:

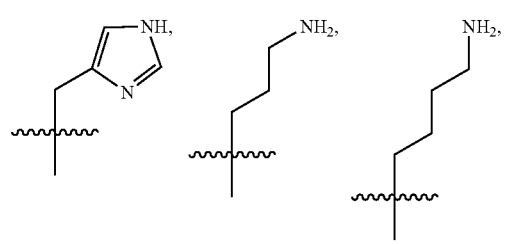

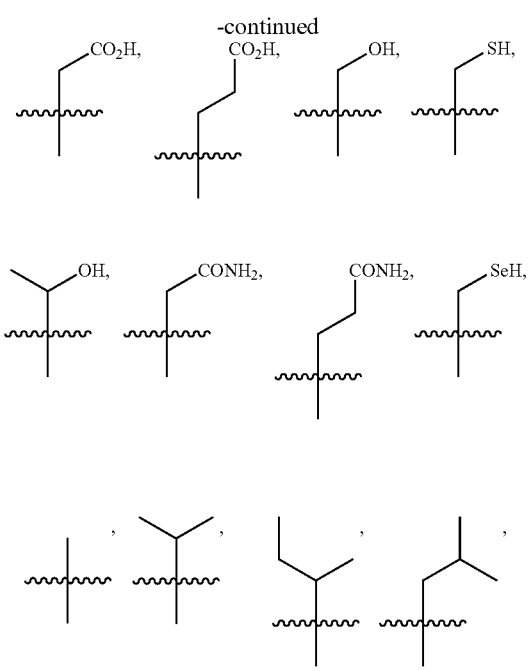

linear or branched (C$_1$-C$_8$)alkyl, (C$_2$-C$_8$)alkenyl, (C$_2$-C$_8$) alkynyl, (C$_1$-C$_8$)hydroxyalkyl, (C$_3$-C$_8$)aryl, (C$_3$-C$_8$)cycloalkyl, (C$_3$-C$_8$)aryl(C$_1$-C$_6$)alkylene, (C$_3$-C$_8$)cycloalkyl(C$_1$-C$_6$) alkylene, optionally substituted with an ethylene glycol unit comprising from 1 to 50 ethylene glycol moieties; —CH$_2$—(OCH$_2$—CH$_2$)$_q$OP$_1$; —CH$_2$—(OCH$_2$—CH$_2$)$_q$—NHP$_1$; —CH$_2$—(SCH$_2$—CH$_2$)$_q$—SP$_1$; —CH$_2$—(OCH$_2$—CH$_2$)$_r$—OH; —CH$_2$—(OCH$_2$—CH$_2$)$_r$—NH$_2$; —CH$_2$—(OCH$_2$—CH$_2$)$_r$—NHC(NH)NH$_2$; or —CH$_2$—(OCH$_2$—CH$_2$)$_r$—S—S[CH$_2$CH$_2$]$_s$NHC(NH)NH$_2$, where P$_1$ is H, (C$_1$-C$_8$)alkyl, (C$_2$-C$_8$)alkenyl, (C$_2$-C$_8$)alkynyl, (C$_3$-C$_8$)aryl, (C$_3$-C$_8$)cycloalkyl, (C$_3$-C$_8$)aryl(C$_1$-C$_6$)alkylene or (C$_3$-C$_8$)cycloalkyl (C$_1$-C$_6$)alkylene; q is an integer from 0 to 50; r is an integer from 1 to 50, and s is an integer from 1 to 50; and in one aspect $R_1$ and $R_2$ are different, $R_1$ is H and $R_2$ is not H, or $R_2$ is H and $R_1$ is not H;

one of $R_4$ and $R_5$, and one of $R_6$, $R_7$, $R_8$ are -L-$R_3$, where each instance of $R_3$ are, independently, two- to five-ring fused polycyclic aromatic moieties, e.g., substituted or unsubstituted aryl or heteroaryl moieties having from two to five fused rings, for example and without limitation, unsubstituted or substituted pentalene, indene, naphthalene, azulene, heptalene, biphenylene, as-indacene, s-indacene, acenaphthylene, fluorene, phenalene, phenanthrene, anthracene, fluoranthene, acephenanthrylene, aceanthrylene, triphenylene, pyrene, chrysene, naphthacene/tetracene, pleiadene, picene, or perylene, optionally substituted with one or more hetero atoms such as O, N, and/or S, for example, xanthene, riboflavin (vitamin B2), mangostin, or mangiferin, and may be the same or different, and in aspects are the same, and in some instances stacks with an $R_3$ group of an adjacent recognition reagent when recognition reagents are hybridized to adjacent sequences of a target nucleic acid, and where L is a linker, e.g. a non-reactive linker or a non-reactive, non-bulky linker, and each instance of L can be the same or different, and may comprise an amino acid residue, or substituted or unsubstituted alkyl, substituted or unsubstituted alkenyl, substituted or unsubstituted alkynyl, arylalkyl, arylalkenyl, arylalkynyl, heteroarylalkyl, heteroarylalkenyl, heteroarylalkynyl, heterocyclylalkyl, heterocyclylalkenyl, heterocyclylalkynyl, aryl, heteroaryl, heterocyclyl, cycloalkyl, cycloalkenyl, alkylarylalkyl, alkylarylalkenyl, alkylarylalkynyl, alkenylarylalkyl, alkenylarylalkenyl, alkenylarylalkynyl, alkynylarylalkyl, alkynylarylalkenyl, alkynylarylalkynyl, alkylheteroarylalkyl, alkylheteroarylalkenyl, alkylheteroarylalkynyl, alkenylheteroarylalkyl, alkenylheteroarylalkenyl, alkenylheteroarylalkynyl, alkynylheteroarylalkyl, alkynylheteroarylalkenyl, alkynylheteroarylalkynyl, akylheterocyclylalkyl, alkylheterocyclylalkenyl, alkylhererocyclylalkynyl, alkenylheterocyclylalkyl, alkenylheterocyclylalkenyl, alkenylheterocyclylalkynyl, alkynylheterocyclylalkyl, alkynylheterocyclylalkenyl, alkynylheterocyclylalkynyl, alkylaryl, alkenylaryl, alkynylaryl, alkylheteroaryl, alkenylheteroaryl, alkynylhereroaryl, in which one or more carbons, e.g., methylenes or methylidynes (—CH=) is optionally interrupted or terminated by a hetero atom, such as O, S, or N, substituted or unsubstituted aryl, substituted or unsubstituted heteroaryl, substituted or unsubstituted heterocyclic, and the remainder of $R_4$, $R_5$, $R_6$, $R_7$, and $R_8$ are each, independently: H; one or more contiguous amino acid residues; a guanidine-containing group such as

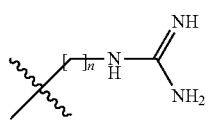

where n=1, 2, 3, 4, or 5; an amino acid side chain, such as:

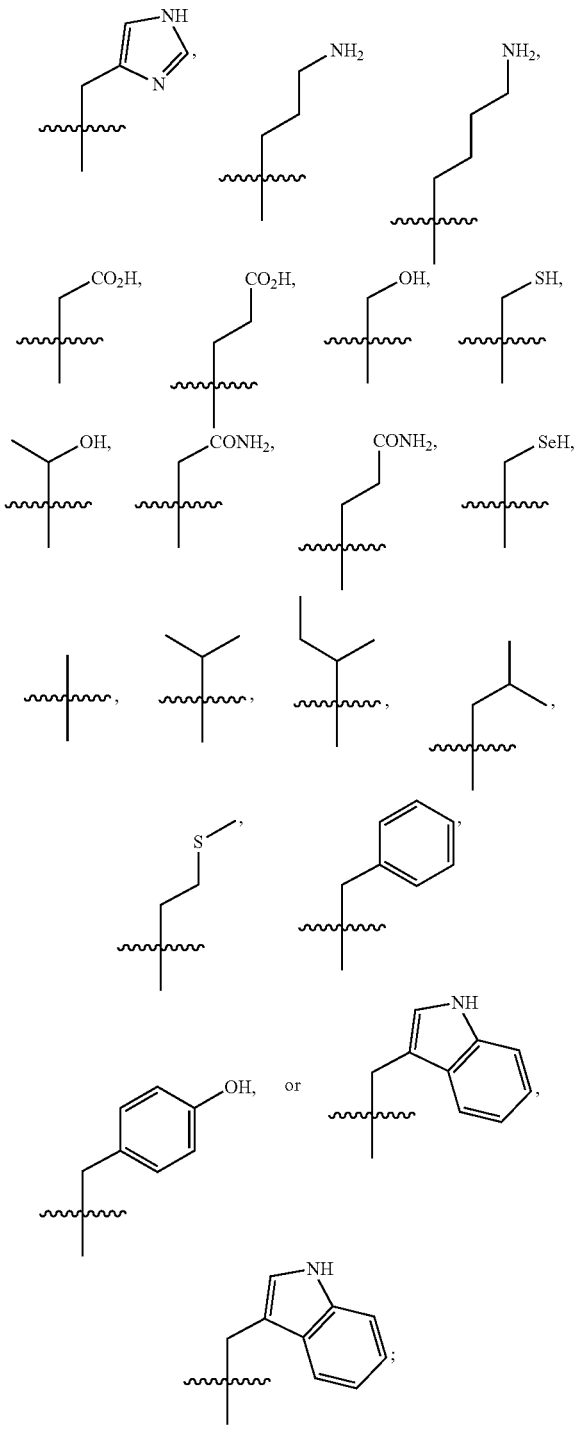

linear or branched $(C_1-C_8)$alkyl, $(C_2-C_8)$alkenyl, $(C_2-C_8)$alkynyl, $(C_1-C_8)$hydroxyalkyl, $(C_3-C_8)$aryl, $(C_3-C_8)$cycloalkyl, $(C_3-C_8)$aryl$(C_1-C_6)$alkylene, $(C_3-C_8)$cycloalkyl$(C_1-C_6)$alkylene, optionally substituted with an ethylene glycol unit comprising from 1 to 50 ethylene glycol moieties; —$CH_2$—$(OCH_2$—$CH_2)_q$—$OP_1$; —$CH_2$—$(OCH_2$—$CH_2)_q$—$NHP_1$; —$CH_2$—$(SCH_2$—$CH_2)_q$—$SP_1$; —$CH_2$—$(OCH_2$—$CH_2)_r$—OH; —$CH_2$—$(OCH_2$—$CH_2)_r$—$NH_2$; —$CH_2$—$(OCH_2$—$CH_2)_r$—$NHC(NH)NH_2$; or —$CH_2$—$(OCH_2$—$CH_2)_r$—S—

S[CH$_2$CH$_2$]$_s$NHC(NH)NH$_2$, where P$_1$ is H, (C$_1$-C$_8$)alkyl, (C$_2$-C$_8$)alkenyl, (C$_2$-C$_8$)alkynyl, (C$_3$-C$_8$)aryl, (C$_3$-C$_8$)cycloalkyl, (C$_3$-C$_8$)aryl(C$_1$-C$_6$)alkylene or (C$_3$-C$_8$)cycloalkyl(C$_1$-C$_6$)alkylene; q is an integer from 0 to 50; r is an integer from 1 to 50, and s is an integer from 1 to 50.

In one aspect R$_4$ and R$_7$ are -L-Ar, and in another aspect, R$_4$ and R$_7$ are -L-Ar and R$_5$ and R$_8$ are Arg. In one aspect, the linker comprises between about 5 to 25 atoms, e.g., 5-20, 5-10, e.g., 5, 6, 7, 8, 9, 10, 11, 12, 13, 14, 15, 16, 17, 18, 19, or 20 atoms, or a total of from 1 to 10, e.g., 1, 2, 3, 4, 5, 6, 7, 8, 9, or 10 C and heteroatoms, e.g., O, P, N, or S atoms. In another aspect, one or more of R$_1$, R$_2$, R$_4$, R$_5$, R$_6$, R$_7$, or R$_8$ is (C$_1$-C$_6$)alkyl substituted with —(OCH$_2$—CH$_2$)$_q$OP$_1$; —(OCH$_2$—CH$_2$)$_q$—NHP$_1$; —(SCH$_2$—CH$_2$)$_q$—SP$_1$; —(OCH$_2$—CH$_2$)$_r$—OH; —(OCH$_2$—CH$_2$)$_r$—NH$_2$; —(OCH$_2$—CH$_2$)$_r$—NHC(NH)NH$_2$; or —(OCH$_2$—CH$_2$)$_r$—S—S[CH$_2$CH$_2$]$_s$NHC(NH)NH$_2$, where P$_1$ is H, (C$_1$-C$_8$)alkyl, (C$_2$-C$_8$)alkenyl, (C$_2$-C$_8$)alkynyl, (C$_3$-C$_8$)aryl, (C$_3$-C$_8$)cycloalkyl, (C$_3$-C$_8$)aryl(C$_1$-C$_6$)alkylene or (C$_3$-C$_8$)cycloalkyl(C$_1$-C$_6$)alkylene; q is an integer from 0 to 50; r is an integer from 1 to 50, and s is an integer from 1 to 50.

In yet another aspect, the recognition reagent comprises a PNA backbone, and thus has the structure:

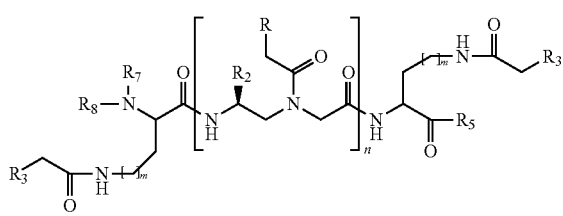

where,
n is an integer ranging from 1 to 8, including 1, 2, 3, 4, 5, 6, or 8;
m is an integer ranging from 1 to 5, such as from 1-3, including 1, 2, 3, 4, or 5;
R$_2$ is: a guanidine-containing group such as

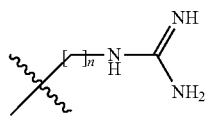

where n=1, 2, 3, 4, or 5, an amino acid side chain, such as:

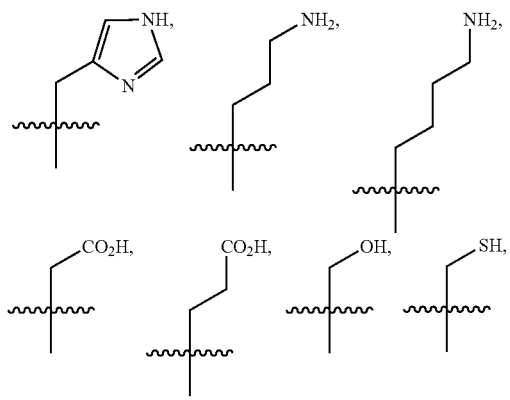

linear or branched (C$_1$-C$_8$)alkyl, (C$_2$-C$_8$)alkenyl, (C$_2$-C$_8$)alkynyl, (C$_1$-C$_8$)hydroxyalkyl, (C$_3$-C$_8$)aryl, (C$_3$-C$_8$)cycloalkyl, (C$_3$-C$_8$)aryl(C$_1$-C$_6$)alkylene, (C$_3$-C$_8$)cycloalkyl(C$_1$-C$_6$)alkylene, optionally substituted with an ethylene glycol unit comprising from 1 to 50 ethylene glycol moieties; —CH$_2$—(OCH$_2$—CH$_2$)$_q$—OP$_1$; —CH$_2$—(OCH$_2$—CH$_2$)$_q$—NHP$_1$; —CH$_2$—(SCH$_2$—CH$_2$)$_q$—SP$_1$; —CH$_2$—(OCH$_2$—CH$_2$)$_r$—OH; —CH$_2$—(OCH$_2$—CH$_2$)$_r$—NH$_2$; —CH$_2$—(OCH$_2$—CH$_2$)$_r$—NHC(NH)NH$_2$; or —CH$_2$—(OCH$_2$—CH$_2$)$_r$—S—S[CH$_2$CH$_2$]$_s$NHC(NH)NH$_2$, where P$_1$ is H, (C$_1$-C$_8$)alkyl, (C$_2$-C$_8$)alkenyl, (C$_2$-C$_8$)alkynyl, (C$_3$-C$_8$)aryl, (C$_3$-C$_8$)cycloalkyl, (C$_3$-C$_8$)aryl(C$_1$-C$_6$)alkylene or (C$_3$-C$_8$)cycloalkyl(C$_1$-C$_6$)alkylene; q is an integer from 0 to 50; r is an integer from 1 to 50, and s is an integer from 1 to 50.

R$_3$ is an unsubstituted fused-ring polycyclic aromatic moiety, such as pentalene, indene, naphthalene, azulene, heptalene, biphenylene, as-indacene, s-indacene, acenaphthylene, fluorene, phenalene, phenanthrene, anthracene, fluoranthene, acephenanthrylene, aceanthrylene, triphenylene, pyrene, chrysene, naphthacene/tetracene, pleiadene, picene, or perylene; and each of R$_5$, R$_7$, and R$_8$ are, independently H, a guanidine-containing group such as

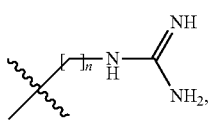

where n=1, 2, 3, 4, or 5, an amino acid side chain, or one or more contiguous amino acid residues, such as one or more Arg residue. In one aspect, R$_3$ is pyrene.

In another aspect, R$_2$ is —CH$_2$—(OCH$_2$—CH$_2$)$_r$—OH, where r is an integer ranging from 1-50, e.g., 1-10, such as 1, 2, 3, 4, 5, 6, 7, 8, 9, or 10, and in one example 2. In another aspect, one or more of R$_2$, R$_5$, R$_7$, or R$_8$ is (C$_1$-C$_6$)alkyl substituted with —(OCH$_2$—CH$_2$)$_q$OP$_1$; —(OCH$_2$—CH$_2$)$_q$ —NHP$_1$; —(SCH$_2$—CH$_2$)$_q$—SP$_1$; —(OCH$_2$—CH$_2$)$_r$—OH; —(OCH$_2$—CH$_2$)$_r$—NH$_2$; —(OCH$_2$—CH$_2$)$_r$—NHC(NH)NH$_2$; or —(OCH$_2$—CH$_2$)$_r$—S—S[CH$_2$CH$_2$]$_s$NHC(NH)NH$_2$, where P$_1$ is H, (C$_1$-C$_8$)alkyl, (C$_2$-C$_8$)alkenyl, (C$_2$-C$_8$)alkynyl, (C$_3$-C$_8$)aryl, (C$_3$-C$_8$)cycloalkyl, (C$_3$-C$_8$)aryl(C$_1$-C$_6$)alkylene or (C$_3$-C$_8$)cycloalkyl(C$_1$-C$_6$)alkylene; q is an integer from 0 to 50; r is an integer from 1 to 50, and s is an integer from 1 to 50.

While the preceding PNA-based recognition reagents are shown without chirality, in one example, the gamma carbons (to which R$_1$ and R$_2$ are attached), are in an (R) orientation, where R$_2$ is H and R$_1$ is not H, or the gamma carbons are in an (S) orientation, where R$_1$ is H and R$_2$ is not H. Further, in one example, when present, in the R$_3$, R$_4$, R$_5$, R$_6$, R$_7$, and/or R$_8$ positions, one or more, or all, chiral amino acid residues may be L-amino acids. In another example, when present, in the R$_3$, R$_4$, R$_5$, R$_6$, R$_7$, and/or R8 positions, one or more, or all, chiral amino acid residues may be D-amino acids.

In any of the structures above, the sequence of the recognition reagent may target expanded repeats, and therefore exemplary nucleobase sequences include (e.g., either in a single recognition reagent or when concatenated), the following: TTC, CCG, CGG, CTG, CAG, CAGG, AGAAT or GGCCCC for targeting mRNA (sense). These sequences are merely exemplary, and for targeting a sequence in a repeated element, such as . . . CAGCAGCAG . . . , any sequential combination of repeated sequences may be included in a single recognition reagent. For example, the sequence CTG will target complementary CAG repeats, but so will TGC and GCT, and dimers thereof, CTGCTG, TGCTGC and GCTGCT. Therefore, the following sequences may be used to target expanded repeats in mRNA shown in Table B: TTC, TTCTTC, TCT, TCTTCT, CTT, CTTCTT, CCG, CCGCCG, CGC, CGCCGC, GCC, GCCGCC, CGG, CGGCGG, GCG, GCGGCG, GGC, GGCGGC, CTG, CTGCTG, TGC, TGCTGC, GCT, GCTGCT, CAG, CAGCAG, AGC, AGCAGC, GCA, GCAGCA, CAGG, CAGGCAGG, AGGC, AGGCAGGC, GGCA, GGCAGGCA, GCAG, GCAGGCAG, AGAAT, GAATA, AATAG, ATAGA, TAGAA, GGCCCC, GCCCCG, CCCCGG, CCCGGC, CCGGCC, and CGGCCC. The preceding sequences are listed 5' to 3' antiparallel to the sense mRNA strand, and are, for example, in a C-terminal to N-terminal direction in γPNA.

R groups of the recognition reagents described herein are arranged in a sequence to be complementary to a sequence of nucleobases in template nucleic acid(s) so that the compositions will bind to the sequence of nucleobases in the template nucleic acid(s). A "template nucleic acid" includes any nucleic acid or nucleic acid analog. When the template is within a cell, it likely will be a nucleic acid, such as DNA or RNA, such as an mRNA to silence. If the recognition reagents are assembled in vitro, the template can be a nucleic acid or any analog thereof that permits specific hybridization to the recognition reagents described herein.

Unless otherwise indicated, the recognition reagents described herein are not described with respect to any particular sequence of nucleobases. The present disclosure is directed to methods and compositions concatenating the described recognition reagents, such as those based on the γPNA backbone, and is independent of the identity and sequence of bases attached thereto. It is expected that any nucleobase sequence attached to the backbone of the described γPNA oligomers would hybridize in an expected, specific manner with a complementary nucleobases sequence of a target nucleic acid or nucleic acid analog by Watson-Crick or Watson-Crick-like hydrogen bonding. The compositions and methods described herein are sequence-independent and describe a novel, generalized method, and related compositions, for template-directed assembly of longer γPNA sequences from shorter γPNA (precursor) sequences.

Nucleobases of the recognition reagents described herein are arranged in a sequence complementary to target sequences of the template nucleic acid, such as a mRNA, e.g. an mRNA containing expanded repeats, so that two or more recognition reagents as described herein bind by base pairing, e.g., by Watson-Crick, or Watson-Crick-like base pairing, to sequences of bases on the template nucleic acid, and concatenate. Non-limiting examples of the combinations of recognition reagents that may be assembled according to the methods described herein are a two recognition reagents in which a first recognition reagent has a nucleobase sequence complementary to a first sequence of a template nucleic acid or nucleic acid analog, and a second recognition reagent has a nucleobases sequence complementary to a second sequence on the template immediately adjacent to the first sequence on the template, such that the two precursors bind a contiguous series of bases on the template, for example, as depicted in FIG. 1. Two or more different recognition reagents can be assembled in that manner, with each binding adjacent short sequences in a longer, contiguous sequence of the template nucleic acid, and concatenating with adjacent recognition reagents. In one example, as shown in FIG. 1, the recognition reagent has a single sequence of nucleobases complementary to a repeated sequence on the template so that two or more identical recognition reagents bind tandemly to a contiguous sequence of repeats on the template. As indicated above, based on Table B, recognition reagents that would target gene products described above include TTC, CCG, CGG, CTG, CAG, CAGG, AGAAT or GGCCCC. In another example, two or more different recognition reagents, having different sequences, can be selected to concatenate on a unique non-repeated sequence. For example, two different hexamer recognition reagents can be produced to hybridize adjacent to each-other on a unique 12 nucleotide sequence present in a target sequence, such as an mRNA.

As indicated above, a method of producing a concatenated nucleic acid or nucleic acid analog, e.g., a conformationally preorganized nucleic acid analog such as γPNA, is provided, comprising, binding a plurality of the recognition reagents according to any aspect described above, to a template nucleic acid or nucleic acid analog. The compositions will concatenate when the terminal aryl groups are in proximity to each other. The aryl groups are considered to be in proximity to each other when they are sufficiently close such that they stack, e.g., as shown in FIG. 1.

In another method, the recognition reagent as described herein, is introduced into a cell for a therapeutic effect. A variety of transfection reagents, suitable for in vitro or in vivo use are suitable for delivery of the compositions described herein to cells, such as FuGENE®, or liposomal preparations (commercially available from multiple sources, See, also, Immordino et al. "Stealth liposomes: review of the basic science, rationale, and clinical applications, existing and potential," (2006) *Int'l J. Nanomedicine* 1(3):297-316). Once within the cells, the recognition reagents will concatenate on a suitable nucleic acid template, such as a native mRNA. When more than one of the recognition reagents hybridize to the same template nucleic acid, placing the terminal aryl groups in proximity to each-other, e.g., next to each-other in a contiguous sequence, the recognition reagents will concatenate due to the pi stacking of the proximal aryl groups. Compounds that do not bind a nucleic acid containing either repeats of the recognition reagent's sequence, or adjacent sequences complementary to more than one of the delivered recognition reagents will release from the bound nucleic acid because the strength of the binding of the e.g., 3-8-mer is not strong enough to maintain the compound on the bound nucleic acid. When more than one recognition reagent binds to a target nucleic acid sequence, e.g., to adjacent, repeated sequences, they will form a concatenated structure of sufficient length to bind the nucleic acid with sufficient strength to remain hybridized to the target sequence, for achieving a desired effect, such as gene silencing where the composition has a sequence of an siRNA, miRNA, mirtron or similar composition.

In aspects a method of treating a patient having a disease as listed in Table B, such as such as myotonic dystrophy type 1 (DM1) and type 2 (DM2) or Huntington's disease is provided. The method comprises administering an amount of a recognition reagent according to any aspect described herein and complementary to a repeat expansion target sequence in mRNA of the patient, effective to knock down expression of the mRNA comprising the repeat expansion target sequence in a patient. For DM1, the target sequence is $(CTG)_n$, and thus the recognition reagent has the sequence: CTG, CTGCTG, TGC, TGCTGC, GCT, or GCTGCT. For DM2, the target sequence is $(CCTG)_n$, and thus the recognition reagent has the sequence: CAGG, CAGGCAGG, AGGC, AGGCAGGC, GGCA, GGCAGGCA, GCAG, or GCAGGCAG. For Huntington's Disease, the target sequence is $(CAG)_n$, and thus the recognition reagent has the sequence: CTG, CTGCTG, TGC, TGCTGC, GCT, or GCTGCT. Sequences complementary to those sequences above are useful for binding the antisense strand of DNA containing the expanded repeats.

For treatment of a patient, the recognition reagent can be administered by any effective route of administration, such as, without limitation, by: parenteral, administration, such as by intravenous, intraperitoneal, intra-organ, such as delivery to the liver, or intramuscular injection; by inhalation, e.g., in a spray or aerosol metered dose inhaler; topically, such as dermal, transdermal, otic, or ophthalmic delivery; transmucosally such as transvaginally or buccal; or orally. The composition may be administered as an individual dose, or in multiple doses over time, so as to maintain reduced expression of a target RNA.

In aspects, provided herein are pharmaceutical compositions and formulations which include the recognition reagents described herein. In one aspect, provided herein are pharmaceutical compositions containing a recognition reagent, as described herein, and a pharmaceutically acceptable carrier. The pharmaceutical compositions containing the recognition reagents are useful for treating a disease, such as a repeat expansion disease, e.g., as listed in Table B. Such pharmaceutical compositions are formulated based on the mode of delivery. One example is compositions that are formulated for systemic administration via parenteral delivery, e.g., by intravenous (IV) or for subcutaneous delivery. The pharmaceutical compositions may be administered in dosages sufficient to treat the disease, e.g., by knocking down expression of an mRNA, as with repeat expansion diseases. In general, a suitable dose of a recognition reagent will be in the range of about 0.001 to about 200.0 milligrams per kilogram body weight of the recipient per day, generally in the range of about 1 to 50 mg per kilogram body weight per day. A repeat-dose regimen may include administration of a therapeutic amount of the recognition reagent on a regular basis, such as every other day or once a year. In certain aspects, the recognition reagent is administered about once per month to about once per quarter (e.g., about once every three months). After an initial treatment regimen, the treatments can be administered on a less frequent basis. The skilled artisan will appreciate that certain factors can influence the dosage and timing required to effectively treat a subject, including but not limited to the severity of the disease or disorder, previous treatments, the general health and/or age of the subject, and other diseases present. Moreover, treatment of a subject with a therapeutically effective amount of a composition can include a single treatment or a series of treatments. Estimates of effective dosages and in vivo half-lives for the individual recognition reagents encompassed herein can be made using conventional methodologies, or based upon in vivo testing using an appropriate animal model.

The pharmaceutical compositions can be administered in any number of ways depending upon whether local or systemic treatment is desired and upon the area to be treated. Administration can be topical (e.g., by a transdermal patch), pulmonary, e.g., by inhalation or insufflation of powders or aerosols, including by nebulizer; intratracheal, intranasal, epidermal and transdermal, oral or parenteral. Parenteral administration includes intravenous, intraarterial, subcutaneous, intraperitoneal or intramuscular injection or infusion; subdermal, e.g., via an implanted device; or intracranial, e.g., by intraparenchymal, intrathecal or intraventricular, administration. The recognition reagent can be delivered in a manner to target a particular tissue, such as the liver (e.g., the hepatocytes of the liver).

Pharmaceutical compositions and formulations for topical administration can include transdermal patches, ointments, lotions, creams, gels, drops, suppositories, sprays, liquids, and powders. Conventional pharmaceutical carriers, aqueous, powder, or oily bases, thickeners and the like can be necessary or desirable. Coated condoms, gloves and the like can also be useful. Suitable topical formulations include those in which the recognition reagents are in admixture with a topical delivery agent such as lipids, liposomes, fatty acids, fatty acid esters, steroids, chelating agents, and surfactants. Suitable lipids and liposomes include neutral (e.g., dioleoylphosphatidyl DOPE ethanolamine, dimyristoylphosphatidyl choline DMPC, distearolyphosphatidyl choline), negative (e.g., dimyristoylphosphatidyl glycerol DMPG), and cationic (e.g., dioleoyltetramethylaminopropyl DOTAP and dioleoylphosphatidyl ethanolamine DOTMA). Recognition reagents can be encapsulated within liposomes or can form complexes thereto, in particular to cationic liposomes. Alternatively, recognition reagents can be complexed to lipids, in particular to cationic lipids. Suitable fatty acids and esters include but are not limited to arachidonic acid, oleic acid, eicosanoic acid, lauric acid, caprylic acid, capric acid, myristic acid, palmitic acid, stearic acid, linoleic acid, linolenic acid, dicaprate, tricaprate, monoolein, dilaurin, glyceryl 1-monocaprate, 1-dodecylazacycloheptan-2-one, an acylcarnitine, an acylcholine, or a $C_{1-20}$ alkyl ester (e.g., isopropylmyristate IPM), monoglyceride or diglyceride; or pharmaceutically acceptable salt thereof. Topical formulations are described in detail in U.S. Pat. No. 6,747, 014. A person of skill in the pharmaceutical and compounding arts can prepare suitable formulations for delivery of the recognition reagents as described herein.

In another aspect, a diagnostic method is provided, comprising contacting a sample comprising nucleic acid with a genetic recognition reagent as described herein, and detecting concatenation of the genetic recognition reagents in the presence of a nucleic acid containing a target sequence of the genetic recognition reagents. In one aspect, nucleic acid is obtained from a cell, e.g., a cell of a patient. The nucleic acid is contacted with the genetic recognition reagent as described herein with fluorescent terminal aryl groups that produce a different emission wavelength or emission intensity when pi stacked, e.g., concatenated. Many fused ring polycyclic aromatic compounds, such as pyrene, are useful for fluorescent detection in this manner. Binding of the genetic recognition reagents to a target sequence within the nucleic acid of the sample, will produce a detectable fluorescent emission such that detection of that emission is considered to be a positive response, indicative of the presence of a nucleic acid comprising the target sequence in the sample. This is a simple way to detect the presence of a nucleic acid comprising repeat expansions of a sequence, and indicative of a repeat expansion disease in a patient from whom the nucleic acid sample is obtained.

In some embodiments, the disclosure provides a compound comprising: a) a series of peptide nuclei acid (PNA) units, wherein the series of units comprises i) a first unit; ii) a last unit; and iii) at least one middle unit between the first unit and the last unit, wherein each unit in the series of units comprises: A) a backbone portion, wherein: 1) the backbone portion of the first unit is covalently bound to the backbone portion of one other unit; 2) the backbone portion of the last unit is covalently bound to the backbone portion of one other unit; and 3) the backbone portion of each middle unit is covalently bound to the backbone portion of two other units; and B) a nucleobase covalently bound to the backbone portion; b) a first aryl moiety covalently linked to the first unit; and c) a last aryl moiety covalently linked to the last unit.

In some embodiments, the disclosure provides a compound comprising: a) a series of PNA units, wherein the series of units comprises i) a first unit; ii) a last unit; and iii) at least one middle unit between the first unit and the last unit, wherein each unit in the series of units comprises: A) a backbone portion, wherein: 1) the backbone portion of the first unit is covalently bound to the backbone portion of one other unit; 2) the backbone portion of the last unit is covalently bound to the backbone portion of one other unit; and 3) the backbone portion of each middle unit is covalently bound to the backbone portion of two other units; and B) a nucleobase covalently bound to the backbone portion; b) two aryl moieties, one covalently linked to the first unit, and another covalently linked to the last unit.

In some embodiments, the disclosure provides a compound wherein the first aryl moiety is covalently linked to the first unit by a first linker moiety, and the last aryl moiety is covalently linked to the last unit by a last linker moiety. In some embodiments, the disclosure provides a compound wherein the first linker moiety and the last linker moiety each independently comprise a guanidine group. In some embodiments, the disclosure provides a compound wherein the first linker moiety and the last linker moiety each independently comprise an amino acid residue. In some embodiments, the disclosure provides a compound wherein the first linker moiety and the last linker moiety each independently comprise three guanidine-containing amino acid residues.

In some embodiments, the disclosure provides a compound wherein the first linker moiety and the last linker moiety each independently comprise three contiguous arginine residues.

In some embodiments, the disclosure provides a compound wherein the series of units is 3 to 8 units. In some embodiments, the disclosure provides a compound wherein the series of units is a gamma-PNA. In some embodiments, the disclosure provides a compound wherein the first aryl moiety and the last aryl moiety are each independently a two- to five-ring fused polycyclic aromatic moiety, for example, a polyaromatic hydrocarbon such as pyrene. In some embodiments, the disclosure provides a compound wherein the first aryl moiety and the last aryl moiety are the same. In some embodiments, the disclosure provides a compound that further comprises an ethylene glycol unit, for example, a diethylene glycol unit.

In some embodiments, the disclosure provides a compound wherein the compound presents the nucleobases in an order that is complementary to a target nucleic acid sequence. In some embodiments, the disclosure provides a compound wherein the target nucleic acid sequence is associated with a repeat expansion disease. In some embodiments, the disclosure provides a compound wherein the repeat expansion disease is myotonic dystrophy type 1 (DM1) or myotonic dystrophy type 2 (DM2). In some embodiments, the disclosure provides a compound wherein, when two of the compounds hybridize to a nucleic acid, the first aryl moiety of one compound and the last aryl moiety of the other compound stack.

In some embodiments, the disclosure provides a compound of the formula: H-$^L$-Arg-CAGCAG-$^L$Arg-NH$_2$ (P1); H-$^L$Arg-$^L$Dab(Pyr)-CAGCAG-$^L$Orn(Pyr)-$^L$Arg-NH$_2$ (P2); H-$^L$Arg-$^L$Orn(Pyr)-CAGCAG-$^L$Orn(Pyr)-$^L$Arg-NH$_2$ (P3); H-$^L$Arg-$^L$Lys(Pyr)-CAGCAG-$^L$Lys(Pyr)-$^L$Arg-NH$_2$ (P4); H-$^L$Arg-$^L$Lys(Pyr)-CATCAG-$^L$Lys(Pyr)-$^L$Arg-NH$_2$ (P5); or H-$^L$Arg-$^L$Lys(Pyr)-CTGCTG-$^L$Lys(Pyr)-$^L$Arg-NH$_2$ (P6), wherein Orn is ornithine, Dab is diamino butyric acid, and Pyr is a carboxyl-functionalized aromatic compound, for example, a pyrene such as pyrene-1-carboxylic acid, pyrene-2-carboxylic acid, pyrene-4-carboxylic acid, pyrene-1-acetic acid, pyrene-2-acetic acid, or pyrene-4-acetic acid.

In some embodiments, the disclosure provides a method of binding a nucleic acid, the method comprising contacting the nucleic acid with a compound of the disclosure, wherein the compound binds to the nucleic acid upon contact. In some embodiments, the disclosure provides a method of knocking down expression of a mRNA in a cell, the method comprising contacting the cell with a compound of the disclosure, wherein the compound knocks down the expression of the mRNA in the cell upon binding a DNA sequence in the cell that corresponds to the mRNA.

In some embodiments, the disclosure provides a compound of the structure:

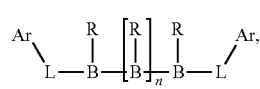

wherein each B is independently a backbone residue; n is 1, 2, 3, 4, 5, or 6; each R is independently a nucleobase; each L is independently a linker; and each Ar is independently a two- to five-ring fused polycyclic aromatic moiety, or a pharmaceutically-acceptable salt thereof.

In some embodiments, the disclosure provides a compound having the structure:

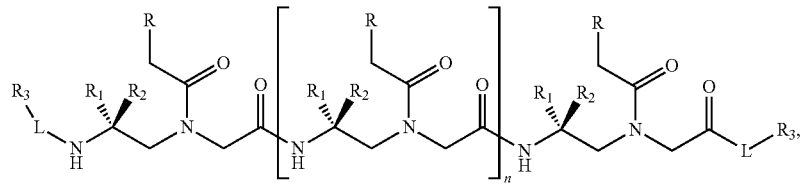

wherein each R is independently a nucleobase; n is 1, 2, 3, 4, 5, or 6; each L is independently a linker; each $R_1$ and $R_2$ is independently: H; a guanidine-containing group; an amino acid side chain; linear or branched $(C_1-C_8)$alkyl, $(C_2-C_8)$alkenyl, $(C_2-C_8)$alkynyl, $(C_1-C_8)$hydroxyalkyl, $(C_3-C_8)$aryl, $(C_3-C_8)$cycloalkyl, $(C_3-C_8)$aryl$(C_1-C_6)$alkylene, $(C_3-C_8)$cycloalkyl$(C_1-C_6)$alkylene, optionally substituted with an ethylene glycol unit comprising from 1 to 50 ethylene glycol moieties; —$CH_2$—$(OCH_2$—$CH_2)_q OP_1$; —$CH_2$—$(OCH_2$—$CH_2)_q$—$NHP_1$; —$CH_2$—$(SCH_2$—$CH_2)_q$—$SP_1$; —$CH_2$—$(OCH_2$—$CH_2)_r$—OH; —$CH_2$—$(OCH_2$—$CH_2)_r$—$NH_2$; —$CH_2$—$(OCH_2$—$CH_2)_r$—$NHC(NH)NH_2$; or —$CH_2$—$(OCH_2$—$CH_2)_r$—S—$S[CH_2CH_2]_s NHC(NH)NH_2$, where $P_1$ is H, $(C_1-C_8)$alkyl, $(C_2-C_8)$alkenyl, $(C_2-C_8)$alkynyl, $(C_3-C_8)$aryl, $(C_3-C_8)$cycloalkyl, $(C_3-C_8)$aryl$(C_1-C_6)$alkylene or $(C_3-C_8)$cycloalkyl$(C_1-C_6)$alkylene; q is an integer from 0 to 50; r is an integer from 1 to 50, and s is an integer from 1 to 50; and each $R_3$ is independently a two- to five-ring fused polycyclic aromatic moiety, or a pharmaceutically-acceptable salt thereof.

In some embodiments, the disclosure provides a compound having the structure:

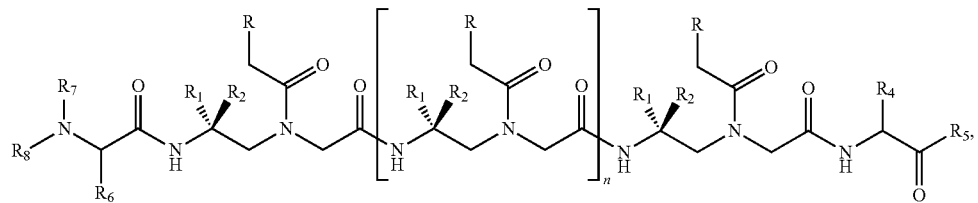

wherein each R is independently a nucleobase; n is 1, 2, 3, 4, 5, or 6; each $R_1$ and $R_2$ is independently: H; a guanidine-containing group; an amino acid side chain; linear or branched $(C_1-C_8)$alkyl, $(C_2-C_8)$alkenyl, $(C_2-C_8)$alkynyl, $(C_1-C_8)$hydroxyalkyl, $(C_3-C_8)$aryl, $(C_3-C_8)$cycloalkyl, $(C_3-C_8)$aryl$(C_1-C_6)$alkylene, $(C_3-C_8)$cycloalkyl$(C_1-C_6)$alkylene, optionally substituted with an ethylene glycol unit comprising from 1 to 50 ethylene glycol moieties; —$CH_2$—$(OCH_2$—$CH_2)_q OP_1$; —$CH_2$—$(OCH_2$—$CH_2)_q$—$NHP_1$; —$CH_2$—$(SCH_2$—$CH_2)_q$—$SP_1$; —$CH_2$—$(OCH_2$—$CH_2)_r$—OH; —$CH_2$—$(OCH_2$—$CH_2)_r$—$NH_2$; —$CH_2$—$(OCH_2$—$CH_2)_r$—$NHC(NH)NH_2$; or —$CH_2$—$(OCH_2$—$CH_2)_r$—S—$S[CH_2CH_2]_s NHC(NH)NH_2$, where $P_1$ is H, $(C_1-C_8)$alkyl, $(C_2-C_8)$alkenyl, $(C_2-C_8)$alkynyl, $(C_3-C_8)$aryl, $(C_3-C_8)$cycloalkyl, $(C_3-C_8)$aryl$(C_1-C_6)$alkylene or $(C_3-C_8)$cycloalkyl$(C_1-C_6)$alkylene; q is an integer from 0 to 50; r is an integer from 1 to 50, and s is an integer from 1 to 50; one of $R_4$ or $R_5$, and one of $R_6$, $R_7$, or $R_8$ are -L-$R_3$, and the remainder of $R_4$, $R_5$, $R_6$, $R_7$, and $R_8$ are each, independently, H, one or more contiguous amino acid residues, a guanidine-containing group, an amino acid side chain, linear or branched $(C_1-C_8)$alkyl, $(C_2-C_8)$alkenyl, $(C_2-C_8)$alkynyl, $(C_1-C_8)$hydroxyalkyl, $(C_3-C_8)$aryl, $(C_3-C_8)$cycloalkyl, $(C_3-C_8)$aryl $(C_1-C_6)$alkylene, $(C_3-C_8)$cycloalkyl$(C_1-C_6)$alkylene, optionally substituted with an ethylene glycol unit comprising from 1 to 50 ethylene glycol moieties, —$CH_2$—$(OCH_2$—$CH_2)_q SP_1$, —$CH_2$—$(OCH_2$—$CH_2)_q$—$NHP_1$, —$CH_2$—$(OCH_2$—$CH_2)_q$—$SP_1$, —$CH_2$—$(SCH_2$—$CH_2)_q$—$SP_1$, —$CH_2$—$(OCH_2$—$CH_2)_r$—OH, —$CH_2$—$(OCH_2$—$CH_2)_r$—$NH_2$, —$CH_2$—$(OCH_2$—$CH_2)_r$—$NHC(NH)NH_2$, or —$CH_2$—$(OCH_2$—$CH_2)_r$—S—$S[CH_2CH_2]_s NHC(NH) NH_2$, where $P_1$ is selected from the group consisting of H, $(C_1-C_8)$alkyl, $(C_2-C_8)$alkenyl, $(C_2-C_8)$alkynyl, $(C_3-C_8)$aryl, $(C_3-C_8)$cycloalkyl, $(C_3-C_8)$aryl$(C_1-C_6)$alkylene and $(C_3-C_8)$cycloalkyl$(C_1-C_6)$alkylene; q is an integer from 0 to 50; r is an integer from 1 to 50, and s is an integer from 1 to 50; each $R_3$ is independently a two- to five-ring fused polycyclic aromatic moiety; and each L is independently a linker, or a pharmaceutically-acceptable salt thereof.

In some embodiments, the disclosure provides a compound having the structure:

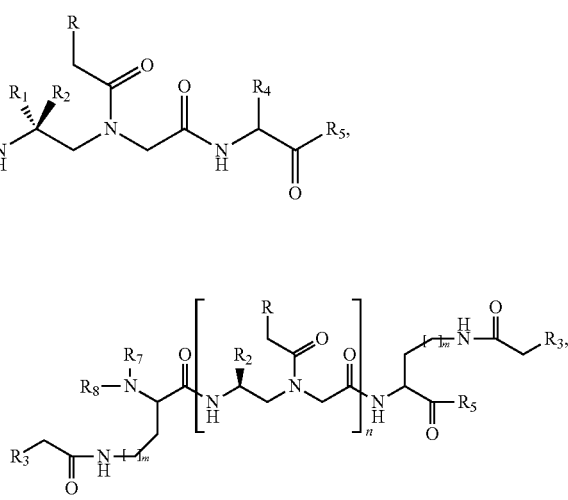

wherein n is 1, 2, 3, 4, 5, 6, 7, or 8; m is 1, 2, 3, 4, or 5; $R_2$ is: a guanidine-containing group; an amino acid side chain; linear or branched $(C_1-C_8)$alkyl, $(C_2-C_8)$alkenyl, $(C_2-C_8)$alkynyl, $(C_1-C_8)$hydroxyalkyl, $(C_3-C_8)$aryl, $(C_3-C_8)$cycloalkyl, $(C_3-C_8)$aryl$(C_1-C_6)$alkylene, $(C_3-C_8)$cycloalkyl$(C_1-C_6)$alkylene, optionally substituted with an ethylene glycol unit comprising from 1 to 50 ethylene glycol moieties; —$CH_2$—$(OCH_2$—$CH_2)_q OP_1$; —$CH_2$—$(OCH_2$—$CH_2)_q$—$NHP_1$; —$CH_2$—$(SCH_2$—$CH_2)_q$—$SP_1$; —$CH_2$—$(OCH_2$—$CH_2)_r$—OH; —$CH_2$—$(OCH_2$—$CH_2)_r$—$NH_2$; —$CH_2$—$(OCH_2$—$CH_2)_r$—$NHC(NH)NH_2$; or —$CH_2$—$(OCH_2$—$CH_2)_r$—S—$S[CH_2CH_2]_s NHC(NH)NH_2$, where $P_1$ is H, $(C_1-C_8)$alkyl, $(C_2-C_8)$alkenyl, $(C_2-C_8)$alkynyl, $(C_3-C_8)$aryl, $(C_3-C_8)$cycloalkyl, $(C_3\text{-}C_8)$aryl$(C_1\text{-}C_6)$alkylene or $(C_3\text{-}C_8)$cycloalkyl $(C_1\text{-}C_6)$alkylene; q is an integer from 0 to 50; r is an integer from 1 to 50, and s is an integer from 1 to 50; $R_3$ is pentalene, indene, naphthalene, azulene, heptalene, biphenylene, as-indacene, s-indacene, acenaphthylene, fluorene, phenalene, phenanthrene, anthracene, fluoranthene, acephenanthrylene, aceanthrylene, triphenylene, pyrene, chrysene, naphthacene/tetracene, pleiadene, picene, or perylene; and each of $R_5$, $R_7$, and $R_8$ is independently H, an amino acid side chain, a chain of at least one contiguous amino acid residues, or

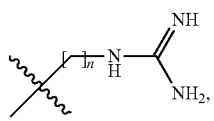

wherein n is 1, 2, 3, 4, or 5, or a pharmaceutically-acceptable salt thereof.

In some embodiments, the disclosure provides a genetic recognition reagent comprising: a nucleic acid or nucleic acid analog backbone, having a first end and a second end, and having from three to eight ribose-5-phosphate, deoxyribose-5-phosphate, or nucleic acid analog backbone residues; nucleobases, that may be the same or different, linked to a plurality of the ribose-5-phosphate, deoxyribose-5-phosphate, or nucleic acid analog backbone residues; a first aryl moiety linked by a linker to the first end of the nucleic acid or nucleic acid analog backbone; and a second aryl moiety that is optionally the same as the first aryl moiety, linked by a linker to the second end of the of the nucleic acid or nucleic acid analog backbone.

In some embodiments, the present disclosure provides a method of detection, comprising a) hybridizing a first probe nucleic acid comprising a first end connected to a first emitter moiety and a second end connected to a second emitter moiety to a first repeat portion of a target nucleic acid; and b) hybridizing a second probe nucleic acid comprising a first end connected to a third emitter moiety and a second end connected to a fourth emitter moiety to a second repeat portion of the target nucleic acid; wherein i) the first and second repeat portions of the target nucleic acid are associated with a repeat expansion disorder; ii) binding of the first probe nucleic acid and the second probe nucleic acid to the target presents the first or second emitter moiety in close proximity to the third or fourth emitter moiety; and iii) the presence of the first or second emitter moiety in close proximity to the third or fourth emitter moiety causes a change in emission wavelength of the emitter moieties that are in close proximity.

In some embodiments, the method of detection further comprises detecting the change in the emission wavelength of the emitter moieties that are in close proximity. In some embodiments hybridizing the first probe nucleic acid to the first repeat portion increases an affinity of the second probe nucleic acid to the second repeat portion. In some embodiments the presence of the first or second emitter moiety in close proximity to the third or fourth emitter moiety causes a pi-pi stacking interaction between the first or second emitter moieties and third or fourth emitter moieties. In some embodiments, the target nucleic acid is obtained directly from a biological sample.

EXAMPLE

Figure 6:
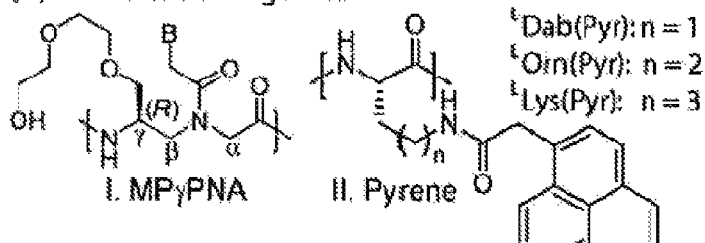
FIG. 6 describes the chemical building blocks (A, Panel A), MPγPNA oligomers (B), and RNA targets (C) (SEQ ID NO: 2) described in the Example.

Peptide nucleic acid (PNA), a randomly-folded nucleic acid mimic comprising a pseudopeptide backbone can be preorganized into a right-handed helical motif, and its water solubility and biocompatibility can be improved by installing a (R)-diethylene glycol (miniPEG, or MP) unit at the gamma backbone (FIG. 6). Such a molecular foldamer exhibits ultra-high affinity and sequence-specificity for DNA or RNA. These thermodynamic properties support the feasibility to develop relatively short MPγPNA probes for targeting repeat expansions, such as rCUG$^{exp}$.

Methods

UV Melting Experiments: All UV-melting samples were prepared by mixing MPγPNA with RNA targets at the indicated concentrations in a physiologically simulated buffer (10 mM NaPi (sodium phosphate buffer), 150 mM KCl, 2 mM MgCl$_2$; pH 7-4), and annealed by incubation at 90° C. for 5 min followed by a gradual cooling to room temperature. UV melting curves were collected using Agilent Cary UV-Vis 300 spectrometer equipped with a thermoelectrically controlled multi-cell holder. UV-melting spectra were collected by monitoring UV-absorption at 260 nm from 25° C. to 95° C. in the heating runs, and from 95° C. to 25° C. in the cooling runs, both at the rate of 0.2° C. per min. The cooling and heating curves were nearly identical, indicating that hybridization process is reversible. The recorded spectra were smoothed using a 20-point adjacent averaging algorithm. The first derivatives of the melting curves were taken to determine the melting temperatures of the duplex.

Steady-State Fluorescent Measurements: All steady-state fluorescence samples were prepared by mixing P$_4$-RNA duplexes at the indicated concentrations in a simulated physiological buffer and annealed by incubation at 90° C. for 5 min, followed by a gradual cooling to 37° C. The samples were incubated at 37° C. for 1 hr before the measurements. Steady-state fluorescence data were collected at 37° C. by Cary Eclipse Fluorescence Spectrometer. ($\varepsilon_{ex}$=350 nm and $\varepsilon_{em}$=480 nm) with slit size.

Real-Time Fluorescent Binding Kinetics: For real-time fluorescent kinetic experiment the samples were prepared as followed: (1) P$_4$ alone, (2) P$_4$, T$_1$ and T$_8$ annealed prior to the measurement, (3) addition of P$_4$ to T$_8$ at 37° C., and (4) addition of P4 to T$_8$ in the presence of T$_1$ at equimolar binding sites. Realtime fluorescence data were collected at 37° C. by Cary Eclipse Fluorescence Spectrometer. ($\varepsilon_{ex}$=350 nm and $\varepsilon_{em}$=480 nm) with slit size.

Competitive Binding Assay: T6 was purchased from IDT. T48, the same as r(CUG)$_{96}$, was prepared as previous described, except that the DNA template was (CTG)$_{96}$. T6 and T$_4$8 were separately annealed by heating up to 90° C. for 5 min and gradually cooled to room temperature. Probes and RNA targets were mixed at the indicated concentrations and incubated in a physiologically simulated buffer at 37° C. for 4 hr in silicon-coated Eppendorf tubes. The samples were then loaded onto 2% agarose-gel containing IX SYBR-Gold with Tris-borate buffer and electrophoretically separated at 100 V for 15 min. The bands were visualized by UV-Transilluminator.

Analysis of T$_4$8-MBNL1 Disruption by Probe: T48 and GST-MBNL$_1$-F$_1$ were prepared as previously described. Radioisotopically labeled T$_4$8 was incubated with GST-MBNL$_1$-F$_1$ in buffer containing 50 mM Tris, 50 mM NaCl, 50 mM KCl and 1 mM MgCl$_2$ (pH 8.0) at the indicated concentrations at 25° C. for 30 minutes. The indicated concentration of P$_4$ was added to T$_4$8-MBNL$_1$ complex. The samples were immediately loaded to 1.5% agarose gels with 1× Tris-borate buffer and electrophoretically separated at 100 V for 2 hrs. The bands were visualized by phosphorimaging and quantified with ImageQuant (Molecular Dynamics).

We synthesized a series of MPγPNA probes, 6-bases in length, containing terminal pyrenes (P2 through P6, FIG. 6), along with the P1 control, and characterized their binding properties. P2 through P4 comprised different linker lengths connecting pyrene to the probes' backbone (FIG. 6, II). P5 and P6 contained corresponding single and double base mismatches, designed to test recognition specificity. We selected a tandem triplet-repeat because prior study showed that MPγPNA of a similar length was able to transiently interact with RNA target at a physiological temperature. Pyrene was adopted as a model compound for promoting binding cooperativity because of its expanded aromatic surface and large bathochromic shift in the emission upon dimerization, and the fact that it has been successfully demonstrated in the cooperative binding of polyamides to DNA by Sugiyama and coworkers. The latter photochemical property provides a convenient means for monitoring probe hybridization and pyrene-pyrene interaction. The monomers were prepared according to the published protocols. Probes were synthesized on HMBA-resin, purified by RP-HPLC, and verified by MALDI-TOF MS. A series of model RNA targets containing different numbers of hexameric r(CUGCUG)-repeats were chosen for binding study (FIG. 6 (C)).

Figure 7:
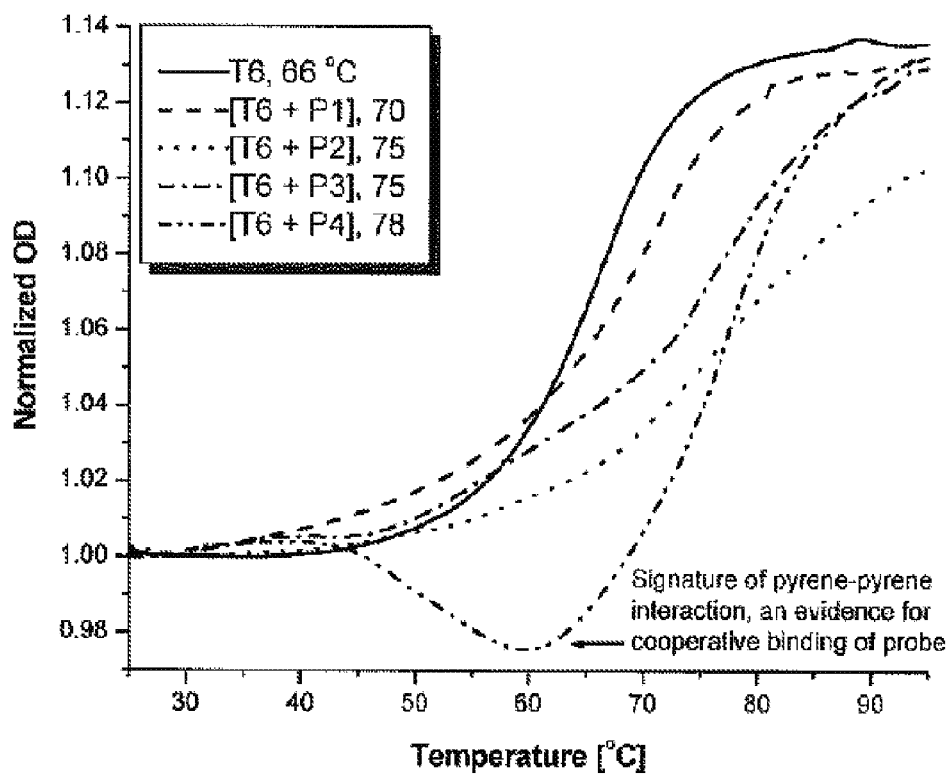
FIG. 7. UV-melting profiles of PI through P4 with T6. The concentration of T6 was 1 µM and that of each probe was 6 µM, prepared in a physiologically relevant buffer. An evidence for cooperative binding was clearly observed with P4.
Figure 8:
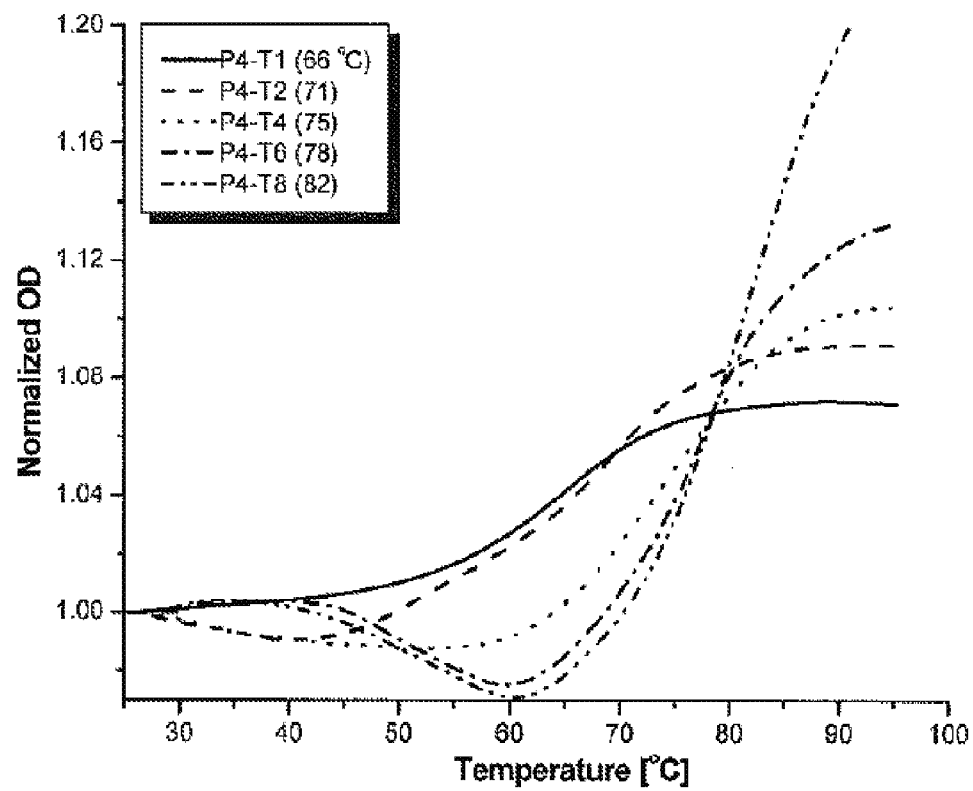
FIG. 8. UV-melting profiles of P4-RNA heteroduplexes in a physiologically relevant buffer at 8 µM strand concentration. The samples were prepared by mixing 8 µM of P4 with the respective RNA targets at the following concentrations: T1=8.0 µM, T2=4.0 µM, T4=2.0 µM, T6=1.3 µM, T8=1.0 µM in a physiological buffer and annealed at 90° C. for 5 min, followed by a gradual cooling to room temperature.
Figure 9:
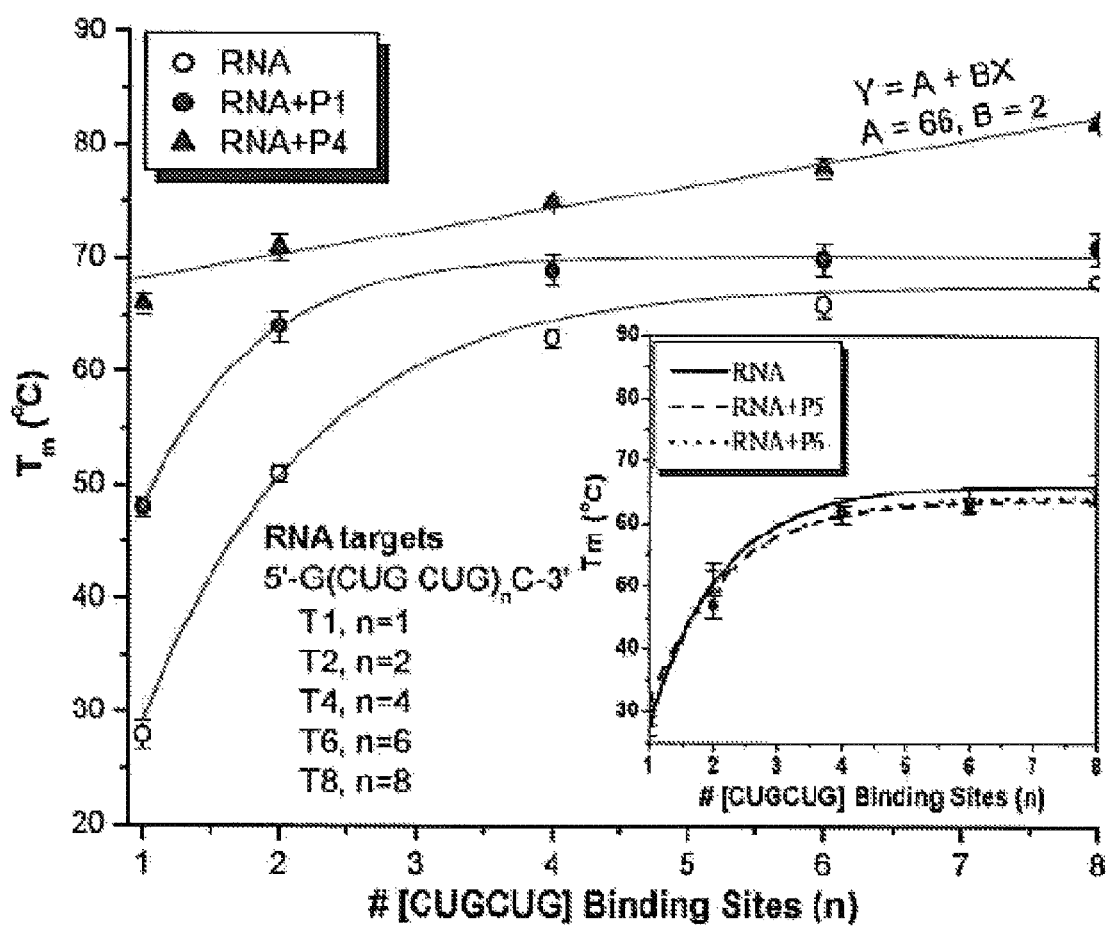
FIG. 9. UV-melting transitions of RNAs and the corresponding probe-RNA heteroduplexes containing the perfectly-matched and mismatched sequences as a function of the number of r(CUGCUG)n-binding-sites in the targets. Inset: UV-melting profiles Of RNA with P5 and P6 containing single and double base-mismatches, respectively.

All the experiments were conducted at a physiologically relevant ionic strength (10 mM NaPi, 150 mM KCl, and 2 mM $MgCl_2$ at pH 7.4). RNA concentrations were prepared such that the number of r(CUGCUG)-repeats in each sample was the same. Preliminary study revealed that among the three linker lengths (FIG. 6, P2 through P4), lysine yielded the highest degree of binding cooperativity (FIG. 7). Based on this finding, we selected P4 and carried out UV-melting study with the various RNA targets. Our result showed that the melting transitions ($T_m$s) of the P4-RNA series monotonically increased with the number of binding-sites in the targets (FIG. 8). Pyrene-pyrene interaction is evident from the inverse absorption profiles of P4-T6 and P4-T8 in the 40-70° C. temperature range. Upon heating, the solvophobic effect becomes more pronounced due to the inverse intensity distribution of vibronic transition of pyrene excimer relative to monomer, $Ae^{o \rightarrow o}/Am^{o \rightarrow o} \sim 0.6$, prior to their dissociation upon further heating. Comparing the $T_m$s of the three series, P4-RNA, P1-RNA, and RNA, revealed a distinct pattern. The $T_m$s of the P4-RNA series follow a positive linear correlation, $Y=66+2X$, with X being the number of binding-sites in the targets (FIG. 9). However, as for the latter two series, the $T_m$s plateaued at X~3, indicating that increasing the number of binding-sites in RNA beyond three does not necessarily make the corresponding hairpin structures thermodynamically more stable. In contrast to the perfectly-matched sequence, no discernible differences in the $T_m$s of RNAs were observed with the mismatched P5 and P6 probes (Figure Inset). Together, these results show that P4 binds cooperatively and sequence-specifically to RNA repeated targets. Such a phenomenon was also observed with PNA-ligand conjugates.

To further corroborate these findings, we carried out fluorescent measurements under identical conditions. The samples were excited at 340 nm, and the fluorescent signals were recorded from 345 to 650 nm. Characteristic of the pyrene-pyrene excimer formation is the emission at 480 nm (FIG. 10). Consistent with the UV-melting data, the degree of P4 binding cooperativity increases with the number of binding-sites in RNAs, as observed in the gradual increase in the fluorescent intensities at 480 nm. The samples were markedly different under UV-illumination, such that they could be distinguished with the naked eyes (FIG. 11). Kinetic measurements further revealed that the hybridization of P4 to T8 was nearly complete within 10 min (FIG. 10, Inset). Addition of a competing T1 strand at an equimolar ratio of binding-sites resulted in the hybridization lag-time of 2 min, after which complete fluorescent recovery and binding of P4 to T8 were observed. This result shows that the interaction of P4 with single-binding-site RNA is weak and transient under a physiologically simulated condition, and that a complete recovery and binding of probe to RNA-repeats is achieved within a similar time frame.

To assess the recognition selectivity of P4 probe, we carried out a competitive binding assay. Equimolar binding-sites of the normal-length T6 and the pathogenic T48 [$r(CUG)_{96}$, prepared according to our published protocol, were incubated with different concentrations of P4 at 37° C. for 16 hrs. The resulting mixtures were analyzed by agarose-gel and stained with SYBR-Gold for visualization. Inspection of FIG. 12 reveals that P4 was able to discriminate the pathogenic T48 from the wt-T12 (compare lane 6 to lane 3). No evidence of binding was observed with the single-base mismatched P5 probe (compare lane 7 to lane 3). These results indicate that P4 is able to discriminate the expanded T48 transcript from the wt-T6, and that probe binding occurs in a sequence-specific manner.

Next, we determined whether P4 can disrupt the $rCUG^{exp}$-$MBNL_1$ complex by performing a gel-shift assay. The RNA-protein complex was prepared by incubating 5'-$^{32}$P-labelled T48 with $MBNL_1$ at a physiologically relevant condition. Upon confirmation of their binding, P4 was added and the resulting mixtures were incubated at 37° C. for 4 hrs prior to their analysis by nondenaturing PAGE and autoradiography. Formation of the T48-$MBNL_1$ complexes is evident by the smeared patterns observed in lanes 2 through 4 of FIG. 13. Addition of P4 resulted in the formation of a shifted band, which became more pronounced with increasing probe concentrations (lanes 5 through 7). We take this result as an evidence of P4 being able to disrupt the $rCUG^{exp}$-$MBNL_1$ complex, resulting in the formation of T48-P4 heteroduplex and in the displacement of all $MBNL_1$ proteins from the RNA transcript. Such a capability is critical to the interference of the DM1 disease pathway.

Compared to the conventional antisense agents, which are typically in the range of 15-30 nucleotides in length, or to a shorter version comprising all-locked nucleic acid (LNA), MPγPNA is synthetically more flexible. Its structure and chemical functionality can be easily modified to meet the application requirements on hand. The smaller probe size offers several distinct benefits for biological and biomedical applications, including greater ease of chemical synthesis and scale-up, and improvements in recognition specificity and selectivity (and possibly pharmacokinetic properties). Pyrene was chosen as a model compound for inducing intermolecular π-π interaction because of its appealing chemical and photophysical properties. However, in the actual biological and biomedical applications, such an aromatic pendant group can be readily replaced with a more biologically benign, or a natural product providing health benefits, such as riboflavin (vitamin B2), mangostin, or mangiferin, all of which can promote π-π interaction due to the aromatic, fused ring structure (below). These are natural antioxidants, present in fruits and vegetable, commonly used as dietary supplements to combat oxidative stress, inflammation, cancer, aging, and other ailments.

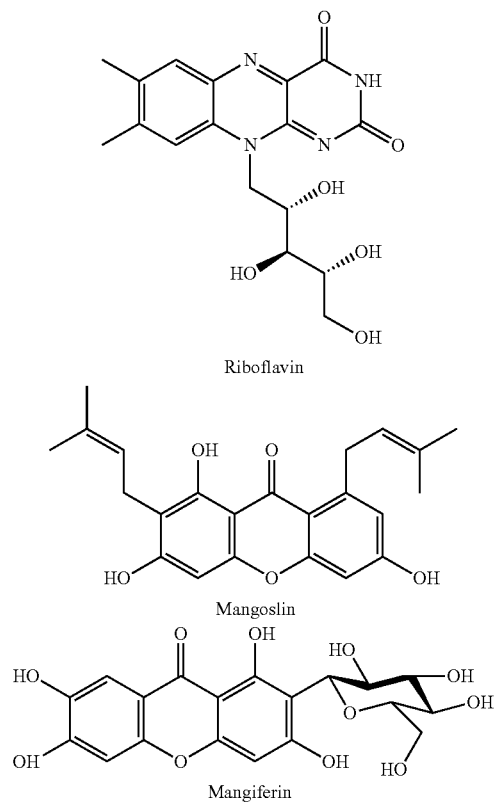

Riboflavin

Mangoslin

Mangiferin

This example demonstrates that a relatively short nucleic acid probe, two triplet-repeats in length, containing terminal aromatic moieties can discriminate the pathogenic rCUG$^{exp}$-MBNL$_1$ from the short CUG-repeat-containing transcript, and is able to disrupt the rCUG$^{exp}$-MBNL$_1$ complex. In addition to the benefits of being small in size, the modular design, high recognition specificity and selectivity of MPγPNA probe can target RNA-repeat expansions and is applicable not only to rCUG$^{exp}$ but also to a broad range of other repeated sequences, as a possible treatment for DM1, as well as a number of other related neuromuscular and neurodegenerative disorders.

The following numbered clauses provide non-limiting examples of various aspects of the invention:

Clause 1. A genetic recognition reagent, comprising: a nucleic acid or nucleic acid analog backbone, having a first end and a second end, and having from three to eight ribose, deoxyribose, or nucleic acid analog backbone residues; nucleobases, that may be the same or different, linked in a sequence complementary to a target nucleic acid to a plurality of the ribose, deoxyribose, or nucleic acid analog backbone residues; a first aryl moiety linked by a linker to the first end of the nucleic acid or nucleic acid analog backbone; and a second aryl moiety that is optionally the same as the first aryl moiety, linked by a linker to the second end of the of the nucleic acid or nucleic acid analog backbone, wherein the aryl moieties stack with aryl moieties of an adjacent recognition reagent when recognition reagents are hybridized to adjacent sequences of a target nucleic acid.

Clause 2. The genetic recognition reagent of clause 1, having the structure:

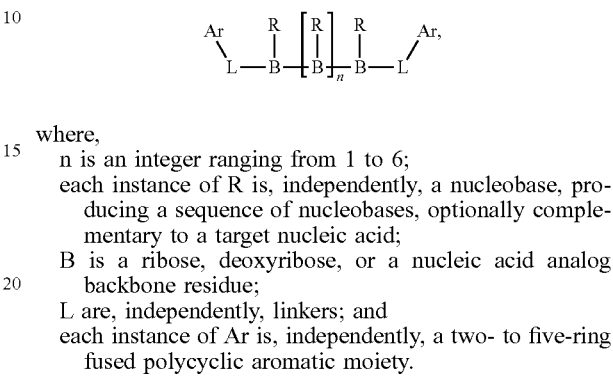

where,
n is an integer ranging from 1 to 6;
each instance of R is, independently, a nucleobase, producing a sequence of nucleobases, optionally complementary to a target nucleic acid;
B is a ribose, deoxyribose, or a nucleic acid analog backbone residue;
L are, independently, linkers; and
each instance of Ar is, independently, a two- to five-ring fused polycyclic aromatic moiety.

Clause 3. The genetic recognition reagent of clause 1 or 2, wherein the nucleic acid or nucleic acid analog backbone residues are nucleic acid analog backbone residues.

Clause 4. The genetic recognition reagent of clause 3, wherein the nucleic acid analog backbone residues comprise conformationally preorganized residues.

Clause 5. The genetic recognition reagent of clause 4, wherein the conformationally preorganized nucleic acid analog backbone residues are γPNA, LNA, or glycol nucleic acid backbone residues.

Clause 6. The genetic recognition reagent of clause 4, wherein the conformationally preorganized nucleic acid analog backbone residues are γPNA backbone residues.

Clause 7. The genetic recognition reagent of clause 6, wherein one or more of the γPNA backbone residues are substituted with a group comprising an ethylene glycol unit having from 1 to 100 ethylene glycol residues, such as:
—(OCH$_2$—CH$_2$)$_q$OP$_1$;          —(OCH$_2$—CH$_2$)$_q$—NHP$_1$;
—(SCH$_2$—CH$_2$)$_q$—SP$_1$;          —(OCH$_2$—CH$_2$)$_r$—OH;
—(OCH$_2$—CH$_2$)$_r$NH$_2$;     —(OCH$_2$—CH$_2$)$_r$—NHC(NH)NH$_2$; or —(OCH$_2$—CH$_2$)$_r$—S—S[CH$_2$CH$_2$]$_s$NHC(NH)NH$_2$, where P$_1$ is H, (C$_1$-C$_8$)alkyl, (C$_2$-C$_8$)alkenyl, (C$_2$-C$_8$)alkynyl, (C$_3$-C$_8$)aryl, (C$_3$-C$_8$)cycloalkyl, (C$_3$-C$_8$)aryl(C$_1$-C$_6$)alkylene or (C$_3$-C$_8$)cycloalkyl(C$_1$-C$_6$)alkylene; q is an integer from 0 to 50; r is an integer from 1 to 50, and s is an integer from 1 to 50, and optionally attached to the one or more γPNA backbone residues by a (C$_1$-C$_6$) divalent hydrocarbyl linker.

Clause 8. The genetic recognition reagent of clause 4, wherein the conformationally preorganized nucleic acid analog backbone residues are L-γPNA.

Clause 9. The genetic recognition reagent of any one of clauses 1-8, having the structure:

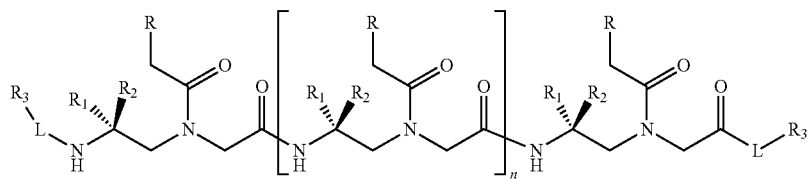

where, R are independently, nucleobases;
n is an integer ranging from 1 and 6, such as 1, 2, 3, 4, 5, or 6;
L are, independently, linkers;
$R_1$ and $R_2$ are each attached to a gamma carbon, and are, independently: H; a guanidine-containing group; an amino acid side chain; linear or branched ($C_1$-$C_8$)alkyl, ($C_2$-$C_8$)alkenyl, ($C_2$-$C_8$)alkynyl, ($C_1$-$C_8$)hydroxyalkyl, ($C_3$-$C_8$)aryl, ($C_3$-$C_8$)cycloalkyl, ($C_3$-$C_8$)aryl($C_1$-$C_6$)alkylene, ($C_3$-$C_8$)cycloalkyl($C_1$-$C_6$)alkylene, optionally substituted with an ethylene glycol unit comprising from 1 to 50 ethylene glycol moieties; —$CH_2$—($OCH_2$—$CH_2$)$_q$$OP_1$; —$CH_2$—($OCH_2$—$CH_2$)$_q$—$NHP_1$; —$CH_2$—($SCH_2$—$CH_2$)$_q$—$SP_1$; —$CH_2$—($OCH_2$—$CH_2$)$_r$—OH; —$CH_2$—($OCH_2$—$CH_2$)$_r$—$NH_2$; —$CH_2$—($OCH_2$—$CH_2$)$_r$—NHC(NH)$NH_2$; or —$CH_2$—($OCH_2$—$CH_2$)$_r$—S—S[$CH_2CH_2$]$_s$NHC(NH)$NH_2$, where $P_1$ is H, ($C_1$-$C_8$)alkyl, ($C_2$-$C_8$)alkenyl, ($C_2$-$C_8$)alkynyl, ($C_3$-$C_8$)aryl, ($C_3$-$C_8$)cycloalkyl, ($C_3$-$C_8$)aryl($C_1$-$C_6$)alkylene or ($C_3$-$C_8$)cycloalkyl($C_1$-$C_6$)alkylene; q is an integer from 0 to 50; r is an integer from 1 to 50, and s is an integer from 1 to 50; and
$R_3$ are, independently, two- to five-ring fused polycyclic aromatic moieties,
or a pharmaceutically-acceptable salt thereof.
Clause 10. The genetic recognition reagent of clause 9, wherein each linker independently comprises one or more guanidine-containing groups, one or more amino acid side chains, or one or more contiguous amino acid residues.
Clause 11. The genetic recognition reagent of clause 9, wherein each instance of L comprises, a first amino acid residue having the side group

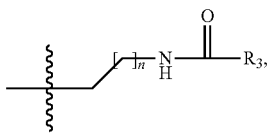

where n ranges from 1 to 5, and both N-terminal and C-terminal arginine residues attached to each of the first amino acid residues.
Clause 12. The genetic recognition reagent of clause 11, wherein n ranges from 1 to 3.
Clause 13. The genetic recognition reagent of any one of clauses 1-12, having the structure:

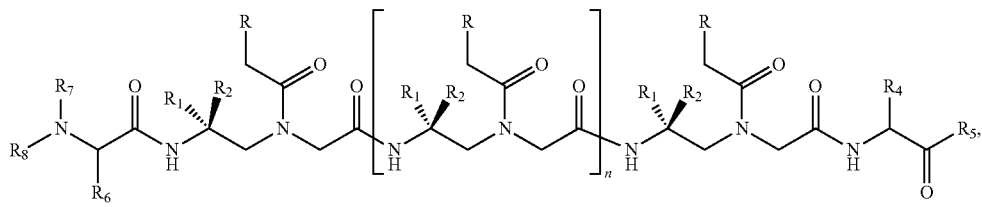

where,
R are independently, nucleobases;
n is an integer ranging from 1 and 6, such as 1, 2, 3, 4, 5, or 6;
$R_1$ and $R_2$ are each attached to a gamma carbon, and are, independently: H; a guanidine-containing group; an amino acid side chain; linear or branched ($C_1$-$C_8$)alkyl, ($C_2$-$C_8$)alkenyl, ($C_2$-$C_8$)alkynyl, ($C_1$-$C_8$)hydroxyalkyl, ($C_3$-$C_8$)aryl, ($C_3$-$C_8$)cycloalkyl, ($C_3$-$C_8$)aryl($C_1$-$C_6$)alkylene, ($C_3$-$C_8$)cycloalkyl($C_1$-$C_6$)alkylene, optionally substituted with an ethylene glycol unit comprising from 1 to 50 ethylene glycol moieties; —$CH_2$—($OCH_2$—$CH_2$)$_q$$OP_1$; —$CH_2$—($OCH_2$—$CH_2$)$_q$—$NHP_1$; —$CH_2$—($SCH_2$—$CH_2$)$_q$—$SP_1$; —$CH_2$—($OCH_2$—$CH_2$)$_r$—OH; —$CH_2$—($OCH_2$—$CH_2$)$_r$—$NH_2$; —$CH_2$—($OCH_2$—$CH_2$)$_r$—NHC(NH)$NH_2$; or —$CH_2$—($OCH_2$—$CH_2$)$_r$—S—S[$CH_2CH_2$]$_s$NHC(NH)$NH_2$, where $P_1$ is H, ($C_1$-$C_8$)alkyl, ($C_2$-$C_8$)alkenyl, ($C_2$-$C_8$)alkynyl, ($C_3$-$C_8$)aryl, ($C_3$-$C_8$)cycloalkyl, ($C_3$-$C_8$)aryl($C_1$-$C_6$)alkylene or ($C_3$-$C_8$)cycloalkyl($C_1$-$C_6$)alkylene; q is an integer from 0 to 50; r is an integer from 1 to 50, and s is an integer from 1 to 50;
one of $R_4$ or $R_5$, and one of $R_6$, $R_7$, or $R_8$ are -L-$R_3$, where $R_3$ are, independently, two- to five-ring fused polycyclic aromatic moieties, and L is a linker, and the remainder of $R_4$, $R_5$, $R_6$, $R_7$, and $R_8$ are each, independently: H; one or more contiguous amino acid residues; a guanidine-containing group; an amino acid side chain; linear or branched ($C_1$-$C_8$)alkyl, ($C_2$-$C_8$)alkenyl, ($C_2$-$C_8$)alkynyl, ($C_1$-$C_8$)hydroxyalkyl, ($C_3$-$C_8$)aryl, ($C_3$-$C_8$)cycloalkyl, ($C_3$-$C_8$)aryl($C_1$-$C_6$)alkylene, ($C_3$-$C_8$)cycloalkyl($C_1$-$C_6$)alkylene, optionally substituted with an ethylene glycol unit comprising from 1 to 50 ethylene glycol moieties; —$CH_2$—($OCH_2$—$CH_2$)$_q$$OP_1$; —$CH_2$—($OCH_2$—$CH_2$)$_q$—$NHP_1$; —$CH_2$—($SCH_2$—$CH_2$)$_q$—$SP_1$; —$CH_2$—($OCH_2$—$CH_2$)$_r$—OH; —$CH_2$—($OCH_2$—$CH_2$)$_r$—$NH_2$; —$CH_2$—($OCH_2$—$CH_2$)$_r$—NHC(NH)$NH_2$; or —$CH_2$—($OCH_2$—$CH_2$)$_r$—S—S[$CH_2CH_2$]$_s$NHC(NH)$NH_2$, where $P_1$ is H, ($C_1$-$C_8$)alkyl, ($C_2$-$C_8$)alkenyl, ($C_2$-$C_8$)alkynyl, ($C_3$-$C_8$)aryl, ($C_3$-$C_8$)cycloalkyl, ($C_3$-$C_8$)aryl($C_1$-$C_6$)alkylene or ($C_3$-$C_8$)cycloalkyl($C_1$-$C_6$)alkylene; q is an integer from 0 to 50; r is an integer from 1 to 50, and s is an integer from 1 to 50,
or a pharmaceutically-acceptable salt thereof.
Clause 14. The genetic recognition reagent of clause 13, wherein one or more of $R_1$, $R_2$, $R_4$, $R_5$, $R_6$, $R_7$, or $R_8$ is ($C_1$-$C_6$)alkyl substituted with —($OCH_2$—$CH_2$)$_q$$OP_1$; —($OCH_2$—$CH_2$)$_q$—$NHP_1$; —($SCH_2$—$CH_2$)$_q$—$SP_1$; —($OCH_2$—$CH_2$)$_r$—OH; —($OCH_2$—$CH_2$)$_r$—$NH_2$; —($OCH_2$—$CH_2$)$_r$—NHC(NH)$NH_2$; or —($OCH_2$—$CH_2$)$_r$—S—S[$CH_2CH_2$]$_s$NHC(NH)$NH_2$, where $P_1$ is H, ($C_1$-$C_8$) alkyl, ($C_2$-$C_8$)alkenyl, ($C_2$-$C_8$)alkynyl, ($C_3$-$C_8$)aryl, ($C_3$-$C_8$)cycloalkyl, ($C_3$-$C_8$)aryl($C_1$-$C_6$)alkylene or ($C_3$-$C_8$)cycloalkyl($C_1$-$C_6$)alkylene; q is an integer from 0 to 50; r is an integer from 1 to 50, and s is an integer from 1 to 50.
Clause 15. The genetic recognition reagent of clause 13 or 14, wherein $R_4$ and $R_7$ are -L-$R_3$.
Clause 16. The genetic recognition reagent of any one of clauses 13-15, wherein $R_5$ and $R_8$ comprise an arginine residue.

Clause 17. The genetic recognition reagent of any one of clauses 1-16, having the structure:

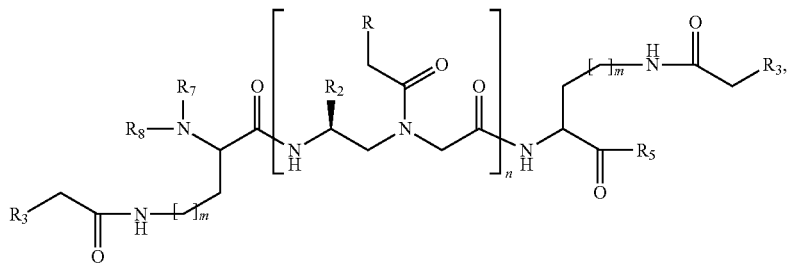

where,
- n is an integer ranging from 1 to 8;
- m is an integer ranging from 1 to 5;
- $R_2$ is attached to a gamma carbon, and is: a guanidine-containing group; an amino acid side chain; linear or branched $(C_1-C_8)$alkyl, $(C_2-C_8)$alkenyl, $(C_2-C_8)$alkynyl, $(C_1-C_8)$hydroxyalkyl, $(C_3-C_8)$aryl, $(C_3-C_8)$cycloalkyl, $(C_3-C_8)$aryl$(C_1-C_6)$alkylene, $(C_3-C_8)$cycloalkyl$(C_1-C_6)$alkylene, optionally substituted with an ethylene glycol unit comprising from 1 to 50 ethylene glycol moieties; —$CH_2$—$(OCH_2$—$CH_2)_q OP_1$; —$CH_2$—$(OCH_2$—$CH_2)_q$—$NHP_1$; —$CH_2$—$(SCH_2$—$CH_2)_q$—$SP_1$; —$CH_2$—$(OCH_2$—$CH_2)_r$—OH; —$CH_2$—$(OCH_2$—$CH_2)_r$—$NH_2$; —$CH_2$—$(OCH_2$—$CH_2)_r$—$NHC(NH)NH_2$; or —$CH_2$—$(OCH_2$—$CH_2)_r$—S—$S[CH_2CH_2]_s NHC(NH)NH_2$, where $P_1$ is H, $(C_1-C_8)$alkyl, $(C_2-C_8)$alkenyl, $(C_2-C_8)$alkynyl, $(C_3-C_8)$aryl, $(C_3-C_8)$cycloalkyl, $(C_3-C_8)$aryl$(C_1-C_6)$alkylene or $(C_3-C_8)$cycloalkyl$(C_1-C_6)$alkylene; q is an integer from 0 to 50; r is an integer from 1 to 50, and s is an integer from 1 to 50;
- $R_3$ is an unsubstituted fused-ring polycyclic aromatic moiety, such as pentalene, indene, naphthalene, azulene, heptalene, biphenylene, as-indacene, s-indacene, acenaphthylene, fluorene, phenalene, phenanthrene, anthracene, fluoranthene, acephenanthrylene, aceanthrylene, triphenylene, pyrene, chrysene, naphthacene/tetracene, pleiadene, picene, or perylene; and
- each of $R_5$, $R_7$, and $R_8$ are, independently, H, a guanidine-containing group such as

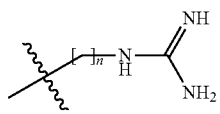

where n=1, 2, 3, 4, or 5, an amino acid side chain, or one or more contiguous amino acid residues,
or a pharmaceutically-acceptable salt thereof.

Clause 18. The genetic recognition reagent of clause 17, wherein one or more of $R_1$, $R_2$, $R_4$, $R_5$, $R_6$, $R_7$, or $R_8$ is $(C_1-C_6)$alkyl substituted with —$(OCH_2$—$CH_2)_q OP_1$; —$(OCH_2$—$CH_2)_q$—$NHP_1$; —$(SCH_2$—$CH_2)_q$—$SP_1$; —$(OCH_2$—$CH_2)_r$—OH; —$(OCH_2$—$CH_2)_r$—$NH_2$; —$(OCH_2$—$CH_2)_r$—$NHC(NH)NH_2$; or —$(OCH_2$—$CH_2)_r$—S—$S[CH_2CH_2]_s NHC(NH)NH_2$, where $P_1$ is H, $(C_1-C_8)$alkyl, $(C_2-C_8)$alkenyl, $(C_2-C_8)$alkynyl, $(C_3-C_8)$aryl, $(C_3-C_8)$cycloalkyl, $(C_3-C_8)$aryl$(C_1-C_6)$alkylene or $(C_3-C_8)$cycloalkyl$(C_1-C_6)$alkylene; q is an integer from 0 to 50; r is an integer from 1 to 50, and s is an integer from 1 to 50.

Clause 19. The genetic recognition reagent of clause 17, wherein $R_2$ is —$CH_2$—O—$CH_2$—$CH_2$—O—$CH_2$—$CH_2$—OH, $R_8$ is H, $R_5$ is Arg-Dab(pyrene)-, Arg-Orn(pyrene)-, or Arg-Lys(pyrene)-; and $R_7$ is -Dab(pyrene)-Arg, -Orn(pyrene)-Arg, or -Lys(pyrene)-Arg, optionally where the chiral centers of Arg, Dab, Orn, and Lys, are L-Arg, LDab, L-Orn, and L-Lys.

Clause 20. The genetic recognition reagent of any one of clauses 2-19, wherein both instances of the two- to five-ring fused polycyclic aromatic moieties are the same.

Clause 21. The genetic recognition reagent of any one of clauses 2-20, wherein one or both of the two- to five-ring fused polycyclic aromatic moieties is unsubstituted or substituted pentalene, indene, naphthalene, azulene, heptalene, biphenylene, as-indacene, s-indacene, acenaphthylene, fluorene, phenalene, phenanthrene, anthracene, fluoranthene, acephenanthrylene, aceanthrylene, triphenylene, pyrene, chrysene, naphthacene/tetracene, pleiadene, picene, or perylene, optionally substituted with one or more hetero atoms such as O, N, P, and/or S.

Clause 22. The genetic recognition reagent of any one of clauses 2-21, wherein one or both of the two- to five-ring fused polycyclic aromatic moieties comprises riboflavin (vitamin B2), mangostin, or mangiferin.

Clause 23. The genetic recognition reagent of any one of clauses 9-22, wherein $R_1$ and $R_2$ are different in two or more gamma carbons.

Clause 24. The genetic recognition reagent of clause 23, wherein $R_1$ is H in the two or more gamma carbons in which $R_1$ and $R_2$ are different.

Clause 25. The genetic recognition reagent of clause 23, wherein $R_2$ is H in the two or more gamma carbons in which $R_1$ and $R_2$ are different.

Clause 26. The genetic recognition reagent of any one of clauses 1-25, comprising a guanidine moiety.

Clause 27. The genetic recognition reagent of any one of clauses 1-26, comprising the guanidine-containing group

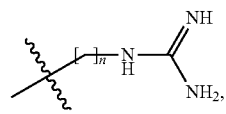

where n=1, 2, 3, 4, or 5.

Clause 28. The genetic recognition reagent of any one of clauses 9-27, wherein, $R_2$ is —$CH_2$—$(OCH_2$—$CH_2)_r$—OH, wherein r is an integer of from 1 to 50, from 1 to 10, or 2.

Clause 29. The genetic recognition reagent of any one of clauses 9-27, wherein, $R_2$ is —$CH_2$—O—$CH_2$—$CH_2$—O—$CH_2$—$CH_2$—OH, and $R_3$ is pyrene.

Clause 30. The genetic recognition reagent of any one of clauses 1-29, wherein the linker comprises from 5 to 25 atoms, or a total of from 1 to 10 total C, O, P, N, and S atoms.

Clause 31. The genetic recognition reagent of any one of clauses 1-30, wherein the nucleobase sequence is fully complementary to a nucleic acid having an expanded repeat associated with a repeat expansion disease, such as FRDA, FRAXA, FRAXE, SCA1, SCA2, SCA3 (MJD), SCA6, SCA7, SCA17, DRPLA, SBMA, HD, MD1, MD2, FXTAS, SCA8, SCA10, SCA12, HDL2, or ALS.

Clause 32. The genetic recognition reagent of clause 31, wherein the expanded repeat has one of the following sequences: $(GAA)_n$, $(CGG)_n$, $(CCG)_n$, $(CAG)_n$, $(CTG)_n$, $(CCTG)_n$, $(ATTCT)_n$, or $(GGGGCC)_n$, where n is at least 3.

Clause 33. A method of binding a nucleic acid, comprising contacting a nucleic acid having a target sequence with a genetic recognition reagent of any one of clauses 1-Clause 32.

Clause 34. The method of clause 33, wherein the nucleobase sequence of the genetic recognition reagent is fully complementary to a nucleic acid having an expanded repeat associated with a repeat expansion disease, such as FRDA, FRAXA, FRAXE, SCA1, SCA2, SCA3 (MJD), SCA6, SCA7, SCA17, DRPLA, SBMA, HD, MD1, MD2, FXTAS, SCA8, SCA10, SCA12, HDL2, or ALS.

Clause 35. The method of clause 34, wherein the expanded repeat has one of the following sequences: $(GAA)_n$, $(CGG)_n$, $(CCG)_n$, $(CAG)_n$, $(CTG)_n$, $(CCTG)_n$, $(ATTCT)_n$, or $(GGGGCC)_n$, where n is at least 3.

Clause 36. A method of knocking down expression of an mRNA in a cell, comprising contacting a target sequence of the mRNA with a genetic recognition reagent of any one of clauses 1-32 having a nucleobase sequence complementary to the target sequence.

Clause 37. The method of clause 36, wherein the nucleobase sequence of the genetic recognition reagent is fully complementary to a nucleic acid having an expanded repeat associated with a repeat expansion disease, such as FRDA, FRAXA, FRAXE, SCA1, SCA2, SCA3 (MJD), SCA6, SCA7, SCA17, DRPLA, SBMA, HD, MD1, MD2, FXTAS, SCA8, SCA10, SCA12, HDL2, or ALS.

Clause 38. The method of clause 37, wherein the expanded repeat has one of the following sequences: $(GAA)_n$, $(CGG)_n$, $(CCG)_n$, $(CAG)_n$, $(CTG)_n$, $(CCTG)_n$, $(ATTCT)_n$, or $(GGGGCC)_n$, where n is at least 3.

Clause 39. A method of identifying a target sequence of a nucleic acid in a sample, comprising: contacting a sample comprising nucleic acid with the genetic recognition reagent of any one of clauses 1-32, in which the aryl moieties produce a first fluorescent emission when exposed to an excitation frequency of light when not concatenated on a target sequence, and a second fluorescent emission different from the first fluorescent emission when exposed to an excitation frequency of light when concatenated on a target sequence, and determining the presence of the target sequence in the sample by exciting the fluorescent aromatic moieties and measuring the amount of the second fluorescent signal produced in the sample by the fluorescent aromatic moieties.

Clause 40. The method of clause 39, wherein the fluorescent aromatic moieties are pyrene.

Clause 41. The method of clause 39, wherein the nucleobase sequence of the genetic recognition reagent is fully complementary to a nucleic acid having an expanded repeat associated with a repeat expansion disease, such as FRDA, FRAXA, FRAXE, SCA1, SCA2, SCA3 (MJD), SCA6, SCA7, SCA17, DRPLA, SBMA, HD, MD1, MD2, FXTAS, SCAB, SCA10, SCA12, HDL2, or ALS.

Clause 42. The method of clause 39, wherein the expanded repeat has one of the following sequences: $(GAA)_n$, $(CGG)_n$, $(CCG)_n$, $(CAG)_n$, $(CTG)_n$, $(CCTG)_n$, $(ATTCT)_n$, or $(GGGGCC)_n$, where n is at least 3.

Clause 43. A composition comprising the genetic recognition reagent of any one of clauses 1-32, and a pharmaceutically-acceptable carrier.

The present invention has been described with reference to certain exemplary embodiments, dispersible compositions and uses thereof. However, it will be recognized by those of ordinary skill in the art that various substitutions, modifications or combinations of any of the exemplary embodiments may be made without departing from the spirit and scope of the invention. Thus, the invention is not limited by the description of the exemplary embodiments.

We claim:

1. A genetic recognition reagent, comprising:
   a nucleic acid analog backbone, wherein the nucleic acid analog backbone comprises:
   a first end and a second end, and
   three to eight units, wherein each unit is independently a nucleic acid analog backbone residue;
   a plurality of nucleobases wherein each nucleobase of the plurality of nucleobases is independently linked to a unit of the three to eight units, wherein the plurality of nucleobases has a sequence that is complementary to a target sequence of a target nucleic acid;
   a first aryl moiety linked by a linker to the first end of the nucleic acid analog backbone; and
   a second aryl moiety, linked by a linker to the second end of the nucleic acid analog backbone, wherein the first aryl moiety or the second aryl moiety stacks with an aryl moiety of an adjacent recognition reagent when the genetic recognition reagent and the adjacent recognition reagent are hybridized to adjacent target sequences of the target nucleic acid.

2. The genetic recognition reagent of claim 1, having the structure:

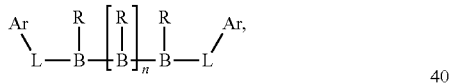

where,
   n is an integer ranging from 1 to 6;
   each instance of R is, independently, a nucleobase of the plurality of nucleobases;
   B is a unit of the three to eight units;
   one instance of Ar is the first aryl moiety, and another instance of Ar is the second aryl moiety, wherein the first aryl moiety and the second aryl moiety are each independently a two- to five-ring fused polycyclic aromatic moiety; and
   one instance of L is the linker to the first end of the nucleic acid analog backbone, and another instance of L is the linker to the second end of the nucleic acid analog backbone.

3. The genetic recognition reagent of claim 1, wherein the nucleic acid analog backbone residues are RNA backbone residues.

4. The genetic recognition reagent of claim 3, wherein one or more of the γPNA backbone residues are substituted with a group comprising an ethylene glycol unit, wherein the group comprising the ethylene glycol unit is: —(OCH$_2$—CH$_2$)$_q$OP$_1$; —(OCH$_2$—CH$_2$)$_q$—NHP$_1$; —(OCH$_2$—CH$_2$)$_r$—OH; —(OCH$_2$—CH$_2$)$_r$—NH$_2$; —(OCH$_2$—CH$_2$)$_r$—NHC(NH)NH$_2$; or —(OCH$_2$—CH$_2$)$_r$—S—S[CH$_2$CH$_2$]$_s$NHC(NH)NH$_2$, where P$_1$ is H, (C$_1$-C$_8$)alkyl, (C$_2$-C$_8$)alkenyl, (C$_2$-C$_8$)alkynyl, (C$_3$-C$_8$)aryl, (C$_3$-C$_8$)cycloalkyl, (C$_3$-C$_8$)aryl(C$_1$-C$_6$)alkylene or (C$_3$-C$_8$)cycloalkyl(C$_1$-C$_6$)alkylene; q is an integer from 0 to 50; r is an integer from 1 to 50, and s is an integer from 1 to 50, wherein the group comprising the ethylene glycol unit is attached to the one or more γPNA backbone residues by a (C$_1$-C$_6$) divalent hydrocarbyl linker or a covalent bond.

5. The genetic recognition reagent of claim 1, having the structure:

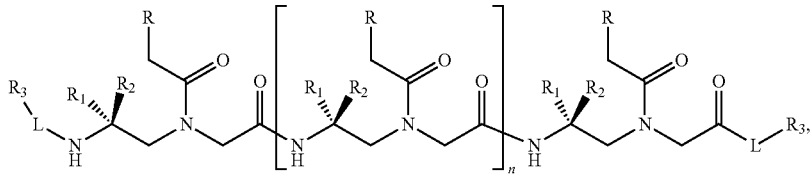

where,
   each R is independently, a nucleobase of the plurality of nucleobases;
   n is 1, 2, 3, 4, 5, or 6;
   one instance of L is the linker to the first end of the nucleic acid analog backbone, and another instance of L is the linker to the second end of the nucleic acid analog backbone, wherein the linker to the first end of the nucleic acid analog backbone and the linker to the second end of the nucleic acid analog backbone each independently comprises one or more guanidine-containing groups, one or more amino acid side chains, or one or more contiguous amino acid residues;
   each R$_3$ is, independently, two- to five-ring fused polycyclic aromatic moieties,
   R$_1$ and R$_2$ are each attached to a gamma carbon, and are, independently:
   H, a guanidine-containing group, methyl, ethyl, an amino acid side chain, linear or branched ([C$_3$-C$_8$]alkyl, (C$_2$-C$_8$)alkenyl, (C$_2$-C$_8$)alkynyl, (C$_1$-C$_8$)hydroxyalkyl, (C$_3$-C$_8$)aryl, (C$_3$-C$_8$)cycloalkyl, (C$_3$-C$_8$)aryl(C$_1$-C$_6$)alkylene, or (C$_3$-C$_8$)cycloalkyl (C$_1$-C$_6$)alkylene; or
   a guanidine-containing group, methyl, ethyl, an amino acid side chain, linear or branched (C$_3$-C$_8$) alkyl, (C$_2$-C$_8$)alkenyl, (C$_2$-C$_8$)alkynyl, (C$_1$-C$_8$)hydroxyalkyl, (C$_3$-C$_8$)aryl, (C$_3$-C$_8$)cycloalkyl, (C$_3$-C$_8$)aryl(C$_1$-C$_6$)alkylene, or (C$_3$-C$_8$)cycloalkyl(C$_1$-C$_6$)alkylene, wherein the guanidine-containing group, methyl, ethyl, an amino acid side chain, linear or branched (C$_3$-C$_8$)alkyl, (C$_2$-C$_8$)alkenyl, (C$_2$-C$_8$)alkynyl, (C$_1$-C$_8$)hydroxyalkyl, (C$_3$-C$_8$) aryl, (C$_3$-C$_8$)cycloalkyl, (C$_3$-C$_8$)aryl(C$_1$-C$_6$)alkylene, or (C$_3$-C$_8$)cycloalkyl(C$_1$-C$_6$)alkylene is substituted with an ethylene glycol unit comprising from 1 to 50 ethylene glycol moieties, —(OCH$_2$—CH$_2$)$_q$OP$_1$, —(OCH$_2$—CH$_2$)$_q$—NHP$_1$, —(SCH$_2$—CH$_2$)$_q$—SP$_1$, —(OCH$_2$—CH$_2$)$_r$—OH, —(OCH$_2$—CH$_2$)$_r$—NH$_2$, —(OCH$_2$—CH$_2$)$_r$—NHC(NH)NH$_2$, or —(OCH$_2$—CH$_2$)$_r$—S—S[CH$_2$CH$_2$]$_s$NHC(NH) NH$_2$, where P$_1$ is H, (C$_1$-C$_8$)alkyl, (C$_2$-C$_8$)alkenyl, (C$_2$-C$_8$)alkynyl, (C$_3$-C$_8$)aryl, (C$_3$-C$_8$)cycloalkyl, (C$_3$-C$_8$)aryl(C$_1$-C$_6$)alkylene or (C$_3$-C$_8$)cycloalkyl (C$_1$-C$_6$)alkylene; q is an integer from 0 to 50; r is an integer from 1 to 50, and s is an integer from 1 to 50,
   or a pharmaceutically-acceptable salt thereof.

6. The genetic recognition reagent of claim 1, having the structure:

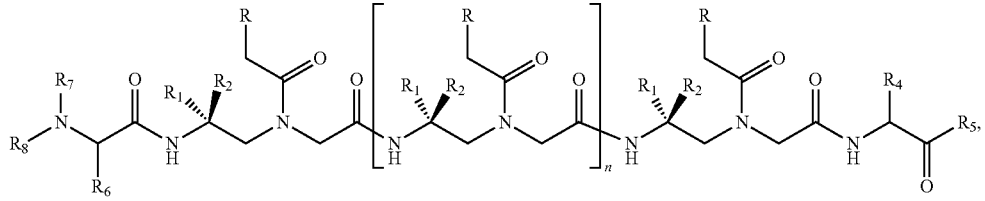

where,
- each R is independently, a nucleobase of the plurality of nucleobases;
- n is 1, 2, 3, 4, 5, or 6;
- $R_1$ and $R_2$ are independently: H, a guanidine-containing group; an amino acid side chain; methyl, ethyl, linear or branched $(C_3$-$C_8)$alkyl, $(C_2$-$C_8)$alkenyl, $(C_2$-$C_8)$alkynyl, $(C_1$-$C_8)$hydroxyalkyl, $(C_3$-$C_8)$aryl, $(C_3$-$C_8)$cycloalkyl, $(C_3$-$C_8)$aryl$(C_1$-$C_6)$alkylene, or $(C_3$-$C_8)$cycloalkyl$(C_1$-$C_6)$alkylene; or a guanidine-containing group, an amino acid side chain, methyl, ethyl, linear or branched $(C_3$-$C_8)$alkyl, $(C_2$-$C_8)$alkenyl, $(C_2$-$C_8)$alkynyl, $(C_1$-$C_8)$hydroxyalkyl, $(C_3$-$C_8)$aryl, $(C_3$-$C_8)$cycloalkyl, $(C_3$-$C_8)$aryl$(C_1$-$C_6)$alkylene, $(C_3$-$C_8)$cycloalkyl$(C_1$-$C_6)$alkylene, wherein the guanidine-containing group, the amino acid side chain, methyl, ethyl, linear or branched $(C_3$-$C_8)$alkyl, $(C_2$-$C_8)$alkenyl, $(C_2$-$C_8)$alkynyl, $(C_1$-$C_8)$hydroxyalkyl, $(C_3$-$C_8)$aryl, $(C_3$-$C_8)$cycloalkyl, $(C_3$-$C_8)$aryl$(C_1$-$C_6)$alkylene, $(C_3$-$C_8)$cycloalkyl$(C_1$-$C_6)$alkylene is substituted with an ethylene glycol unit comprising from 1 to 50 ethylene glycol moieties; —$(OCH_2$—$CH_2)_q OP_1$; —$(OCH_2$—$CH_2)_q$—$NHP_1$; —$(SCH_2$—$CH_2)_q$—$SP_1$; —$(OCH_2$—$CH_2)_r$—$OH$; —$(OCH_2$—$CH_2)_r$—$NH_2$; —$(OCH_2$—$CH_2)_r$—$NHC(NH)NH_2$; or —$(OCH_2$—$CH_2)_r$—$S$—$S[CH_2CH_2]_s NHC(NH)NH_2$, where $P_1$ is H, $(C_1$-$C_8)$alkyl, $(C_2$-$C_8)$alkenyl, $(C_2$-$C_8)$alkynyl, $(C_3$-$C_8)$aryl, $(C_3$-$C_8)$cycloalkyl, $(C_3$-$C_8)$aryl$(C_1$-$C_6)$alkylene or $(C_3$-$C_8)$cycloalkyl$(C_1$-$C_6)$alkylene; q is an integer from 0 to 50; r is an integer from 1 to 50, and s is an integer from 1 to 50; and
- one of $R_4$ and $R_5$, and one of $R_6$, $R_7$, and $R_8$ are -L-$R_3$, where each $R_3$ are, independently, two- to five-ring fused polycyclic aromatic moieties, wherein one instance of L is the linker to the first end of the nucleic acid analog backbone, and another instance of L is the linker to the second end of the nucleic acid analog backbone, and each of $R_4$, $R_5$, $R_6$, $R_7$, and $R_8$ that is not -L-$R_3$ are, independently: H, one or more contiguous amino acid residues, a guanidine-containing group, an amino acid side chain, methyl, ethyl, linear or branched $(C_3$-$C_8)$alkyl, $(C_2$-$C_8)$alkenyl, $(C_2$-$C_8)$alkynyl, $(C_1$-$C_8)$hydroxyalkyl, $(C_3$-$C_8)$aryl, $(C_3$-$C_8)$cycloalkyl, $(C_3$-$C_8)$aryl$(C_1$-$C_6)$alkylene, or $(C_3$-$C_8)$cycloalkyl$(C_1$-$C_6)$alkylene; or one or more contiguous amino acid residues, a guanidine-containing group, an amino acid side chain, methyl, ethyl, linear or branched $(C_3$-$C_8)$alkyl, $(C_2$-$C_8)$alkenyl, $(C_2$-$C_8)$alkynyl, $(C_1$-$C_8)$hydroxyalkyl, $(C_3$-$C_8)$aryl, $(C_3$-$C_8)$cycloalkyl, $(C_3$-$C_8)$aryl$(C_1$-$C_6)$alkylene, or $(C_3$-$C_8)$cycloalkyl$(C_1$-$C_6)$alkylene, wherein the one or more contiguous amino acid residues, the guanidine-containing group, the amino acid side chain, methyl, ethyl, linear or branched $(C_3$-$C_8)$alkyl, $(C_2$-$C_8)$alkenyl, $(C_2$-$C_8)$alkynyl, $(C_1$-$C_8)$hydroxyalkyl, $(C_3$-$C_8)$aryl, $(C_3$-$C_8)$cycloalkyl, $(C_3$-$C_8)$aryl$(C_1$-$C_6)$alkylene, or $(C_3$-$C_8)$cycloalkyl$(C_1$-$C_6)$alkylene is substituted with an ethylene glycol unit comprising from 1 to 50 ethylene glycol moieties; —$(OCH_2$—$CH_2)_q OP_1$; —$(OCH_2$—$CH_2)_q$—$NHP_1$; —$(SCH_2$—$CH_2)_q$—$SP_1$; —$(OCH_2$—$CH_2)_r$—$OH$; —$(OCH_2$—$CH_2)_r$—$NH_2$; —$(OCH_2$—$CH_2)_r$—$NHC(NH)NH_2$; or —$(OCH_2$—$CH_2)_r$—$S$—$S[CH_2CH_2]_s NHC(NH)NH_2$, where $P_1$ is H, $(C_1$-$C_8)$alkyl, $(C_2$-$C_8)$alkenyl, $(C_2$-$C_8)$alkynyl, $(C_3$-$C_8)$aryl, $(C_3$-$C_8)$cycloalkyl, $(C_3$-$C_8)$aryl$(C_1$-$C_6)$alkylene or $(C_3$-$C_8)$cycloalkyl$(C_1$-$C_6)$alkylene; q is an integer from 0 to 50; r is an integer from 1 to 50, and s is an integer from 1 to 50, or a pharmaceutically-acceptable salt thereof.

7. The genetic recognition reagent of claim 6, wherein one or more of any $R_1$, $R_2$, $R_4$, $R_5$, $R_6$, $R_7$, or $R_8$ that is not -L-$R_3$ is $(C_1$-$C_8)$alkyl substituted with —$(OCH_2$—$CH_2)_q OP_1$; —$(OCH_2$—$CH_2)_q$—$NHP_1$; —$(SCH_2$—$CH_2)_q$—$SP_1$; —$(OCH_2$—$CH_2)_r$—$OH$; —$(OCH_2$—$CH_2)_r$—$NH_2$; —$(OCH_2$—$CH_2)_r$—$NHC(NH)NH_2$; or —$(OCH_2$—$CH_2)_r$—$S$—$S[CH_2CH_2]_s NHC(NH)NH_2$, where $P_1$ is H, $(C_1$-$C_8)$alkyl, $(C_2$-$C_8)$alkenyl, $(C_2$-$C_8)$alkynyl, $(C_3$-$C_8)$aryl, $(C_3$-$C_8)$cycloalkyl, $(C_3$-$C_8)$aryl$(C_1$-$C_6)$alkylene or $(C_3$-$C_8)$cycloalkyl$(C_1$-$C_6)$alkylene; q is an integer from 0 to 50; r is an integer from 1 to 50, and s is an integer from 1 to 50.

8. The genetic recognition reagent of claim 6, wherein $R_4$ and $R_7$ are -L-$R_3$.

9. The genetic recognition reagent of claim 6, wherein each of $R_5$ and $R_8$ comprise an arginine residue.

10. The genetic recognition reagent of claim 1, having the structure:

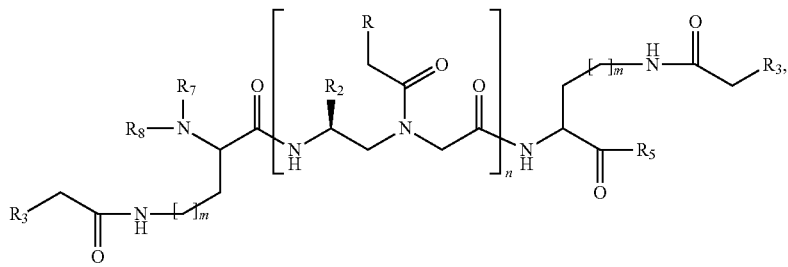

where,
- each R is independently, a nucleobase of the plurality of nucleobases;
- each n is independently an integer ranging from 1 and 8;
- each m is independently an integer ranging from 1 and 5;
- each $R_2$ is independently: a guanidine-containing group, an amino acid side chain, methyl, ethyl, linear or branched $(C_3-C_8)$alkyl, $(C_2-C_8)$alkenyl, $(C_2-C_8)$alkynyl, $(C_1-C_8)$hydroxyalkyl, $(C_3-C_8)$aryl, $(C_3-C_8)$cycloalkyl, $(C_3-C_8)$aryl$(C_1-C_6)$alkylene, or $(C_3-C_8)$cycloalkyl$(C_1-C_6)$alkylene; or an amino acid side chain, methyl, ethyl, linear or branched $(C_3-C_8)$alkyl, $(C_2-C_8)$alkenyl, $(C_2-C_8)$alkynyl, $(C_1-C_8)$hydroxyalkyl, $(C_3-C_8)$aryl, $(C_3-C_8)$cycloalkyl, $(C_3-C_8)$aryl$(C_1-C_6)$alkylene, or $(C_3-C_8)$cycloalkyl$(C_1-C_6)$alkylene, wherein the amino acid side chain, methyl, ethyl, linear or branched $(C_3-C_8)$alkyl, $(C_2-C_8)$alkenyl, $(C_2-C_8)$alkynyl, $(C_1-C_8)$hydroxyalkyl, $(C_3-C_8)$aryl, $(C_3-C_8)$cycloalkyl, $(C_3-C_8)$aryl$(C_1-C_6)$alkylene, or $(C_3-C_8)$cycloalkyl$(C_1-C_6)$alkylene is substituted with an ethylene glycol unit comprising from 1 to 50 ethylene glycol moieties; —(OCH$_2$—CH$_2$)$_q$OP$_1$; —(OCH$_2$—CH$_2$)$_q$—NHP$_1$; —(SCH$_2$—CH$_2$)$_q$—SP$_1$; —(OCH$_2$—CH$_2$)$_r$—OH; —(OCH$_2$—CH$_2$)$_r$—NH$_2$; —(OCH$_2$—CH$_2$)$_r$—NHC(NH)NH$_2$; or —(OCH$_2$—CH$_2$)$_r$—S—S[CH$_2$CH$_2$]$_s$NHC(NH)NH$_2$, where $P_1$ is H, $(C_1-C_8)$alkyl, $(C_2-C_8)$alkenyl, $(C_2-C_8)$alkynyl, $(C_3-C_8)$aryl, $(C_3-C_8)$cycloalkyl, $(C_3-C_8)$aryl$(C_1-C_6)$alkylene or $(C_3-C_8)$cycloalkyl$(C_1-C_6)$alkylene; q is an integer from 0 to 50; r is an integer from 1 to 50, and s is an integer from 1 to 50;
- $R_3$ is an unsubstituted fused-ring polycyclic aromatic moiety; and
- each of $R_5$, $R_7$, and $R_8$ are, independently H, a guanidine-containing group, an amino acid side chain, or one or more contiguous amino acid residues, or a pharmaceutically-acceptable salt thereof.

11. The genetic recognition reagent of claim 10, wherein $R_2$ is —CH$_2$—O—CH$_2$—CH$_2$—O—CH$_2$—CH$_2$—OH, $R_8$ is H, $R_5$ is Arg-Dab(pyrene)-, Arg-Orn(pyrene)-, or Arg-Lys(pyrene)-; and $R_7$ is -Dab(pyrene)-Arg, -Orn(pyrene)-Arg, or -Lys(pyrene)-Arg.

12. The genetic recognition reagent of claim 2, wherein either instance of Ar is unsubstituted or substituted pentalene, indene, naphthalene, azulene, heptalene, biphenylene, as-indacene, s-indacene, acenaphthylene, fluorene, phenalene, phenanthrene, anthracene, fluoranthene, acephenanthrylene, aceanthrylene, triphenylene, pyrene, chrysene, naphthacene/tetracene, pleiadene, picene, or perylene.

13. The genetic recognition reagent of claim 2, wherein either instance of Ar comprises riboflavin (vitamin B2), mangostin, or mangiferin.

14. The genetic recognition reagent of claim 1, comprising a guanidine-containing group that is

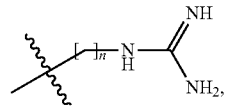

where n=1, 2, 3, 4, or 5.

15. The genetic recognition reagent of claim 5, wherein, $R_2$ is —CH$_2$—(OCH$_2$—CH$_2$)$_r$—OH, wherein r is an integer of from 1 to 50, from 1 to 10, or 2.

16. The genetic recognition reagent of claim 1, wherein the linker to the first end of the nucleic acid analog backbone or the linker to the second end of the nucleic acid analog backbone comprises from 5 to 25 atoms, or a total of from 1 to 10 C, O, P, N, and S atoms.

17. The genetic recognition reagent of claim 1, wherein the sequence that is complementary to the target sequence of the target nucleic acid is complementary to a nucleic acid having an expanded repeat associated with a repeat expansion disease.

18. The genetic recognition reagent of claim 17, wherein the expanded repeat has one of the following sequences: $(GAA)_n$, $(CGG)_n$, $(CCG)_n$, $(CAG)_n$, $(CTG)_n$, $(CCTG)_n$, $(ATTCT)_n$, or $(GGGGCC)_n$, where n is at least 3.

19. The genetic recognition reagent of claim 17, wherein the expanded repeat is $(GTG)_n$, where n is at least 3.

20. The genetic recognition reagent of claim 17, wherein the expanded repeat is $(GUG)_n$, where n is at least 3.

* * * * *

SEQUENCE LISTING

```
<160> NUMBER OF SEQ ID NOS: 2

<210> SEQ ID NO 1
<211> LENGTH: 18
<212> TYPE: RNA
<213> ORGANISM: Homo sapiens

<400> SEQUENCE: 1
cugcugcugc ugcugcug                                                 18

<210> SEQ ID NO 2
<211> LENGTH: 14
<212> TYPE: RNA
<213> ORGANISM: Artificial Sequence
<220> FEATURE:
<223> OTHER INFORMATION: Predicted RNA secondary structure

<400> SEQUENCE: 2
gcugcugcug cugc                                                     14
```